US008026053B2

(12) United States Patent
Samuels et al.

(10) Patent No.: US 8,026,053 B2
(45) Date of Patent: Sep. 27, 2011

(54) MUTATIONS OF THE PIK3CA GENE IN HUMAN CANCERS

(75) Inventors: Yardena Samuels, Potomac, MD (US);
Victor Velculescu, Dayton, MD (US);
Kenneth W. Kinzler, Bel Air, MD (US);
Bert Vogelstein, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 716 days.

(21) Appl. No.: 10/591,347

(22) PCT Filed: Feb. 18, 2005

(86) PCT No.: PCT/US2005/005193
§ 371 (c)(1),
(2), (4) Date: Mar. 18, 2009

(87) PCT Pub. No.: WO2005/091849
PCT Pub. Date: Oct. 6, 2005

(65) Prior Publication Data
US 2009/0208505 A1    Aug. 20, 2009

Related U.S. Application Data

(60) Provisional application No. 60/548,886, filed on Mar. 2, 2004.

(51) Int. Cl.
*C12Q 1/68* (2006.01)
(52) U.S. Cl. ............................................................ 435/6
(58) Field of Classification Search ........................ None
See application file for complete search history.

(56) References Cited

U.S. PATENT DOCUMENTS

| | | | |
|---|---|---|---|
| 5,824,492 A | 10/1998 | Hiles | |
| 5,846,824 A | 12/1998 | Hiles et al. | |
| 6,110,673 A | 8/2000 | Shayesteh | |
| 6,274,327 B1 | 8/2001 | Hiles | |
| 6,277,563 B1 | 8/2001 | Shayesteh | |
| 6,475,732 B1 | 11/2002 | Shayesteh | |
| 6,537,761 B1 | 3/2003 | Shayesteh | |
| 6,558,903 B1 | 5/2003 | Hodge | |
| 7,670,767 B1 * | 3/2010 | Shayesteh et al. ................. 435/6 |

FOREIGN PATENT DOCUMENTS
WO        01/16306        3/2001

OTHER PUBLICATIONS

Ma et al (Oncogene, 2000, 19:2739-2744, IDS).*
Philp, Amanda J. et al., "The phosphatidylinositol 3'- kinase p85alpha gene is an oncogene in human ovarian and colon tumors", Cancer Research, American Association for Cancer Research, Oct. 15, 2001, pp. 7426-7429, vol. 61, No. 20, US.
Y. Samuels et al., "Oncogneic Mutations of PIK3CA in Human Cancers," Cell Cycle, 2004, vol. 3, Issue 10, pp. e17-e20.
L. Zhang et al., "The Oncogene Phosphatidylinositol 3' Kinase Catalytic Subunit Alpha Promotes Angiogenesis via Vascular Endothelial Growth Factor in Ovarian Carcinoma," Cancer Research, Jul. 15, 2003, vol. 63, No. 14, pp. 4225-4231.
Y-Y Ma et al., "PIK3CA as an Oncogene in Cervical Cancer," Oncogene, May 25, 2000, vol. 19, No. 23, pp. 2739-2744.
K. Hill et al., "Specific Requirement for the p85-p110alpha Phosphatidylinositol 3-Kinase During Epidermal Growth Factor-Stimulated Actin Nucleation in Breast Cancer Cells," Journal of Biological Chemistry, Feb. 11, 2000, vol. 275, No. 6, pp. 3741-3744.
S. Dao et al., "Antisense Inhibition of PIK3CA Reverses Cancer Phenotype," Proceedings of the Annual meeting of the American Association for Cancer Research, Mar. 1, 2002, vol. 43, p. 602.
P. Rodriguez-Viciana et al., "Activation of Phosphoinositide 3-Kinase by Interaction with RAS and by Point Mutation," EMBO Journal, Jan. 1, 1996, vol. 15, No. 10, pp. 2442-2451.
L. Shayesteh et al., *Nat Genet* 21, 99-102 (Jan. 1999).
GenBank NM_006218. *Homo sapiens* phos . . . [gi:5453891].
I. Vivanco, C. L. Sawyers, *Nat Rev Cancer* 2, 489-501 (Jul. 2002).
Y. Lu et al., "Targeting PI3K-AKT Pathway for Cancer Therapy," *Rev Clin Exp Hematol*, Jun. 2003, vol. 7.2.
"Single Nucleotide Polymorphism," NCBI from Locus PIK3CA.
GenBank NP_006209.phosphoinositide . . . [gi:5453892].
"Phosphatidylinositol3-Kinae, catalytic, Alpha; PIK3CA," Online Mendelian Inheritance in Man, 171834.
"PIK3CA: Phosphoinositide-3-Kinase, Catalytic, Alpha Polypeptide," NCBI, LocusLink, LocusID: 5290.
Y. Samuels et al., "High Frequency of Mutations of the PIK3CA gene in Human Cancers," Science, pp. 1-13, Mar. 1, 2004, Vol. XXX.

* cited by examiner

*Primary Examiner* — Laura B Goddard
(74) *Attorney, Agent, or Firm* — Banner & Witcoff, Ltd.

(57) ABSTRACT

Phosphatidylinositol 3-kinases (PI3Ks) are known to be important regulators of signaling pathways. To determine whether PI3Ks are genetically altered in cancers, we analyzed the sequences of the P13K gene family and discovered that one family member, PIK3CA, is frequently mutated in cancers of the colon and other organs. The majority of mutations clustered near two positions within the P13K helical or kinase domains. PIK3CA represents one of the most highly mutated oncogenes yet identified in human cancers and is useful as a diagnostic and therapeutic target.

63 Claims, 3 Drawing Sheets

SEQUENCE LISTING

```
<160> NUMBER OF SEQ ID NOS: 487

<210> SEQ ID NO 1
<211> LENGTH: 3412
<212> TYPE: DNA
<213> ORGANISM: Homo sapiens

<400> SEQUENCE: 1
atgcctccaa gaccatcatc aggtgaactg tggggcatcc acttgatgcc cccaagaatc      60
ctagtggaat gtttactacc aaatggaatg atagtgactt tagaatgcct ccgtgaggct     120
acattagtaa ctataaagca tgaactattt aaagaagcaa gaaaataccc tctccatcaa     180
cttcttcaag atgaatcttc ttacattttc gtaagtgtta cccaagaagc agaaagggaa     240
gaattttttg atgaaacaag acgactttgt gatcttcggc tttttcaacc attttttaaaa    300 gtaattgaac cagtaggcaa ccgtgaagaa aagatcctca atcgagaaat tggttttgct     360
atcggcatgc cagtgtgcga atttgatatg gttaaagatc ctgaagtaca ggacttccga     420
agaaatattc ttaatgtttg taaagaagct gtggatctta gggatcttaa ttcacctcat     480
agtagagcaa tgtatgtcta tccgccacat gtagaatctt caccagagct gccaaagcac     540
atatataata aattggatag aggccaaata atagtggtga tttgggtaat agtttctcca     600
aataatgaca agcagaagta tactctgaaa atcaaccatg actgtgtgcc agaacaagta     660
```

```
attgctgaag caatcaggaa aaaaactaga agtatgttgc tatcatctga acaattaaaa    720
ctctgtgttt tagaatatca gggcaagtac attttaaaag tgtgtggatg tgatgaatac    780
ttcctagaaa aatatcctct gagtcagtat aagtatataa aagctgtat aatgcttggg    840
aggatgccca atttgaagat gatggctaaa gaaagccttt attctcaact gccaatggac    900
tgttttacaa tgccatctta ttccagacgc atttccacag ctacaccata tatgaatgga    960
gaaacatcta caaaatccct ttgggttata aatagagcac tcagaataaa aattctttgt   1020
gcaacctacg tgaatctaaa tattcgagac attgacaaga tttatgttcg aacaggtatc   1080
taccatggag gagaacccct tatgtgacaat gtgaacactc aaagagtacc ttgttccaat   1140
cccaggtgga atgaatggct gaattatgat atatacattc ctgatcttcc tcgtgctgct   1200
cgactttgcc tttccatttg ctctgttaaa ggccgaaagg gtgctaaaga ggaacactgt   1260
ccattggcat ggggaaatat aaacttgttt gattacacag acactctagt atctggaaaa   1320
atggctttga atctttggcc agtacctcat ggattagaag atttgctgaa ccctattggt   1380
gttactggat caaatccaaa taagaaaact ccatgcttag agttggagtt tgactggttc   1440
agcagtgtgg taaagttccc agatatgtca gtgattgaag agcatgccaa ttggtctgta   1500
tcccgagaag caggatttag ctattcccac gcaggactga gtaacagact agctagagac   1560
aatgaattaa gggaaaatga caaagaacag ctcaaagcaa tttctacacg agatcctctc   1620
tctgaaatca ctgagcagga gaaagatttt ctatggagtc acagacacta ttgtgtaact   1680
atccccgaaa ttctacccaa attgcttctg tctgttaaat ggaattctag agatgaagta   1740
gcccagatgt attgcttggt aaaagattgg cctccaatca aacctgaaca ggctatggaa   1800
cttctggact gtaattaccc agatcctatg gttcgaggtt ttgctgttcg gtgcttggaa   1860
aaatatttaa cagatgacaa actttctcag tatttaattc agctagtaca ggtcctaaaa   1920
tatgaacaat atttggataa cttgcttgtg agattttac tgaagaaagc attgactaat   1980
caaaggattg ggcacttttt cttttggcat ttaaaatctg agatgcacaa taaaacagtt   2040
agccagaggt ttggcctgct tttggagtcc tattgtcgtg catgtgggat gtatttgaag   2100
cacctgaata ggcaagtcga ggcaatggaa aagctcatta acttaactga cattctcaaa   2160
caggagagga aggatgaaac acaaaaggta cagatgaagt tttagtttga gcaaatgagg   2220
cgaccagatt tcatggatgc cctacagggc ttgctgtctc ctctaaaccc tgctcatcaa   2280
ctaggaaacc tcaggcttaa agagtgtcga attatgtctt ctgcaaaaag gccactgtgg   2340
ttgaattggg agaacccaga catcatgtca gagttactgt tcagaacaa tgagatcatc   2400
tttaaaaatg gggatgattt acggcaagat atgctaacac ttcaaattat tcgtattatg   2460
gaaaatatct ggcaaaatca aggtcttgat cttcgaatgt taccttatgg ttgtctgtca   2520
atcggtgact gtgtgggact tattgaggtg gtgcgaaatt ctcacactat tatgcaaatt   2580
cagtgcaaag gcggcttgaa aggtgcactg cagttcaaca gccacacact acatcagtgg   2640
ctcaaagaca agaacaaagg agaaatatat gatgcagcca ttgacctgtt tacacgttca   2700
tgtgctggat actgtgtagc taccttcatt ttgggaattg agatcgtca caatagtaac   2760
atcatggtga agacgatgg acaactgttt catatagatt ttggacactt tttggatcac   2820
aagaagaaaa aatttggtta taaacgagaa cgtgtgccat ttgttttgac acaggatttc   2880
ttaatagtga ttagtaaagg agcccaagaa tgcacaaaga caagagaatt tgagaggttt   2940
caggagatgt gttacaaggc ttatctagct attgacagc atgccaatct cttcataaat   3000
cttttctcaa tgatgcttgg ctctggaatg ccagaactac aatctttga tgacattgca   3060
```

| | |
|---|---|
| tacattcgaa agaccctagc cttagataaa actgagcaag aggctttgga gtatttcatg | 3120 |
| aaacaaatga atgatgcaca tcatggtggc tggacaacaa aaatggattg gatcttccac | 3180 |
| acaattaaac agcatgcatt gaactgaaag ataactgaga aatgaaagc tcactctgga | 3240 |
| ttccacactg cactgttaat aactctcagc aggcaaagac cgattgcata ggaattgcac | 3300 |
| aatccatgaa cagcattaga tttacagcaa gaacagaaat aaaatactat ataatttaaa | 3360 |
| taatgtaaac gcaaacaggg tttgatagca cttaaactag ttcatttcaa aa | 3412 |

<210> SEQ ID NO 2
<211> LENGTH: 3424
<212> TYPE: DNA
<213> ORGANISM: Homo sapiens

<400> SEQUENCE: 2

| | |
|---|---|
| aggatcagaa caatgcctcc aagaccatca tcaggtgaac tgtggggcat ccacttgatg | 60 |
| cccccaagaa tcctagtgga atgtttacta ccaaatggaa tgatagtgac tttagaatgc | 120 |
| ctccgtgagg ctacattagt aactataaag catgaactat ttaaagaagc aagaaaatac | 180 |
| cctctccatc aacttcttca agatgaatct tcttacattt tcgtaagtgt tacccaagaa | 240 |
| gcagaaaggg aagaattttt tgatgaaaca agacgacttt gtgatcttcg cttttttcaa | 300 |
| ccatttttaa aagtaattga accagtaggc aaccgtgaag aaaagatcct caatcgagaa | 360 |
| attggttttg ctatcggcat gccagtgtgc gaatttgata tggttaaaga tcctgaagta | 420 |
| caggacttcc gaagaaatat tcttaatgtt tgtaaagaag ctgtggatct tagggatctt | 480 |
| aattcacctc atagtagagc aatgtatgtc tatccgccac atgtagaatc ttcaccagag | 540 |
| ctgccaaagc acatatataa taaattggat agaggccaaa aatagtggt gatttgggta | 600 |
| atagtttctc caaataatga caagcagaag tatactctga aaatcaacca tgactgtgtg | 660 |
| ccagaacaag taattgctga agcaatcagg aaaaaaacta gaagtatgtt gctatcatct | 720 |
| gaacaattaa aactctgtgt tttagaatat cagggcaagt acattttaaa agtgtgtgga | 780 |
| tgtgatgaat acttcctaga aaatatcct ctgagtcagt ataagtatat aagaagctgt | 840 |
| ataatgcttg ggaggatgcc caatttgaag atgatggcta agaaaagcct ttattctcaa | 900 |
| ctgccaatgg actgttttac aatgccatct tattccagac gcatttccac agctacacca | 960 |
| tatatgaatg gagaaacatc tacaaaatcc ctttgggtta aaatagagc actcagaata | 1020 |
| aaaattcttt gtgcaaccta cgtgaatcta atattcgag acattgacaa gatttatgtt | 1080 |
| cgaacaggta tctaccatgg aggagaaccc ttatgtgaca atgtgaacac tcaaagagta | 1140 |
| ccttgttcca atcccaggtg gaatgaatgg ctgaattatg atatatacat tcctgatctt | 1200 |
| cctcgtgctc tcgactttg ccttccatt tgctctgtta aaggccgaaa gggtgctaaa | 1260 |
| gaggaacact gtccattggc atggggaaat ataaacttgt tgattacac agacactcta | 1320 |
| gtatctggaa aaatggcttt gaatctttgg ccagtacctc atggattaga agatttgctg | 1380 |
| aaccctattg gtgttactgg atcaaatcca aataaagaaa ctccatgctt agagttggag | 1440 |
| tttgactggt tcagcagtgt ggtaaagttc ccagatatgt cagtgattga agagcatgcc | 1500 |
| aattggtctg tatcccgaga agcaggattt agctattccc acgcaggact gagtaacaga | 1560 |
| ctagctagag acaatgaatt aagggaaaat gacaaagaac agctcaaagc aatttctaca | 1620 |
| cgagatcctc tctctgaaat cactgagcag gagaaagatt ttctatggag tcacagacac | 1680 |
| tattgtgtaa ctatccccga aattctaccc aaattgcttc tgtctgttaa atggaattct | 1740 |
| agagatgaag tagcccagat gtattgcttg gtaaaagatt ggcctccaat caaacctgaa | 1800 |

```
caggctatgg aacttctgga ctgtaattac ccagatccta tggttcgagg ttttgctgtt   1860
cggtgcttgg aaaatatttt aacagatgac aaactttctc agtatttaat tcagctagta   1920
caggtcctaa aatatgaaca atatttggat aacttgcttg tgagattttt actgaagaaa   1980
gcattgacta atcaaaggat tgggcacttt ttcttttggc atttaaaatc tgagatgcac   2040
aataaaacag ttagccagag gtttggcctg cttttggagt cctattgtcg tgcatgtggg   2100
atgtatttga agcacctgaa taggcaagtc gaggcaatgg aaaagctcat taacttaact   2160
gacattctca aacaggagag gaaggatgaa acacaaaagg tacagatgaa gtttttagtt   2220
gagcaaatga ggcgaccaga tttcatggat gccctacagg gcttgctgtc cctctaaac    2280
cctgctcatc aactaggaaa cctcaggctt aaagagtgtc gaattatgtc ttctgcaaaa   2340
aggccactgt ggttgaattg ggagaaccca gacatcatgt cagagttact gtttcagaac   2400
aatgagatca tctttaaaaa tggggatgat ttacggcaag atatgctaac acttcaaatt   2460
attcgtatta tggaaaatat ctggcaaaat caaggtcttg atcttcgaat gttaccttat   2520
ggttgtctgt caatcggtga ctgtgtggga cttattgagg tggtgcgaaa ttctcacact   2580
attatgcaaa ttcagtgcaa aggcggcttg aaaggtgcac tgcagttcaa cagccacaca   2640
ctacatcagt ggctcaaaga caagaacaaa ggagaaatat atgatgcagc cattgacctg   2700
tttacacgtt catgtgctgg atactgtgta gctaccttca tttttgggaat ggagatcgt    2760
cacaatagta acatcatggt gaaagacgat ggacaactgt ttcatataga ttttggacac   2820
tttttggatc acaagaagaa aaaatttggt tataaacgag aacgtgtgcc atttgttttg   2880
acacaggatt tcttaatagt gattagtaaa ggagcccaag aatgcacaaa gacaagagaa   2940
tttgagaggt tcaggagat gtgttacaag gcttatctag ctattcgaca gcatgccaat    3000
ctcttcataa atcttttctc aatgatgctt ggctctggaa tgccagaact acaatctttt   3060
gatgacattg catacattcg aaagacccta gccttagata aaactgagca agaggctttg   3120
gagtatttca tgaaacaaat gaatgatgca catcatggtg gctggacaac aaaaatggat   3180
tggatcttcc acacaattaa acagcatgca ttgaactgaa agataactga gaaaatgaaa   3240
gctcactctg gattccacac tgcactgtta ataactctca gcaggcaaag accgattgca   3300
taggaattgc acaatccatg aacagcatta gatttacagc aagaacagaa ataaaatact   3360
atataattta ataatgtaa acgcaaacag ggtttgatag cacttaaact agttcatttc    3420
aaaa                                                                3424
```

<210> SEQ ID NO 3
<211> LENGTH: 1068
<212> TYPE: PRT
<213> ORGANISM: Homo sapiens

<400> SEQUENCE: 3

```
Met Pro Pro Arg Pro Ser Ser Gly Glu Leu Trp Gly Ile His Leu Met
1               5                   10                  15

Pro Pro Arg Ile Leu Val Glu Cys Leu Leu Pro Asn Gly Met Ile Val
            20                  25                  30

Thr Leu Glu Cys Leu Arg Glu Ala Thr Leu Val Thr Ile Lys His Glu
        35                  40                  45

Leu Phe Lys Glu Ala Arg Lys Tyr Pro Leu His Gln Leu Leu Gln Asp
    50                  55                  60

Glu Ser Ser Tyr Ile Phe Val Ser Val Thr Gln Glu Ala Glu Arg Glu
65                  70                  75                  80

Glu Phe Phe Asp Glu Thr Arg Arg Leu Cys Asp Leu Arg Leu Phe Gln
```

```
                 85                    90                    95
Pro Phe Leu Lys Val Ile Glu Pro Val Gly Asn Arg Glu Lys Ile
                100                   105                   110
Leu Asn Arg Glu Ile Gly Phe Ala Ile Gly Met Pro Val Cys Glu Phe
                115                   120                   125
Asp Met Val Lys Asp Pro Glu Val Gln Asp Phe Arg Arg Asn Ile Leu
                130                   135                   140
Asn Val Cys Lys Glu Ala Val Asp Leu Arg Asp Leu Asn Ser Pro His
145                 150                   155                   160
Ser Arg Ala Met Tyr Val Tyr Pro Pro His Val Glu Ser Ser Pro Glu
                    165                   170                   175
Leu Pro Lys His Ile Tyr Asn Lys Leu Asp Arg Gly Gln Ile Ile Val
                180                   185                   190
Val Ile Trp Val Ile Val Ser Pro Asn Asn Asp Lys Gln Lys Tyr Thr
                195                   200                   205
Leu Lys Ile Asn His Asp Cys Val Pro Glu Gln Val Ile Ala Glu Ala
210                 215                   220
Ile Arg Lys Lys Thr Arg Ser Met Leu Leu Ser Ser Glu Gln Leu Lys
225                 230                   235                   240
Leu Cys Val Leu Glu Tyr Gln Gly Lys Tyr Ile Leu Lys Val Cys Gly
                    245                   250                   255
Cys Asp Glu Tyr Phe Leu Glu Lys Tyr Pro Leu Ser Gln Tyr Lys Tyr
                    260                   265                   270
Ile Arg Ser Cys Ile Met Leu Gly Arg Met Pro Asn Leu Lys Met Met
                    275                   280                   285
Ala Lys Glu Ser Leu Tyr Ser Gln Leu Pro Met Asp Cys Phe Thr Met
                290                   295                   300
Pro Ser Tyr Ser Arg Arg Ile Ser Thr Ala Thr Pro Tyr Met Asn Gly
305                 310                   315                   320
Glu Thr Ser Thr Lys Ser Leu Trp Val Ile Asn Arg Ala Leu Arg Ile
                    325                   330                   335
Lys Ile Leu Cys Ala Thr Tyr Val Asn Leu Asn Ile Arg Asp Ile Asp
                340                   345                   350
Lys Ile Tyr Val Arg Thr Gly Ile Tyr His Gly Gly Glu Pro Leu Cys
                355                   360                   365
Asp Asn Val Asn Thr Gln Arg Val Pro Cys Ser Asn Pro Arg Trp Asn
                370                   375                   380
Glu Trp Leu Asn Tyr Asp Ile Tyr Ile Pro Asp Leu Pro Arg Ala Ala
385                 390                   395                   400
Arg Leu Cys Leu Ser Ile Cys Ser Val Lys Gly Arg Lys Gly Ala Lys
                    405                   410                   415
Glu Glu His Cys Pro Leu Ala Trp Gly Asn Ile Asn Leu Phe Asp Tyr
                420                   425                   430
Thr Asp Thr Leu Val Ser Gly Lys Met Ala Leu Asn Leu Trp Pro Val
                435                   440                   445
Pro His Gly Leu Glu Asp Leu Leu Asn Pro Ile Gly Val Thr Gly Ser
                450                   455                   460
Asn Pro Asn Lys Glu Thr Pro Cys Leu Glu Leu Glu Phe Asp Trp Phe
465                 470                   475                   480
Ser Ser Val Val Lys Phe Pro Asp Met Ser Val Ile Glu Glu His Ala
                    485                   490                   495
Asn Trp Ser Val Ser Arg Glu Ala Gly Phe Ser Tyr Ser His Ala Gly
                500                   505                   510
```

```
Leu Ser Asn Arg Leu Ala Arg Asp Asn Glu Leu Arg Glu Asn Asp Lys
        515                 520                 525

Glu Gln Leu Lys Ala Ile Ser Thr Arg Asp Pro Leu Ser Glu Ile Thr
530                 535                 540

Glu Gln Glu Lys Asp Phe Leu Trp Ser His Arg His Tyr Cys Val Thr
545                 550                 555                 560

Ile Pro Glu Ile Leu Pro Lys Leu Leu Leu Ser Val Lys Trp Asn Ser
                565                 570                 575

Arg Asp Glu Val Ala Gln Met Tyr Cys Leu Val Lys Asp Trp Pro Pro
            580                 585                 590

Ile Lys Pro Glu Gln Ala Met Glu Leu Leu Asp Cys Asn Tyr Pro Asp
        595                 600                 605

Pro Met Val Arg Gly Phe Ala Val Arg Cys Leu Glu Lys Tyr Leu Thr
610                 615                 620

Asp Asp Lys Leu Ser Gln Tyr Leu Ile Gln Leu Val Gln Val Leu Lys
625                 630                 635                 640

Tyr Glu Gln Tyr Leu Asp Asn Leu Leu Val Arg Phe Leu Leu Lys Lys
                645                 650                 655

Ala Leu Thr Asn Gln Arg Ile Gly His Phe Phe Phe Trp His Leu Lys
            660                 665                 670

Ser Glu Met His Asn Lys Thr Val Ser Gln Arg Phe Gly Leu Leu Leu
        675                 680                 685

Glu Ser Tyr Cys Arg Ala Cys Gly Met Tyr Leu Lys His Leu Asn Arg
690                 695                 700

Gln Val Glu Ala Met Glu Lys Leu Ile Asn Leu Thr Asp Ile Leu Lys
705                 710                 715                 720

Gln Glu Arg Lys Asp Glu Thr Gln Lys Val Gln Met Lys Phe Leu Val
                725                 730                 735

Glu Gln Met Arg Arg Pro Asp Phe Met Asp Ala Leu Gln Gly Leu Leu
            740                 745                 750

Ser Pro Leu Asn Pro Ala His Gln Leu Gly Asn Leu Arg Leu Lys Glu
        755                 760                 765

Cys Arg Ile Met Ser Ser Ala Lys Arg Pro Leu Trp Leu Asn Trp Glu
770                 775                 780

Asn Pro Asp Ile Met Ser Glu Leu Leu Phe Gln Asn Asn Glu Ile Ile
785                 790                 795                 800

Phe Lys Asn Gly Asp Asp Leu Arg Gln Asp Met Leu Thr Leu Gln Ile
                805                 810                 815

Ile Arg Ile Met Glu Asn Ile Trp Gln Asn Gln Gly Leu Asp Leu Arg
            820                 825                 830

Met Leu Pro Tyr Gly Cys Leu Ser Ile Gly Asp Cys Val Gly Leu Ile
        835                 840                 845

Glu Val Val Arg Asn Ser His Thr Ile Met Gln Ile Gln Cys Lys Gly
850                 855                 860

Gly Leu Lys Gly Ala Leu Gln Phe Asn Ser His Thr Leu His Gln Trp
865                 870                 875                 880

Leu Lys Asp Lys Asn Lys Gly Glu Ile Tyr Asp Ala Ala Ile Asp Leu
                885                 890                 895

Phe Thr Arg Ser Cys Ala Gly Tyr Cys Val Ala Thr Phe Ile Leu Gly
            900                 905                 910

Ile Gly Asp Arg His Asn Ser Asn Ile Met Val Lys Asp Asp Gly Gln
        915                 920                 925

Leu Phe His Ile Asp Phe Gly His Phe Leu Asp His Lys Lys Lys Lys
930                 935                 940
```

Phe Gly Tyr Lys Arg Glu Arg Val Pro Phe Val Leu Thr Gln Asp Phe
945                 950                 955                 960

Leu Ile Val Ile Ser Lys Gly Ala Gln Glu Cys Thr Lys Thr Arg Glu
            965                 970                 975

Phe Glu Arg Phe Gln Glu Met Cys Tyr Lys Ala Tyr Leu Ala Ile Arg
        980                 985                 990

Gln His Ala Asn Leu Phe Ile Asn Leu Phe Ser Met Met Leu Gly Ser
            995                 1000                1005

Gly Met Pro Glu Leu Gln Ser Phe Asp Asp Ile Ala Tyr Ile Arg Lys
        1010                1015                1020

Thr Leu Ala Leu Asp Lys Thr Glu Gln Glu Ala Leu Glu Tyr Phe Met
1025                1030                1035                1040

Lys Gln Met Asn Asp Ala His His Gly Gly Trp Thr Thr Lys Met Asp
                1045                1050                1055

Trp Ile Phe His Thr Ile Lys Gln His Ala Leu Asn
            1060                1065

<210> SEQ ID NO 4
<211> LENGTH: 125
<212> TYPE: DNA
<213> ORGANISM: Homo sapiens

<400> SEQUENCE: 4
agtaacagac tagctagaga caatgaatta agggaaaatg acaagaaca gctcaaagca      60 atttctacac gagatcctct ctctgaaatc actgagcagg agaaagattt tctatggagt     120
cacag                                                                 125

<210> SEQ ID NO 5
<211> LENGTH: 1186
<212> TYPE: DNA
<213> ORGANISM: Homo sapiens

<400> SEQUENCE: 5
gtttcaggag atgtgttaca aggcttatct agctattcga cagcatgcca atctcttcat      60
aaatcttttc tcaatgatgc ttggctctgg aatgccagaa ctacaatctt ttgatgacat     120
tgcatacatt cgaaagaccc tagccttaga taaaactgag caagaggctt ggagtatttt     180
catgaaacaa atgaatgatg cacatcatgg tggctggaca caaaaatgg attggatctt     240 ccacacaatt aaacagcatg cattgaactg aaaagataac tgagaaaatg aaagctcact     300
ctggattcca cactgcactg ttaataactc tcagcaggca aagaccgatt gcataggaat     360
tgcacaatcc atgaacagca ttagaattta cagcaagaac agaaataaaa tactatataa     420
tttaaataat gtaaacgcaa acagggtttg atagcactta aactagttca tttcaaaatt     480
aagctttaga ataatgcgca atttcatgtt atgccttaag tccaaaaagg taaactttga     540
agattgtttg tatctttttt taaaaaacaa aacaaaacaa aaatcccaa aatatataga     600 aatgatggag aaggaaaaag tgatggtttt ttttgtcttg caaatgttct atgttttgaa     660
atgtggacac aacaaaggct gttattgcat taggtgtaag taaactggag tttatgttaa     720
attacattga ttggaaaaga atgaaaattt cttatttttc cattgctgtt caatttatag     780
tttgaagtgg ttttttgact gcttgtttaa tgaagaaaaa tgcttggggt ggaagggact     840
cttgagattt caccagagac ttttctcttt taataaatca aacctttga tgatttgagg     900 ttttatctgc agttttggaa gcagtcacaa atgagacctg ttataaggtg gtatttttt      960 ttttcttctg gacagtattt aaaggatctt attcttattt cccagggaaa ttctgggctc    1020

-continued

```
ccacaaagta aaaaaaaaaa aaaatcatag aaaaagaatg agcaggaata gttcttattc    1080
cagaattgta cagtattcac cttaagttga tttttttttct ccttctgcaa ttgaactgaa   1140 tacattttc atgcatgttt tccagaaaat agaagtatta atgtta                    1186
```

<210> SEQ ID NO 6
<211> LENGTH: 20
<212> TYPE: DNA
<213> ORGANISM: Homo sapiens

<400> SEQUENCE: 6
ttccagcctg ggtaacaaag                                                  20

<210> SEQ ID NO 7
<211> LENGTH: 20
<212> TYPE: DNA
<213> ORGANISM: Homo sapiens

<400> SEQUENCE: 7
cctgacctca ggtgttctgc                                                  20

<210> SEQ ID NO 8
<211> LENGTH: 21
<212> TYPE: DNA
<213> ORGANISM: Homo sapiens

<400> SEQUENCE: 8
tgcacattct gcacgtgtat c                                                21

<210> SEQ ID NO 9
<211> LENGTH: 24
<212> TYPE: DNA
<213> ORGANISM: Homo sapiens

<400> SEQUENCE: 9
tcccagtttg tatgctattg agag                                             24

<210> SEQ ID NO 10
<211> LENGTH: 21
<212> TYPE: DNA
<213> ORGANISM: Homo sapiens

<400> SEQUENCE: 10
tggaaattca aaagtgtgtg g                                                21

<210> SEQ ID NO 11
<211> LENGTH: 23
<212> TYPE: DNA
<213> ORGANISM: Homo sapiens

<400> SEQUENCE: 11
cactaatgaa cccctcaaga ctg                                              23

<210> SEQ ID NO 12
<211> LENGTH: 20
<212> TYPE: DNA
<213> ORGANISM: Homo sapiens

<400> SEQUENCE: 12
tccttggcaa agtgacaatc                                                  20

<210> SEQ ID NO 13
<211> LENGTH: 23

```
<212> TYPE: DNA
<213> ORGANISM: Homo sapiens

<400> SEQUENCE: 13
ctctcacata caacaccatc tcc                                             23

<210> SEQ ID NO 14
<211> LENGTH: 23
<212> TYPE: DNA
<213> ORGANISM: Homo sapiens

<400> SEQUENCE: 14
atgtatctca ttgaaaaccc aac                                             23

<210> SEQ ID NO 15
<211> LENGTH: 20
<212> TYPE: DNA
<213> ORGANISM: Homo sapiens

<400> SEQUENCE: 15
tcccaaagtg ctgggattac                                                 20

<210> SEQ ID NO 16
<211> LENGTH: 26
<212> TYPE: DNA
<213> ORGANISM: Homo sapiens

<400> SEQUENCE: 16
cctatgacat aaatgccagt acaaac                                          26

<210> SEQ ID NO 17
<211> LENGTH: 24
<212> TYPE: DNA
<213> ORGANISM: Homo sapiens

<400> SEQUENCE: 17
tcttttgttc agtcagcatc tctc                                            24

<210> SEQ ID NO 18
<211> LENGTH: 24
<212> TYPE: DNA
<213> ORGANISM: Homo sapiens

<400> SEQUENCE: 18
ttgagaattc agatgagaaa ccag                                            24

<210> SEQ ID NO 19
<211> LENGTH: 20
<212> TYPE: DNA
<213> ORGANISM: Homo sapiens

<400> SEQUENCE: 19
gaaggccact ctcaaacctg                                                 20

<210> SEQ ID NO 20
<211> LENGTH: 20
<212> TYPE: DNA
<213> ORGANISM: Homo sapiens

<400> SEQUENCE: 20
tcaaggcttg catttcattg                                                 20

<210> SEQ ID NO 21
<211> LENGTH: 20
```

```
<212> TYPE: DNA
<213> ORGANISM: Homo sapiens

<400> SEQUENCE: 21
ttccacactc caaagaatgc                                                 20

<210> SEQ ID NO 22
<211> LENGTH: 21
<212> TYPE: DNA
<213> ORGANISM: Homo sapiens

<400> SEQUENCE: 22
aattgcaatc ctcttggtag c                                               21

<210> SEQ ID NO 23
<211> LENGTH: 19
<212> TYPE: DNA
<213> ORGANISM: Homo sapiens

<400> SEQUENCE: 23
gccaagacca agcaactcc                                                  19

<210> SEQ ID NO 24
<211> LENGTH: 20
<212> TYPE: DNA
<213> ORGANISM: Homo sapiens

<400> SEQUENCE: 24
ataaacgacc gctggcctac                                                 20

<210> SEQ ID NO 25
<211> LENGTH: 20
<212> TYPE: DNA
<213> ORGANISM: Homo sapiens

<400> SEQUENCE: 25
gtacatccgg ggacacaatg                                                 20

<210> SEQ ID NO 26
<211> LENGTH: 20
<212> TYPE: DNA
<213> ORGANISM: Homo sapiens

<400> SEQUENCE: 26
accgggttct tccagctaag                                                 20

<210> SEQ ID NO 27
<211> LENGTH: 20
<212> TYPE: DNA
<213> ORGANISM: Homo sapiens

<400> SEQUENCE: 27
caatgcgtgc gttaaatctg                                                 20

<210> SEQ ID NO 28
<211> LENGTH: 18
<212> TYPE: DNA
<213> ORGANISM: Homo sapiens

<400> SEQUENCE: 28
cccaatgcca cggactac                                                   18

<210> SEQ ID NO 29
<211> LENGTH: 20
```

```
<212> TYPE: DNA
<213> ORGANISM: Homo sapiens

<400> SEQUENCE: 29
atccagctgg ctctgatagg                                              20

<210> SEQ ID NO 30
<211> LENGTH: 20
<212> TYPE: DNA
<213> ORGANISM: Homo sapiens

<400> SEQUENCE: 30
ctggtgctga aactcgactg                                              20

<210> SEQ ID NO 31
<211> LENGTH: 20
<212> TYPE: DNA
<213> ORGANISM: Homo sapiens

<400> SEQUENCE: 31
gtctcgttct ctccctcacg                                              20

<210> SEQ ID NO 32
<211> LENGTH: 18
<212> TYPE: DNA
<213> ORGANISM: Homo sapiens

<400> SEQUENCE: 32
cacaacctcg cccagttc                                                18

<210> SEQ ID NO 33
<211> LENGTH: 21
<212> TYPE: DNA
<213> ORGANISM: Homo sapiens

<400> SEQUENCE: 33
agcatcaccc tcagagcata c                                            21

<210> SEQ ID NO 34
<211> LENGTH: 22
<212> TYPE: DNA
<213> ORGANISM: Homo sapiens

<400> SEQUENCE: 34
tgccatacct cttaggcact tc                                           22

<210> SEQ ID NO 35
<211> LENGTH: 20
<212> TYPE: DNA
<213> ORGANISM: Homo sapiens

<400> SEQUENCE: 35
cgacagagca agattccatc                                              20

<210> SEQ ID NO 36
<211> LENGTH: 20
<212> TYPE: DNA
<213> ORGANISM: Homo sapiens

<400> SEQUENCE: 36
agattgccat ctgaggaagg                                              20

<210> SEQ ID NO 37
<211> LENGTH: 20
```

```
<212> TYPE: DNA
<213> ORGANISM: Homo sapiens

<400> SEQUENCE: 37
gcatggagag gaagtgaacc                                                 20

<210> SEQ ID NO 38
<211> LENGTH: 22
<212> TYPE: DNA
<213> ORGANISM: Homo sapiens

<400> SEQUENCE: 38
tggccagaga gtttgattta tg                                              22

<210> SEQ ID NO 39
<211> LENGTH: 20
<212> TYPE: DNA
<213> ORGANISM: Homo sapiens

<400> SEQUENCE: 39
ccctcaatct cttgggaaag                                                 20

<210> SEQ ID NO 40
<211> LENGTH: 21
<212> TYPE: DNA
<213> ORGANISM: Homo sapiens

<400> SEQUENCE: 40
tggtttcttc tcatggacag g                                               21

<210> SEQ ID NO 41
<211> LENGTH: 20
<212> TYPE: DNA
<213> ORGANISM: Homo sapiens

<400> SEQUENCE: 41
gggtgtccac acttctcagg                                                 20

<210> SEQ ID NO 42
<211> LENGTH: 20
<212> TYPE: DNA
<213> ORGANISM: Homo sapiens

<400> SEQUENCE: 42
ccggaagaaa caatgagcag                                                 20

<210> SEQ ID NO 43
<211> LENGTH: 20
<212> TYPE: DNA
<213> ORGANISM: Homo sapiens

<400> SEQUENCE: 43
ggtgtgagct gagtgagcag                                                 20

<210> SEQ ID NO 44
<211> LENGTH: 20
<212> TYPE: DNA
<213> ORGANISM: Homo sapiens

<400> SEQUENCE: 44
gtgggaatga ccttcctttc                                                 20

<210> SEQ ID NO 45
<211> LENGTH: 21
```

-continued

<210> SEQ ID NO 45
<211> LENGTH: 21
<212> TYPE: DNA
<213> ORGANISM: Homo sapiens

<400> SEQUENCE: 45
ggatgaacag gcagatgtga g                                      21

<210> SEQ ID NO 46
<211> LENGTH: 20
<212> TYPE: DNA
<213> ORGANISM: Homo sapiens

<400> SEQUENCE: 46
agccccttct atccagtgtg                                         20

<210> SEQ ID NO 47
<211> LENGTH: 20
<212> TYPE: DNA
<213> ORGANISM: Homo sapiens

<400> SEQUENCE: 47
tgcccacagc atctgtctac                                         20

<210> SEQ ID NO 48
<211> LENGTH: 20
<212> TYPE: DNA
<213> ORGANISM: Homo sapiens

<400> SEQUENCE: 48
attgtgtgcc agtcatttgc                                         20

<210> SEQ ID NO 49
<211> LENGTH: 21
<212> TYPE: DNA
<213> ORGANISM: Homo sapiens

<400> SEQUENCE: 49
ttccacatta agcatgagca c                                       21

<210> SEQ ID NO 50
<211> LENGTH: 27
<212> TYPE: DNA
<213> ORGANISM: Homo sapiens

<400> SEQUENCE: 50
gacagtcatt cttttcatag gtcatag                                 27

<210> SEQ ID NO 51
<211> LENGTH: 23
<212> TYPE: DNA
<213> ORGANISM: Homo sapiens

<400> SEQUENCE: 51
ccacatagta agccttcaat gac                                     23

<210> SEQ ID NO 52
<211> LENGTH: 23
<212> TYPE: DNA
<213> ORGANISM: Homo sapiens

<400> SEQUENCE: 52
tgaaaaatgt tcctttattc ttg                                     23

<210> SEQ ID NO 53
<211> LENGTH: 21

```
<212> TYPE: DNA
<213> ORGANISM: Homo sapiens

<400> SEQUENCE: 53
tctgagaaca ttccctgatc c                                       21

<210> SEQ ID NO 54
<211> LENGTH: 23
<212> TYPE: DNA
<213> ORGANISM: Homo sapiens

<400> SEQUENCE: 54
tcagctctct aatcctgaac tgc                                     23

<210> SEQ ID NO 55
<211> LENGTH: 23
<212> TYPE: DNA
<213> ORGANISM: Homo sapiens

<400> SEQUENCE: 55
agcagagaag aaacatatac cat                                     23

<210> SEQ ID NO 56
<211> LENGTH: 20
<212> TYPE: DNA
<213> ORGANISM: Homo sapiens

<400> SEQUENCE: 56
cattttggga aaggaggttc                                         20

<210> SEQ ID NO 57
<211> LENGTH: 20
<212> TYPE: DNA
<213> ORGANISM: Homo sapiens

<400> SEQUENCE: 57
attacaggcg tgagccactg                                         20

<210> SEQ ID NO 58
<211> LENGTH: 20
<212> TYPE: DNA
<213> ORGANISM: Homo sapiens

<400> SEQUENCE: 58
tttggcactg tcttcagagg                                         20

<210> SEQ ID NO 59
<211> LENGTH: 20
<212> TYPE: DNA
<213> ORGANISM: Homo sapiens

<400> SEQUENCE: 59
agagggaaca cccttttcctg                                        20

<210> SEQ ID NO 60
<211> LENGTH: 20
<212> TYPE: DNA
<213> ORGANISM: Homo sapiens

<400> SEQUENCE: 60
tatagcgttg tgcccatgac                                         20

<210> SEQ ID NO 61
<211> LENGTH: 26
```

```
<212> TYPE: DNA
<213> ORGANISM: Homo sapiens

<400> SEQUENCE: 61
tcctgcctct tgctattttt tcaatg                                        26

<210> SEQ ID NO 62
<211> LENGTH: 22
<212> TYPE: DNA
<213> ORGANISM: Homo sapiens

<400> SEQUENCE: 62
ttgcctcaga gagatcatca ag                                            22

<210> SEQ ID NO 63
<211> LENGTH: 20
<212> TYPE: DNA
<213> ORGANISM: Homo sapiens

<400> SEQUENCE: 63 tagggcgct aatcgtactg                                                20

<210> SEQ ID NO 64
<211> LENGTH: 21
<212> TYPE: DNA
<213> ORGANISM: Homo sapiens

<400> SEQUENCE: 64
tctgatatgc atcagccact g                                             21

<210> SEQ ID NO 65
<211> LENGTH: 20
<212> TYPE: DNA
<213> ORGANISM: Homo sapiens

<400> SEQUENCE: 65
tgatttcaag ggaagcagag                                               20

<210> SEQ ID NO 66
<211> LENGTH: 20
<212> TYPE: DNA
<213> ORGANISM: Homo sapiens

<400> SEQUENCE: 66
tgtagaaagc aaggctgctc                                               20

<210> SEQ ID NO 67
<211> LENGTH: 20
<212> TYPE: DNA
<213> ORGANISM: Homo sapiens

<400> SEQUENCE: 67
accccaaagt catccaagtg                                               20

<210> SEQ ID NO 68
<211> LENGTH: 20
<212> TYPE: DNA
<213> ORGANISM: Homo sapiens

<400> SEQUENCE: 68
aaaggctcca gttgatggac                                               20

<210> SEQ ID NO 69
<211> LENGTH: 24
```

```
<212> TYPE: DNA
<213> ORGANISM: Homo sapiens

<400> SEQUENCE: 69
ccattaaaac cactctaagt cagg                                          24

<210> SEQ ID NO 70
<211> LENGTH: 21
<212> TYPE: DNA
<213> ORGANISM: Homo sapiens

<400> SEQUENCE: 70
aagcctcctc cagaaaagaa g                                             21

<210> SEQ ID NO 71
<211> LENGTH: 20
<212> TYPE: DNA
<213> ORGANISM: Homo sapiens

<400> SEQUENCE: 71
ccctcctgtc cactgagatg                                               20

<210> SEQ ID NO 72
<211> LENGTH: 20
<212> TYPE: DNA
<213> ORGANISM: Homo sapiens

<400> SEQUENCE: 72
tctcaagctg cctcacaatg                                               20

<210> SEQ ID NO 73
<211> LENGTH: 20
<212> TYPE: DNA
<213> ORGANISM: Homo sapiens

<400> SEQUENCE: 73
aaagacattg ccatgcaaac                                               20

<210> SEQ ID NO 74
<211> LENGTH: 20
<212> TYPE: DNA
<213> ORGANISM: Homo sapiens

<400> SEQUENCE: 74
ttgttgggct ccaaataaac                                               20

<210> SEQ ID NO 75
<211> LENGTH: 20
<212> TYPE: DNA
<213> ORGANISM: Homo sapiens

<400> SEQUENCE: 75
ccctggagtg cttacatgag                                               20

<210> SEQ ID NO 76
<211> LENGTH: 27
<212> TYPE: DNA
<213> ORGANISM: Homo sapiens

<400> SEQUENCE: 76
gactttataa acactcgaca ttagagc                                       27

<210> SEQ ID NO 77
<211> LENGTH: 20
```

```
<212> TYPE: DNA
<213> ORGANISM: Homo sapiens

<400> SEQUENCE: 77
atgatgacct ctggcaggac                                          20

<210> SEQ ID NO 78
<211> LENGTH: 20
<212> TYPE: DNA
<213> ORGANISM: Homo sapiens

<400> SEQUENCE: 78
gaatcaaccg tcagcgtgtc                                          20

<210> SEQ ID NO 79
<211> LENGTH: 21
<212> TYPE: DNA
<213> ORGANISM: Homo sapiens

<400> SEQUENCE: 79
ctggcaccgg ggaaaacaga g                                        21

<210> SEQ ID NO 80
<211> LENGTH: 22
<212> TYPE: DNA
<213> ORGANISM: Homo sapiens

<400> SEQUENCE: 80
tggacatcga ctacaagtct gg                                       22

<210> SEQ ID NO 81
<211> LENGTH: 20
<212> TYPE: DNA
<213> ORGANISM: Homo sapiens

<400> SEQUENCE: 81
tccttggggt tttgaagaag                                          20

<210> SEQ ID NO 82
<211> LENGTH: 20
<212> TYPE: DNA
<213> ORGANISM: Homo sapiens

<400> SEQUENCE: 82
aaggccttcc agactcttgc                                          20

<210> SEQ ID NO 83
<211> LENGTH: 21
<212> TYPE: DNA
<213> ORGANISM: Homo sapiens

<400> SEQUENCE: 83
cctctttgtt tttccctacc g                                        21

<210> SEQ ID NO 84
<211> LENGTH: 20
<212> TYPE: DNA
<213> ORGANISM: Homo sapiens

<400> SEQUENCE: 84
cttccacagt gggggtacag                                          20

<210> SEQ ID NO 85
<211> LENGTH: 23
```

```
<212> TYPE: DNA
<213> ORGANISM: Homo sapiens

<400> SEQUENCE: 85
gacacaacgg caacattatg ctg                                              23

<210> SEQ ID NO 86
<211> LENGTH: 23
<212> TYPE: DNA
<213> ORGANISM: Homo sapiens

<400> SEQUENCE: 86
cattccaaag catctggttt tac                                              23

<210> SEQ ID NO 87
<211> LENGTH: 22
<212> TYPE: DNA
<213> ORGANISM: Homo sapiens

<400> SEQUENCE: 87
ttgtgaggaa cgtgtgatta gg                                               22

<210> SEQ ID NO 88
<211> LENGTH: 19
<212> TYPE: DNA
<213> ORGANISM: Homo sapiens

<400> SEQUENCE: 88
ctgggcaaca gagcaagac                                                   19

<210> SEQ ID NO 89
<211> LENGTH: 20
<212> TYPE: DNA
<213> ORGANISM: Homo sapiens

<400> SEQUENCE: 89
tcccttctcc tttggctatg                                                  20

<210> SEQ ID NO 90
<211> LENGTH: 20
<212> TYPE: DNA
<213> ORGANISM: Homo sapiens

<400> SEQUENCE: 90
atagcaccac tgccttccag                                                  20

<210> SEQ ID NO 91
<211> LENGTH: 19
<212> TYPE: DNA
<213> ORGANISM: Homo sapiens

<400> SEQUENCE: 91
tgcagaagtg gaggtggag                                                   19

<210> SEQ ID NO 92
<211> LENGTH: 20
<212> TYPE: DNA
<213> ORGANISM: Homo sapiens

<400> SEQUENCE: 92
aacccaagct gcttcctttc                                                  20

<210> SEQ ID NO 93
<211> LENGTH: 20
```

<212> TYPE: DNA
<213> ORGANISM: Homo sapiens

<400> SEQUENCE: 93
agtcctgccc tgattccttc                                          20

<210> SEQ ID NO 94
<211> LENGTH: 20
<212> TYPE: DNA
<213> ORGANISM: Homo sapiens

<400> SEQUENCE: 94
cccacccact tattcctgag                                          20

<210> SEQ ID NO 95
<211> LENGTH: 22
<212> TYPE: DNA
<213> ORGANISM: Homo sapiens

<400> SEQUENCE: 95
tttccccttt agggtaggta gg                                       22

<210> SEQ ID NO 96
<211> LENGTH: 21
<212> TYPE: DNA
<213> ORGANISM: Homo sapiens

<400> SEQUENCE: 96
cggacataga ggaaggattg c                                        21

<210> SEQ ID NO 97
<211> LENGTH: 20
<212> TYPE: DNA
<213> ORGANISM: Homo sapiens

<400> SEQUENCE: 97
tggccaaact tttcaaatcc                                          20

<210> SEQ ID NO 98
<211> LENGTH: 20
<212> TYPE: DNA
<213> ORGANISM: Homo sapiens

<400> SEQUENCE: 98
tgggagagct cagggaatac                                          20

<210> SEQ ID NO 99
<211> LENGTH: 20
<212> TYPE: DNA
<213> ORGANISM: Homo sapiens

<400> SEQUENCE: 99
tcccaaagtg ctgggattac                                          20

<210> SEQ ID NO 100
<211> LENGTH: 20
<212> TYPE: DNA
<213> ORGANISM: Homo sapiens

<400> SEQUENCE: 100
ttggctgcca tgactaacac                                          20

<210> SEQ ID NO 101
<211> LENGTH: 20

<212> TYPE: DNA
<213> ORGANISM: Homo sapiens

<400> SEQUENCE: 101
gctctcagtg tgcctcatgg                                                  20

<210> SEQ ID NO 102
<211> LENGTH: 18
<212> TYPE: DNA
<213> ORGANISM: Homo sapiens

<400> SEQUENCE: 102
aagaaacacc ccggttcc                                                    18

<210> SEQ ID NO 103
<211> LENGTH: 27
<212> TYPE: DNA
<213> ORGANISM: Homo sapiens

<400> SEQUENCE: 103
aaatttagtt gagtaatgag agaatgc                                          27

<210> SEQ ID NO 104
<211> LENGTH: 20
<212> TYPE: DNA
<213> ORGANISM: Homo sapiens

<400> SEQUENCE: 104
gtaaaattgg ccctgctttg                                                  20

<210> SEQ ID NO 105
<211> LENGTH: 20
<212> TYPE: DNA
<213> ORGANISM: Homo sapiens

<400> SEQUENCE: 105
cataaccaca tgcagcaacc                                                  20

<210> SEQ ID NO 106
<211> LENGTH: 20
<212> TYPE: DNA
<213> ORGANISM: Homo sapiens

<400> SEQUENCE: 106
aattggcctt ggagacagac                                                  20

<210> SEQ ID NO 107
<211> LENGTH: 21
<212> TYPE: DNA
<213> ORGANISM: Homo sapiens

<400> SEQUENCE: 107
ttcatgtgag caggtatgct g                                                21

<210> SEQ ID NO 108
<211> LENGTH: 20
<212> TYPE: DNA
<213> ORGANISM: Homo sapiens

<400> SEQUENCE: 108
ttgtgtacga ccctctggtg                                                  20

<210> SEQ ID NO 109
<211> LENGTH: 20

```
<212> TYPE: DNA
<213> ORGANISM: Homo sapiens

<400> SEQUENCE: 109
tttgtacagt ggaggcaacg                                              20

<210> SEQ ID NO 110
<211> LENGTH: 23
<212> TYPE: DNA
<213> ORGANISM: Homo sapiens

<400> SEQUENCE: 110
cagctggtta tgtgtgttta tgg                                          23

<210> SEQ ID NO 111
<211> LENGTH: 20
<212> TYPE: DNA
<213> ORGANISM: Homo sapiens

<400> SEQUENCE: 111
tgtcctcatg gttgcttttc                                              20

<210> SEQ ID NO 112
<211> LENGTH: 20
<212> TYPE: DNA
<213> ORGANISM: Homo sapiens

<400> SEQUENCE: 112
cagggacatg ctatccaaag                                              20

<210> SEQ ID NO 113
<211> LENGTH: 21
<212> TYPE: DNA
<213> ORGANISM: Homo sapiens

<400> SEQUENCE: 113
tggtggaact tgtgttttc c                                             21

<210> SEQ ID NO 114
<211> LENGTH: 20
<212> TYPE: DNA
<213> ORGANISM: Homo sapiens

<400> SEQUENCE: 114
tcatacggtt ttggcagctc                                              20

<210> SEQ ID NO 115
<211> LENGTH: 20
<212> TYPE: DNA
<213> ORGANISM: Homo sapiens

<400> SEQUENCE: 115
acagagggag aagggctcag                                              20

<210> SEQ ID NO 116
<211> LENGTH: 20
<212> TYPE: DNA
<213> ORGANISM: Homo sapiens

<400> SEQUENCE: 116
tgggacaatt ttcgcagaag                                              20

<210> SEQ ID NO 117
<211> LENGTH: 20
```

<212> TYPE: DNA
<213> ORGANISM: Homo sapiens

<400> SEQUENCE: 117
atgaagcatg ctgcctgatg                                           20

<210> SEQ ID NO 118
<211> LENGTH: 19
<212> TYPE: DNA
<213> ORGANISM: Homo sapiens

<400> SEQUENCE: 118
gggggccttt agaaggaag                                            19

<210> SEQ ID NO 119
<211> LENGTH: 21
<212> TYPE: DNA
<213> ORGANISM: Homo sapiens

<400> SEQUENCE: 119
tggagttcct gagaaatgag c                                         21

<210> SEQ ID NO 120
<211> LENGTH: 20
<212> TYPE: DNA
<213> ORGANISM: Homo sapiens

<400> SEQUENCE: 120
agagggaaca ccctttcctg                                           20

<210> SEQ ID NO 121
<211> LENGTH: 22
<212> TYPE: DNA
<213> ORGANISM: Homo sapiens

<400> SEQUENCE: 121
catgatgttg gagcttacat gc                                        22

<210> SEQ ID NO 122
<211> LENGTH: 20
<212> TYPE: DNA
<213> ORGANISM: Homo sapiens

<400> SEQUENCE: 122
cgggattgga gacagacatc                                           20

<210> SEQ ID NO 123
<211> LENGTH: 20
<212> TYPE: DNA
<213> ORGANISM: Homo sapiens

<400> SEQUENCE: 123
catcatggta cacgcactcc                                           20

<210> SEQ ID NO 124
<211> LENGTH: 21
<212> TYPE: DNA
<213> ORGANISM: Homo sapiens

<400> SEQUENCE: 124
ctcaatcaga gcctgaacca c                                         21

<210> SEQ ID NO 125
<211> LENGTH: 21

```
<212> TYPE: DNA
<213> ORGANISM: Homo sapiens

<400> SEQUENCE: 125
cccggcctaa agttgtagtt c                                              21

<210> SEQ ID NO 126
<211> LENGTH: 20
<212> TYPE: DNA
<213> ORGANISM: Homo sapiens

<400> SEQUENCE: 126
tgggagactg tcaagaggtg                                                20

<210> SEQ ID NO 127
<211> LENGTH: 20
<212> TYPE: DNA
<213> ORGANISM: Homo sapiens

<400> SEQUENCE: 127
ttcctccaag gagctttgtc                                                20

<210> SEQ ID NO 128
<211> LENGTH: 21
<212> TYPE: DNA
<213> ORGANISM: Homo sapiens

<400> SEQUENCE: 128
ttccctgtcc agactgttag c                                              21

<210> SEQ ID NO 129
<211> LENGTH: 22
<212> TYPE: DNA
<213> ORGANISM: Homo sapiens

<400> SEQUENCE: 129
ccggttatgc acatcattta ag                                             22

<210> SEQ ID NO 130
<211> LENGTH: 21
<212> TYPE: DNA
<213> ORGANISM: Homo sapiens

<400> SEQUENCE: 130
gcagccagag cagaagtaaa c                                              21

<210> SEQ ID NO 131
<211> LENGTH: 21
<212> TYPE: DNA
<213> ORGANISM: Homo sapiens

<400> SEQUENCE: 131
tctaatgaaa gcccactctg c                                              21

<210> SEQ ID NO 132
<211> LENGTH: 22
<212> TYPE: DNA
<213> ORGANISM: Homo sapiens

<400> SEQUENCE: 132
aagtgtgcat gatgtttgtt cc                                             22

<210> SEQ ID NO 133
<211> LENGTH: 20
```

```
<212> TYPE: DNA
<213> ORGANISM: Homo sapiens

<400> SEQUENCE: 133
gatgaccaag aatgcaaacg                                               20

<210> SEQ ID NO 134
<211> LENGTH: 23
<212> TYPE: DNA
<213> ORGANISM: Homo sapiens

<400> SEQUENCE: 134
atcatcttta agaacgggga tgg                                           23

<210> SEQ ID NO 135
<211> LENGTH: 18
<212> TYPE: DNA
<213> ORGANISM: Homo sapiens

<400> SEQUENCE: 135
cctcagatgc tggtgccg                                                 18

<210> SEQ ID NO 136
<211> LENGTH: 20
<212> TYPE: DNA
<213> ORGANISM: Homo sapiens

<400> SEQUENCE: 136
tcttcatgcc ttggctctgg                                               20

<210> SEQ ID NO 137
<211> LENGTH: 20
<212> TYPE: DNA
<213> ORGANISM: Homo sapiens

<400> SEQUENCE: 137
tccgagagag tgggcaggta                                               20

<210> SEQ ID NO 138
<211> LENGTH: 19
<212> TYPE: DNA
<213> ORGANISM: Homo sapiens

<400> SEQUENCE: 138
gggcaggttt gtgggtcat                                                19

<210> SEQ ID NO 139
<211> LENGTH: 18
<212> TYPE: DNA
<213> ORGANISM: Homo sapiens

<400> SEQUENCE: 139
ggaactgggg gctctggg                                                 18

<210> SEQ ID NO 140
<211> LENGTH: 22
<212> TYPE: DNA
<213> ORGANISM: Homo sapiens

<400> SEQUENCE: 140
gtttctgctt tgggacaacc at                                            22

<210> SEQ ID NO 141
<211> LENGTH: 19
```

```
<212> TYPE: DNA
<213> ORGANISM: Homo sapiens

<400> SEQUENCE: 141
ctccacgacc atcatcagg                                              19

<210> SEQ ID NO 142
<211> LENGTH: 20
<212> TYPE: DNA
<213> ORGANISM: Homo sapiens

<400> SEQUENCE: 142 cccccctccat caacttcttc                                            20

<210> SEQ ID NO 143
<211> LENGTH: 26
<212> TYPE: DNA
<213> ORGANISM: Homo sapiens

<400> SEQUENCE: 143
tcatcaaaaa tttgttttaa cctagc                                      26

<210> SEQ ID NO 144
<211> LENGTH: 24
<212> TYPE: DNA
<213> ORGANISM: Homo sapiens

<400> SEQUENCE: 144
ttctgaacgt ttgtaaagaa gctg                                        24

<210> SEQ ID NO 145
<211> LENGTH: 21
<212> TYPE: DNA
<213> ORGANISM: Homo sapiens

<400> SEQUENCE: 145
gcagcccgct cagatataaa c                                           21

<210> SEQ ID NO 146
<211> LENGTH: 23
<212> TYPE: DNA
<213> ORGANISM: Homo sapiens

<400> SEQUENCE: 146
tctgaaaatc aaccatgact gtg                                         23

<210> SEQ ID NO 147
<211> LENGTH: 22
<212> TYPE: DNA
<213> ORGANISM: Homo sapiens

<400> SEQUENCE: 147
tcttgtgctt caacgtaaat cc                                          22

<210> SEQ ID NO 148
<211> LENGTH: 20
<212> TYPE: DNA
<213> ORGANISM: Homo sapiens

<400> SEQUENCE: 148
tctcaactgc caatggactg                                             20

<210> SEQ ID NO 149
<211> LENGTH: 20
```

<212> TYPE: DNA
<213> ORGANISM: Homo sapiens

<400> SEQUENCE: 149
tagtggatga aggcagcaac                                              20

<210> SEQ ID NO 150
<211> LENGTH: 20
<212> TYPE: DNA
<213> ORGANISM: Homo sapiens

<400> SEQUENCE: 150
tgccttttcc aatcaatctc                                              20

<210> SEQ ID NO 151
<211> LENGTH: 20
<212> TYPE: DNA
<213> ORGANISM: Homo sapiens

<400> SEQUENCE: 151
ggggaaaaag gaaagaatgg                                              20

<210> SEQ ID NO 152
<211> LENGTH: 20
<212> TYPE: DNA
<213> ORGANISM: Homo sapiens

<400> SEQUENCE: 152
tttgctgaac cctattggtg                                              20

<210> SEQ ID NO 153
<211> LENGTH: 22
<212> TYPE: DNA
<213> ORGANISM: Homo sapiens

<400> SEQUENCE: 153
gattggttct ttcctgtctc tg                                           22

<210> SEQ ID NO 154
<211> LENGTH: 20
<212> TYPE: DNA
<213> ORGANISM: Homo sapiens

<400> SEQUENCE: 154
accttttgaa cagcatgcaa                                              20

<210> SEQ ID NO 155
<211> LENGTH: 27
<212> TYPE: DNA
<213> ORGANISM: Homo sapiens

<400> SEQUENCE: 155
aaaacaccct taacattatt tccatag                                      27

<210> SEQ ID NO 156
<211> LENGTH: 28
<212> TYPE: DNA
<213> ORGANISM: Homo sapiens

<400> SEQUENCE: 156
tttattctag atccatacaa cttcctttt                                    28

<210> SEQ ID NO 157
<211> LENGTH: 21

```
<212> TYPE: DNA
<213> ORGANISM: Homo sapiens

<400> SEQUENCE: 157
ctgaaactca tggtggtttt g                                              21

<210> SEQ ID NO 158
<211> LENGTH: 21
<212> TYPE: DNA
<213> ORGANISM: Homo sapiens

<400> SEQUENCE: 158
gagtgttgct gctctgtgtt g                                              21

<210> SEQ ID NO 159
<211> LENGTH: 25
<212> TYPE: DNA
<213> ORGANISM: Homo sapiens

<400> SEQUENCE: 159
ggattcctaa ataaaaattg aggtg                                          25

<210> SEQ ID NO 160
<211> LENGTH: 23
<212> TYPE: DNA
<213> ORGANISM: Homo sapiens

<400> SEQUENCE: 160
ttgctttcct gaagtttctt ttg                                            23

<210> SEQ ID NO 161
<211> LENGTH: 20
<212> TYPE: DNA
<213> ORGANISM: Homo sapiens

<400> SEQUENCE: 161
ggggaaaggc agtaaaggtc                                                20

<210> SEQ ID NO 162
<211> LENGTH: 23
<212> TYPE: DNA
<213> ORGANISM: Homo sapiens

<400> SEQUENCE: 162
tccttattcg ttgtcagtga ttg                                            23

<210> SEQ ID NO 163
<211> LENGTH: 20
<212> TYPE: DNA
<213> ORGANISM: Homo sapiens

<400> SEQUENCE: 163
catggtgaaa gacgatggac                                                20

<210> SEQ ID NO 164
<211> LENGTH: 21
<212> TYPE: DNA
<213> ORGANISM: Homo sapiens

<400> SEQUENCE: 164
tggggtaaag ggaatcaaaa g                                              21

<210> SEQ ID NO 165
<211> LENGTH: 20
```

```
<212> TYPE: DNA
<213> ORGANISM: Homo sapiens

<400> SEQUENCE: 165
ttgcatacat tcgaaagacc                                          20

<210> SEQ ID NO 166
<211> LENGTH: 20
<212> TYPE: DNA
<213> ORGANISM: Homo sapiens

<400> SEQUENCE: 166
cgtcagaaca agaccctgtg                                          20

<210> SEQ ID NO 167
<211> LENGTH: 22
<212> TYPE: DNA
<213> ORGANISM: Homo sapiens

<400> SEQUENCE: 167
cccggccact aagttatttt tc                                       22

<210> SEQ ID NO 168
<211> LENGTH: 20
<212> TYPE: DNA
<213> ORGANISM: Homo sapiens

<400> SEQUENCE: 168
ctgccattaa atgcgtcttg                                          20

<210> SEQ ID NO 169
<211> LENGTH: 20
<212> TYPE: DNA
<213> ORGANISM: Homo sapiens

<400> SEQUENCE: 169
ctttgggcct ttttcattcc                                          20

<210> SEQ ID NO 170
<211> LENGTH: 20
<212> TYPE: DNA
<213> ORGANISM: Homo sapiens

<400> SEQUENCE: 170
tgtctggctt atttcacacg                                          20

<210> SEQ ID NO 171
<211> LENGTH: 24
<212> TYPE: DNA
<213> ORGANISM: Homo sapiens

<400> SEQUENCE: 171
aacttttgac agcctactat gtgc                                     24

<210> SEQ ID NO 172
<211> LENGTH: 23
<212> TYPE: DNA
<213> ORGANISM: Homo sapiens

<400> SEQUENCE: 172
gaccattcat gaaagaaaca agc                                      23

<210> SEQ ID NO 173
<211> LENGTH: 23
```

```
<212> TYPE: DNA
<213> ORGANISM: Homo sapiens

<400> SEQUENCE: 173
ccatgtaccg gtaacaaaag aag                                          23

<210> SEQ ID NO 174
<211> LENGTH: 23
<212> TYPE: DNA
<213> ORGANISM: Homo sapiens

<400> SEQUENCE: 174
tgagctttct aggatcgtac ctg                                          23

<210> SEQ ID NO 175
<211> LENGTH: 20
<212> TYPE: DNA
<213> ORGANISM: Homo sapiens

<400> SEQUENCE: 175
gcaggaaggt ccaacttgtc                                              20

<210> SEQ ID NO 176
<211> LENGTH: 20
<212> TYPE: DNA
<213> ORGANISM: Homo sapiens

<400> SEQUENCE: 176
atcttcaact gcgaacatgc                                              20

<210> SEQ ID NO 177
<211> LENGTH: 26
<212> TYPE: DNA
<213> ORGANISM: Homo sapiens

<400> SEQUENCE: 177
aagcatcaat gactacttta atcaac                                       26

<210> SEQ ID NO 178
<211> LENGTH: 20
<212> TYPE: DNA
<213> ORGANISM: Homo sapiens

<400> SEQUENCE: 178
tcccaaagtg ctgggattac                                              20

<210> SEQ ID NO 179
<211> LENGTH: 20
<212> TYPE: DNA
<213> ORGANISM: Homo sapiens

<400> SEQUENCE: 179
ttgttgcctt tgtcattttg                                              20

<210> SEQ ID NO 180
<211> LENGTH: 20
<212> TYPE: DNA
<213> ORGANISM: Homo sapiens

<400> SEQUENCE: 180
atgtgactgt gggcaggaac                                              20

<210> SEQ ID NO 181
<211> LENGTH: 20
```

```
<212> TYPE: DNA
<213> ORGANISM: Homo sapiens

<400> SEQUENCE: 181
gctggtgaga tgtcaaaacg                                               20

<210> SEQ ID NO 182
<211> LENGTH: 26
<212> TYPE: DNA
<213> ORGANISM: Homo sapiens

<400> SEQUENCE: 182
tcaacatatt acttcctcca gaactc                                        26

<210> SEQ ID NO 183
<211> LENGTH: 20
<212> TYPE: DNA
<213> ORGANISM: Homo sapiens

<400> SEQUENCE: 183
ttctcccatg tcagggaatc                                               20

<210> SEQ ID NO 184
<211> LENGTH: 20
<212> TYPE: DNA
<213> ORGANISM: Homo sapiens

<400> SEQUENCE: 184
gaccctcaaa ggctaacgtg                                               20

<210> SEQ ID NO 185
<211> LENGTH: 21
<212> TYPE: DNA
<213> ORGANISM: Homo sapiens

<400> SEQUENCE: 185
tccctggtca gcacagacta c                                             21

<210> SEQ ID NO 186
<211> LENGTH: 21
<212> TYPE: DNA
<213> ORGANISM: Homo sapiens

<400> SEQUENCE: 186
agctgtctca tttccaccat c                                             21

<210> SEQ ID NO 187
<211> LENGTH: 20
<212> TYPE: DNA
<213> ORGANISM: Homo sapiens

<400> SEQUENCE: 187
cgcgtcgttt atgtcaaatc                                               20

<210> SEQ ID NO 188
<211> LENGTH: 20
<212> TYPE: DNA
<213> ORGANISM: Homo sapiens

<400> SEQUENCE: 188
cgcgtcgttt atgtcaaatc                                               20

<210> SEQ ID NO 189
<211> LENGTH: 20
```

```
<212> TYPE: DNA
<213> ORGANISM: Homo sapiens

<400> SEQUENCE: 189
cataacacac aggggtgctg                                               20

<210> SEQ ID NO 190
<211> LENGTH: 18
<212> TYPE: DNA
<213> ORGANISM: Homo sapiens

<400> SEQUENCE: 190
gaactgggcg aggttgtg                                                 18

<210> SEQ ID NO 191
<211> LENGTH: 20
<212> TYPE: DNA
<213> ORGANISM: Homo sapiens

<400> SEQUENCE: 191
tccctttctt acacgcaaac                                               20

<210> SEQ ID NO 192
<211> LENGTH: 21
<212> TYPE: DNA
<213> ORGANISM: Homo sapiens

<400> SEQUENCE: 192
cagttccgcc tgtacattca c                                             21

<210> SEQ ID NO 193
<211> LENGTH: 19
<212> TYPE: DNA
<213> ORGANISM: Homo sapiens

<400> SEQUENCE: 193
agcgctcctg ctttcagtc                                                19

<210> SEQ ID NO 194
<211> LENGTH: 20
<212> TYPE: DNA
<213> ORGANISM: Homo sapiens

<400> SEQUENCE: 194
gtcttggcgc agatcatcac                                               20

<210> SEQ ID NO 195
<211> LENGTH: 21
<212> TYPE: DNA
<213> ORGANISM: Homo sapiens

<400> SEQUENCE: 195
ttttgtcacc agttgaaatg c                                             21

<210> SEQ ID NO 196
<211> LENGTH: 20
<212> TYPE: DNA
<213> ORGANISM: Homo sapiens

<400> SEQUENCE: 196
gactgggaaa aagcatgagc                                               20

<210> SEQ ID NO 197
<211> LENGTH: 25
```

```
<212> TYPE: DNA
<213> ORGANISM: Homo sapiens

<400> SEQUENCE: 197
cggtgatcat aatattgtca ttgtg                                         25

<210> SEQ ID NO 198
<211> LENGTH: 20
<212> TYPE: DNA
<213> ORGANISM: Homo sapiens

<400> SEQUENCE: 198
ggaagtgtgg gcttgtcttc                                               20

<210> SEQ ID NO 199
<211> LENGTH: 20
<212> TYPE: DNA
<213> ORGANISM: Homo sapiens

<400> SEQUENCE: 199
tgcacagtcc atcctttgtc                                               20

<210> SEQ ID NO 200
<211> LENGTH: 21
<212> TYPE: DNA
<213> ORGANISM: Homo sapiens

<400> SEQUENCE: 200
aatgccagct ttcacaatgt c                                             21

<210> SEQ ID NO 201
<211> LENGTH: 20
<212> TYPE: DNA
<213> ORGANISM: Homo sapiens

<400> SEQUENCE: 201
ggccaagacc acatggtaag                                               20

<210> SEQ ID NO 202
<211> LENGTH: 24
<212> TYPE: DNA
<213> ORGANISM: Homo sapiens

<400> SEQUENCE: 202
tcctacatta agacagcatg gaac                                          24

<210> SEQ ID NO 203
<211> LENGTH: 21
<212> TYPE: DNA
<213> ORGANISM: Homo sapiens

<400> SEQUENCE: 203 tgcctcccctt ttaaggctat c                                            21

<210> SEQ ID NO 204
<211> LENGTH: 20
<212> TYPE: DNA
<213> ORGANISM: Homo sapiens

<400> SEQUENCE: 204
aggtccttct gccaacaaag                                               20

<210> SEQ ID NO 205
<211> LENGTH: 20
```

```
<212> TYPE: DNA
<213> ORGANISM: Homo sapiens

<400> SEQUENCE: 205
cgtcttctct cctccaatgc                                                  20

<210> SEQ ID NO 206
<211> LENGTH: 20
<212> TYPE: DNA
<213> ORGANISM: Homo sapiens

<400> SEQUENCE: 206
ggtattcagt tggggctcag                                                  20

<210> SEQ ID NO 207
<211> LENGTH: 20
<212> TYPE: DNA
<213> ORGANISM: Homo sapiens

<400> SEQUENCE: 207
tgtatccacg tggtcagctc                                                  20

<210> SEQ ID NO 208
<211> LENGTH: 18
<212> TYPE: DNA
<213> ORGANISM: Homo sapiens

<400> SEQUENCE: 208
acaggacgct cggtcaac                                                    18

<210> SEQ ID NO 209
<211> LENGTH: 25
<212> TYPE: DNA
<213> ORGANISM: Homo sapiens

<400> SEQUENCE: 209
ttgccatcag tacaaatgag tttag                                            25

<210> SEQ ID NO 210
<211> LENGTH: 24
<212> TYPE: DNA
<213> ORGANISM: Homo sapiens

<400> SEQUENCE: 210
ttcctgcttt ttaagagtga tctg                                             24

<210> SEQ ID NO 211
<211> LENGTH: 20
<212> TYPE: DNA
<213> ORGANISM: Homo sapiens

<400> SEQUENCE: 211
aggaaggaag ggatggaaac                                                  20

<210> SEQ ID NO 212
<211> LENGTH: 18
<212> TYPE: DNA
<213> ORGANISM: Homo sapiens

<400> SEQUENCE: 212
agaaaccact catgaaaa                                                    18

<210> SEQ ID NO 213
<211> LENGTH: 22
```

```
<212> TYPE: DNA
<213> ORGANISM: Homo sapiens

<400> SEQUENCE: 213
cgcattacta catgatccac tg                                              22

<210> SEQ ID NO 214
<211> LENGTH: 21
<212> TYPE: DNA
<213> ORGANISM: Homo sapiens

<400> SEQUENCE: 214
tgtcacagaa agcatgagac c                                               21

<210> SEQ ID NO 215
<211> LENGTH: 29
<212> TYPE: DNA
<213> ORGANISM: Homo sapiens

<400> SEQUENCE: 215
agaaataact gtcaatatcc cagtatcac                                       29

<210> SEQ ID NO 216
<211> LENGTH: 27
<212> TYPE: DNA
<213> ORGANISM: Homo sapiens

<400> SEQUENCE: 216
tcattaaaca tttagtaatg tgtgctc                                         27

<210> SEQ ID NO 217
<211> LENGTH: 19
<212> TYPE: DNA
<213> ORGANISM: Homo sapiens

<400> SEQUENCE: 217
aggcaacagg gcaagactc                                                  19

<210> SEQ ID NO 218
<211> LENGTH: 21
<212> TYPE: DNA
<213> ORGANISM: Homo sapiens

<400> SEQUENCE: 218
cctgaaaggg agaataaaag g                                               21

<210> SEQ ID NO 219
<211> LENGTH: 21
<212> TYPE: DNA
<213> ORGANISM: Homo sapiens

<400> SEQUENCE: 219
cctgaaaggg agaataaaag g                                               21

<210> SEQ ID NO 220
<211> LENGTH: 20
<212> TYPE: DNA
<213> ORGANISM: Homo sapiens

<400> SEQUENCE: 220
tattgaccca gccagcagac                                                 20

<210> SEQ ID NO 221
<211> LENGTH: 22
```

```
<212> TYPE: DNA
<213> ORGANISM: Homo sapiens

<400> SEQUENCE: 221
tatattgaga ctcaaatatc ga                                              22

<210> SEQ ID NO 222
<211> LENGTH: 21
<212> TYPE: DNA
<213> ORGANISM: Homo sapiens

<400> SEQUENCE: 222
tgatgcatat cagagcgtga g                                               21

<210> SEQ ID NO 223
<211> LENGTH: 21
<212> TYPE: DNA
<213> ORGANISM: Homo sapiens

<400> SEQUENCE: 223
ttcaatgacc atgacaaaac g                                               21

<210> SEQ ID NO 224
<211> LENGTH: 21
<212> TYPE: DNA
<213> ORGANISM: Homo sapiens

<400> SEQUENCE: 224
ttcaatgacc atgacaaaac g                                               21

<210> SEQ ID NO 225
<211> LENGTH: 21
<212> TYPE: DNA
<213> ORGANISM: Homo sapiens

<400> SEQUENCE: 225
tggttttcaa gcagacaatc c                                               21

<210> SEQ ID NO 226
<211> LENGTH: 21
<212> TYPE: DNA
<213> ORGANISM: Homo sapiens

<400> SEQUENCE: 226
tcctcctcaa tgaaagcaga g                                               21

<210> SEQ ID NO 227
<211> LENGTH: 20
<212> TYPE: DNA
<213> ORGANISM: Homo sapiens

<400> SEQUENCE: 227
caatgtgatc ccaactggtc                                                 20

<210> SEQ ID NO 228
<211> LENGTH: 21
<212> TYPE: DNA
<213> ORGANISM: Homo sapiens

<400> SEQUENCE: 228
ttattgccaa ttggagtttg g                                               21

<210> SEQ ID NO 229
<211> LENGTH: 22
```

```
<212> TYPE: DNA
<213> ORGANISM: Homo sapiens

<400> SEQUENCE: 229
ttctgttggc ttatcatttt tg                                      22

<210> SEQ ID NO 230
<211> LENGTH: 23
<212> TYPE: DNA
<213> ORGANISM: Homo sapiens

<400> SEQUENCE: 230
cccagaaact aaataaaatg cag                                     23

<210> SEQ ID NO 231
<211> LENGTH: 25
<212> TYPE: DNA
<213> ORGANISM: Homo sapiens

<400> SEQUENCE: 231
aatcaaattt gttgcattaa aaatc                                   25

<210> SEQ ID NO 232
<211> LENGTH: 23
<212> TYPE: DNA
<213> ORGANISM: Homo sapiens

<400> SEQUENCE: 232
gttttctcat tcctttctct tcc                                     23

<210> SEQ ID NO 233
<211> LENGTH: 20
<212> TYPE: DNA
<213> ORGANISM: Homo sapiens

<400> SEQUENCE: 233
tttgggaaag ggaacacaag                                         20

<210> SEQ ID NO 234
<211> LENGTH: 22
<212> TYPE: DNA
<213> ORGANISM: Homo sapiens

<400> SEQUENCE: 234
gatttttcct tggaacatcc tc                                      22

<210> SEQ ID NO 235
<211> LENGTH: 20
<212> TYPE: DNA
<213> ORGANISM: Homo sapiens

<400> SEQUENCE: 235
cggggatcag atttgctatg                                         20

<210> SEQ ID NO 236
<211> LENGTH: 20
<212> TYPE: DNA
<213> ORGANISM: Homo sapiens

<400> SEQUENCE: 236
tagggggtca tcctcaggtc                                         20

<210> SEQ ID NO 237
<211> LENGTH: 20
```

```
<212> TYPE: DNA
<213> ORGANISM: Homo sapiens

<400> SEQUENCE: 237
gtcttcccct gctcaatcac                                            20

<210> SEQ ID NO 238
<211> LENGTH: 22
<212> TYPE: DNA
<213> ORGANISM: Homo sapiens

<400> SEQUENCE: 238
gacacgttgt gggccagcca gt                                         22

<210> SEQ ID NO 239
<211> LENGTH: 24
<212> TYPE: DNA
<213> ORGANISM: Homo sapiens

<400> SEQUENCE: 239
ctgccggtta tcttcggaca cgtt                                       24

<210> SEQ ID NO 240
<211> LENGTH: 20
<212> TYPE: DNA
<213> ORGANISM: Homo sapiens

<400> SEQUENCE: 240
tgagtgaggg cagacagatg                                            20

<210> SEQ ID NO 241
<211> LENGTH: 20
<212> TYPE: DNA
<213> ORGANISM: Homo sapiens

<400> SEQUENCE: 241
tggcacctga accatgtaag                                            20

<210> SEQ ID NO 242
<211> LENGTH: 20
<212> TYPE: DNA
<213> ORGANISM: Homo sapiens

<400> SEQUENCE: 242
cgtacatgcc gaagtctgtc                                            20

<210> SEQ ID NO 243
<211> LENGTH: 21
<212> TYPE: DNA
<213> ORGANISM: Homo sapiens

<400> SEQUENCE: 243
gccctggttt taacccttaa c                                          21

<210> SEQ ID NO 244
<211> LENGTH: 20
<212> TYPE: DNA
<213> ORGANISM: Homo sapiens

<400> SEQUENCE: 244
ccagctccag cttctgactc                                            20

<210> SEQ ID NO 245
<211> LENGTH: 20
```

```
<212> TYPE: DNA
<213> ORGANISM: Homo sapiens

<400> SEQUENCE: 245
ttgtgttttc ttggagacag                                              20

<210> SEQ ID NO 246
<211> LENGTH: 20
<212> TYPE: DNA
<213> ORGANISM: Homo sapiens

<400> SEQUENCE: 246
caatgagcat gggagagatg                                              20

<210> SEQ ID NO 247
<211> LENGTH: 21
<212> TYPE: DNA
<213> ORGANISM: Homo sapiens

<400> SEQUENCE: 247
tggagtttct gggactacag g                                            21

<210> SEQ ID NO 248
<211> LENGTH: 23
<212> TYPE: DNA
<213> ORGANISM: Homo sapiens

<400> SEQUENCE: 248
ccttcttcaa agctgattct ctc                                          23

<210> SEQ ID NO 249
<211> LENGTH: 20
<212> TYPE: DNA
<213> ORGANISM: Homo sapiens

<400> SEQUENCE: 249
cgctctacag ccaatcacag                                              20

<210> SEQ ID NO 250
<211> LENGTH: 20
<212> TYPE: DNA
<213> ORGANISM: Homo sapiens

<400> SEQUENCE: 250
tggcatcaca atcaataggg                                              20

<210> SEQ ID NO 251
<211> LENGTH: 20
<212> TYPE: DNA
<213> ORGANISM: Homo sapiens

<400> SEQUENCE: 251
ctccaagggg gttagagtcc                                              20

<210> SEQ ID NO 252
<211> LENGTH: 21
<212> TYPE: DNA
<213> ORGANISM: Homo sapiens

<400> SEQUENCE: 252
caggaaacca ggtcagaagt g                                            21

<210> SEQ ID NO 253
<211> LENGTH: 22
```

-continued

<212> TYPE: DNA
<213> ORGANISM: Homo sapiens

<400> SEQUENCE: 253
tttttgcaga aagggtctt ac                                            22

<210> SEQ ID NO 254
<211> LENGTH: 20
<212> TYPE: DNA
<213> ORGANISM: Homo sapiens

<400> SEQUENCE: 254
gcccacccca ctctagaaac                                              20

<210> SEQ ID NO 255
<211> LENGTH: 21
<212> TYPE: DNA
<213> ORGANISM: Homo sapiens

<400> SEQUENCE: 255
tggaaccttt tctgctcaaa g                                            21

<210> SEQ ID NO 256
<211> LENGTH: 18
<212> TYPE: DNA
<213> ORGANISM: Homo sapiens

<400> SEQUENCE: 256
agctgcatgg tgccaaag                                                18

<210> SEQ ID NO 257
<211> LENGTH: 20
<212> TYPE: DNA
<213> ORGANISM: Homo sapiens

<400> SEQUENCE: 257
ataacaatgg gcacatgcag                                              20

<210> SEQ ID NO 258
<211> LENGTH: 21
<212> TYPE: DNA
<213> ORGANISM: Homo sapiens

<400> SEQUENCE: 258
ggtcattctt ccatcagcaa g                                            21

<210> SEQ ID NO 259
<211> LENGTH: 21
<212> TYPE: DNA
<213> ORGANISM: Homo sapiens

<400> SEQUENCE: 259
cacacccaca ctcacacaaa g                                            21

<210> SEQ ID NO 260
<211> LENGTH: 20
<212> TYPE: DNA
<213> ORGANISM: Homo sapiens

<400> SEQUENCE: 260
ggcactgcag gctaataatg                                              20

<210> SEQ ID NO 261
<211> LENGTH: 22

```
<212> TYPE: DNA
<213> ORGANISM: Homo sapiens

<400> SEQUENCE: 261
gggacctcaa gtctttcct tc                                        22

<210> SEQ ID NO 262
<211> LENGTH: 22
<212> TYPE: DNA
<213> ORGANISM: Homo sapiens

<400> SEQUENCE: 262
gggacctcaa gtctttcct tc                                        22

<210> SEQ ID NO 263
<211> LENGTH: 20
<212> TYPE: DNA
<213> ORGANISM: Homo sapiens

<400> SEQUENCE: 263
ggaagggaag gaggacaaac                                          20

<210> SEQ ID NO 264
<211> LENGTH: 22
<212> TYPE: DNA
<213> ORGANISM: Homo sapiens

<400> SEQUENCE: 264
cgtctcaaac taccaagtct gg                                       22

<210> SEQ ID NO 265
<211> LENGTH: 20
<212> TYPE: DNA
<213> ORGANISM: Homo sapiens

<400> SEQUENCE: 265
cacccagtgc tgtttcaatg                                          20

<210> SEQ ID NO 266
<211> LENGTH: 20
<212> TYPE: DNA
<213> ORGANISM: Homo sapiens

<400> SEQUENCE: 266
cgccgcataa tgtgtaaaac                                          20

<210> SEQ ID NO 267
<211> LENGTH: 22
<212> TYPE: DNA
<213> ORGANISM: Homo sapiens

<400> SEQUENCE: 267
tgccatattt aactgccatt tc                                       22

<210> SEQ ID NO 268
<211> LENGTH: 22
<212> TYPE: DNA
<213> ORGANISM: Homo sapiens

<400> SEQUENCE: 268
tgccatattt aactgccatt tc                                       22

<210> SEQ ID NO 269
<211> LENGTH: 24
```

```
<212> TYPE: DNA
<213> ORGANISM: Homo sapiens

<400> SEQUENCE: 269
gcagtcactg agacagcttt tatc                                          24

<210> SEQ ID NO 270
<211> LENGTH: 20
<212> TYPE: DNA
<213> ORGANISM: Homo sapiens

<400> SEQUENCE: 270
taagcatagc ctcggagaac                                               20

<210> SEQ ID NO 271
<211> LENGTH: 24
<212> TYPE: DNA
<213> ORGANISM: Homo sapiens

<400> SEQUENCE: 271
ggaccattaa tagctacctt cctg                                          24

<210> SEQ ID NO 272
<211> LENGTH: 23
<212> TYPE: DNA
<213> ORGANISM: Homo sapiens

<400> SEQUENCE: 272
aggcaagaca acatatttga aag                                           23

<210> SEQ ID NO 273
<211> LENGTH: 23
<212> TYPE: DNA
<213> ORGANISM: Homo sapiens

<400> SEQUENCE: 273
aagggctatg tgtcattttg ttc                                           23

<210> SEQ ID NO 274
<211> LENGTH: 21
<212> TYPE: DNA
<213> ORGANISM: Homo sapiens

<400> SEQUENCE: 274
catcaagcaa gcaaacaaat g                                             21

<210> SEQ ID NO 275
<211> LENGTH: 19
<212> TYPE: DNA
<213> ORGANISM: Homo sapiens

<400> SEQUENCE: 275 aattcccca aaagcttcc                                                 19

<210> SEQ ID NO 276
<211> LENGTH: 20
<212> TYPE: DNA
<213> ORGANISM: Homo sapiens

<400> SEQUENCE: 276
ttccctcctg gctaagaacc                                               20

<210> SEQ ID NO 277
<211> LENGTH: 20
```

```
<212> TYPE: DNA
<213> ORGANISM: Homo sapiens

<400> SEQUENCE: 277
aaaagcagag ggaatcatcg                                              20

<210> SEQ ID NO 278
<211> LENGTH: 20
<212> TYPE: DNA
<213> ORGANISM: Homo sapiens

<400> SEQUENCE: 278
tcccattcat gacctggaag                                              20

<210> SEQ ID NO 279
<211> LENGTH: 20
<212> TYPE: DNA
<213> ORGANISM: Homo sapiens

<400> SEQUENCE: 279
ggcccgcttt aagagatcag                                              20

<210> SEQ ID NO 280
<211> LENGTH: 18
<212> TYPE: DNA
<213> ORGANISM: Homo sapiens

<400> SEQUENCE: 280
catgcccaaa gtcgatcc                                                18

<210> SEQ ID NO 281
<211> LENGTH: 20
<212> TYPE: DNA
<213> ORGANISM: Homo sapiens

<400> SEQUENCE: 281
acacatccat ggtgttggtg                                              20

<210> SEQ ID NO 282
<211> LENGTH: 20
<212> TYPE: DNA
<213> ORGANISM: Homo sapiens

<400> SEQUENCE: 282
tgccacagcc acatagtctc                                              20

<210> SEQ ID NO 283
<211> LENGTH: 22
<212> TYPE: DNA
<213> ORGANISM: Homo sapiens

<400> SEQUENCE: 283
ttctatctgc agactcccac ag                                           22

<210> SEQ ID NO 284
<211> LENGTH: 21
<212> TYPE: DNA
<213> ORGANISM: Homo sapiens

<400> SEQUENCE: 284
ggaaaagaaa gcaggagaag c                                            21

<210> SEQ ID NO 285
<211> LENGTH: 21
```

```
<212> TYPE: DNA
<213> ORGANISM: Homo sapiens

<400> SEQUENCE: 285
aaatggagaa aagcctggtt c                                       21

<210> SEQ ID NO 286
<211> LENGTH: 19
<212> TYPE: DNA
<213> ORGANISM: Homo sapiens

<400> SEQUENCE: 286
aagcaatcct cccaccttg                                          19

<210> SEQ ID NO 287
<211> LENGTH: 22
<212> TYPE: DNA
<213> ORGANISM: Homo sapiens

<400> SEQUENCE: 287
ccttcctttt tcactcacac ac                                      22

<210> SEQ ID NO 288
<211> LENGTH: 25
<212> TYPE: DNA
<213> ORGANISM: Homo sapiens

<400> SEQUENCE: 288
tgatttaata atgaagatgg gttgg                                   25

<210> SEQ ID NO 289
<211> LENGTH: 20
<212> TYPE: DNA
<213> ORGANISM: Homo sapiens

<400> SEQUENCE: 289
actcagtacc ccaggcagag                                         20

<210> SEQ ID NO 290
<211> LENGTH: 20
<212> TYPE: DNA
<213> ORGANISM: Homo sapiens

<400> SEQUENCE: 290
tcaaactcct gggctcaaac                                         20

<210> SEQ ID NO 291
<211> LENGTH: 18
<212> TYPE: DNA
<213> ORGANISM: Homo sapiens

<400> SEQUENCE: 291
cagccacatc ccctatg                                            18

<210> SEQ ID NO 292
<211> LENGTH: 20
<212> TYPE: DNA
<213> ORGANISM: Homo sapiens

<400> SEQUENCE: 292
tgccttcttc cactccttcc                                         20

<210> SEQ ID NO 293
<211> LENGTH: 23
```

```
<212> TYPE: DNA
<213> ORGANISM: Homo sapiens

<400> SEQUENCE: 293
aagagtgaaa gcagagatgt tcc                                           23

<210> SEQ ID NO 294
<211> LENGTH: 21
<212> TYPE: DNA
<213> ORGANISM: Homo sapiens

<400> SEQUENCE: 294
actaagcctc aggagcagcc t                                             21

<210> SEQ ID NO 295
<211> LENGTH: 25
<212> TYPE: DNA
<213> ORGANISM: Homo sapiens

<400> SEQUENCE: 295
gatacttggg gaagagagac ctacc                                         25

<210> SEQ ID NO 296
<211> LENGTH: 19
<212> TYPE: DNA
<213> ORGANISM: Homo sapiens

<400> SEQUENCE: 296
gaggggagag gaggggag                                                 19

<210> SEQ ID NO 297
<211> LENGTH: 20
<212> TYPE: DNA
<213> ORGANISM: Homo sapiens

<400> SEQUENCE: 297
cacaaacctg cccacattgc                                               20

<210> SEQ ID NO 298
<211> LENGTH: 18
<212> TYPE: DNA
<213> ORGANISM: Homo sapiens

<400> SEQUENCE: 298
cctgggcggc tcaactct                                                 18

<210> SEQ ID NO 299
<211> LENGTH: 19
<212> TYPE: DNA
<213> ORGANISM: Homo sapiens

<400> SEQUENCE: 299
aggcgtttcc gtttatggc                                                19

<210> SEQ ID NO 300
<211> LENGTH: 23
<212> TYPE: DNA
<213> ORGANISM: Homo sapiens

<400> SEQUENCE: 300
ctgcttcttg agtaacactt acg                                           23

<210> SEQ ID NO 301
<211> LENGTH: 26
```

<212> TYPE: DNA
<213> ORGANISM: Homo sapiens

<400> SEQUENCE: 301
gattacgaag gtattggttt agacag                                26

<210> SEQ ID NO 302
<211> LENGTH: 26
<212> TYPE: DNA
<213> ORGANISM: Homo sapiens

<400> SEQUENCE: 302
ggtgttaaaa atagttccat agttcg                                26

<210> SEQ ID NO 303
<211> LENGTH: 20
<212> TYPE: DNA
<213> ORGANISM: Homo sapiens

<400> SEQUENCE: 303
tataagcagt ccctgccttc                                       20

<210> SEQ ID NO 304
<211> LENGTH: 20
<212> TYPE: DNA
<213> ORGANISM: Homo sapiens

<400> SEQUENCE: 304
tataagcagt ccctgccttc                                       20

<210> SEQ ID NO 305
<211> LENGTH: 20
<212> TYPE: DNA
<213> ORGANISM: Homo sapiens

<400> SEQUENCE: 305
ctgggcgaga gtgagattcc                                       20

<210> SEQ ID NO 306
<211> LENGTH: 19
<212> TYPE: DNA
<213> ORGANISM: Homo sapiens

<400> SEQUENCE: 306
atgaacccag gaggcagag                                        19

<210> SEQ ID NO 307
<211> LENGTH: 20
<212> TYPE: DNA
<213> ORGANISM: Homo sapiens

<400> SEQUENCE: 307
cggagatttg gatgttctcc                                       20

<210> SEQ ID NO 308
<211> LENGTH: 20
<212> TYPE: DNA
<213> ORGANISM: Homo sapiens

<400> SEQUENCE: 308
cggagatttg gatgttctcc                                       20

<210> SEQ ID NO 309
<211> LENGTH: 21

```
<212> TYPE: DNA
<213> ORGANISM: Homo sapiens

<400> SEQUENCE: 309
tttgtagaaa tggggtcttg c                                              21

<210> SEQ ID NO 310
<211> LENGTH: 21
<212> TYPE: DNA
<213> ORGANISM: Homo sapiens

<400> SEQUENCE: 310
aattcctgaa gctctcccaa g                                              21

<210> SEQ ID NO 311
<211> LENGTH: 20
<212> TYPE: DNA
<213> ORGANISM: Homo sapiens

<400> SEQUENCE: 311
tgctgaacca gtcaaactcc                                                20

<210> SEQ ID NO 312
<211> LENGTH: 23
<212> TYPE: DNA
<213> ORGANISM: Homo sapiens

<400> SEQUENCE: 312
ttgcaatatt ggtcctagag ttc                                            23

<210> SEQ ID NO 313
<211> LENGTH: 26
<212> TYPE: DNA
<213> ORGANISM: Homo sapiens

<400> SEQUENCE: 313
ccacaaatat caatttacaa ccattg                                         26

<210> SEQ ID NO 314
<211> LENGTH: 25
<212> TYPE: DNA
<213> ORGANISM: Homo sapiens

<400> SEQUENCE: 314
tggaaataat gttaagggtg ttttt                                          25

<210> SEQ ID NO 315
<211> LENGTH: 20
<212> TYPE: DNA
<213> ORGANISM: Homo sapiens

<400> SEQUENCE: 315
tctgcatggc cgatctaaag                                                20

<210> SEQ ID NO 316
<211> LENGTH: 26
<212> TYPE: DNA
<213> ORGANISM: Homo sapiens

<400> SEQUENCE: 316
aaagttgaga agctcatcac tggtac                                         26

<210> SEQ ID NO 317
<211> LENGTH: 21
```

```
<212> TYPE: DNA
<213> ORGANISM: Homo sapiens

<400> SEQUENCE: 317
tggttccaaa tcctaatctg c                                              21

<210> SEQ ID NO 318
<211> LENGTH: 23
<212> TYPE: DNA
<213> ORGANISM: Homo sapiens

<400> SEQUENCE: 318
ttgagggtag gagaatgaga gag                                            23

<210> SEQ ID NO 319
<211> LENGTH: 22
<212> TYPE: DNA
<213> ORGANISM: Homo sapiens

<400> SEQUENCE: 319
catgcatatt tcaaaggtca ag                                             22

<210> SEQ ID NO 320
<211> LENGTH: 26
<212> TYPE: DNA
<213> ORGANISM: Homo sapiens

<400> SEQUENCE: 320
tcaagtaaga ggaggatatg tcaaag                                         26

<210> SEQ ID NO 321
<211> LENGTH: 24
<212> TYPE: DNA
<213> ORGANISM: Homo sapiens

<400> SEQUENCE: 321
catcaaatat ttcaaaggtt gagc                                           24

<210> SEQ ID NO 322
<211> LENGTH: 20
<212> TYPE: DNA
<213> ORGANISM: Homo sapiens

<400> SEQUENCE: 322
gtcaaaacaa atggcacacg                                                20

<210> SEQ ID NO 323
<211> LENGTH: 20
<212> TYPE: DNA
<213> ORGANISM: Homo sapiens

<400> SEQUENCE: 323
ttacaggcat gaaccaccac                                                20

<210> SEQ ID NO 324
<211> LENGTH: 20
<212> TYPE: DNA
<213> ORGANISM: Homo sapiens

<400> SEQUENCE: 324
cctatgcaat cggtctttgc                                                20

<210> SEQ ID NO 325
<211> LENGTH: 21
```

```
<212> TYPE: DNA
<213> ORGANISM: Homo sapiens

<400> SEQUENCE: 325 gggattttt gttttgtttt g                                          21

<210> SEQ ID NO 326
<211> LENGTH: 20
<212> TYPE: DNA
<213> ORGANISM: Homo sapiens

<400> SEQUENCE: 326 aaagggaaa tgcgtaggac                                            20

<210> SEQ ID NO 327
<211> LENGTH: 20
<212> TYPE: DNA
<213> ORGANISM: Homo sapiens

<400> SEQUENCE: 327
tcccaaagtg ctgggattac                                           20

<210> SEQ ID NO 328
<211> LENGTH: 27
<212> TYPE: DNA
<213> ORGANISM: Homo sapiens

<400> SEQUENCE: 328
ccagaactta aagtgaaatt taaaaag                                   27

<210> SEQ ID NO 329
<211> LENGTH: 19
<212> TYPE: DNA
<213> ORGANISM: Homo sapiens

<400> SEQUENCE: 329
gcgaggcaaa acacaaagc                                            19

<210> SEQ ID NO 330
<211> LENGTH: 21
<212> TYPE: DNA
<213> ORGANISM: Homo sapiens

<400> SEQUENCE: 330
ttggaaatgg ctgtacctca g                                         21

<210> SEQ ID NO 331
<211> LENGTH: 19
<212> TYPE: DNA
<213> ORGANISM: Homo sapiens

<400> SEQUENCE: 331
tacttgagca gcccacagg                                            19

<210> SEQ ID NO 332
<211> LENGTH: 24
<212> TYPE: DNA
<213> ORGANISM: Homo sapiens

<400> SEQUENCE: 332
aaaggaatga aagtggtttt tgtc                                      24

<210> SEQ ID NO 333
<211> LENGTH: 23
```

```
<212> TYPE: DNA
<213> ORGANISM: Homo sapiens

<400> SEQUENCE: 333
tgcaatgtaa tagttttcca agg                                          23

<210> SEQ ID NO 334
<211> LENGTH: 22
<212> TYPE: DNA
<213> ORGANISM: Homo sapiens

<400> SEQUENCE: 334
cagcaaatga actaagccac ag                                           22

<210> SEQ ID NO 335
<211> LENGTH: 24
<212> TYPE: DNA
<213> ORGANISM: Homo sapiens

<400> SEQUENCE: 335
tgctatacta tttgcccaca aaac                                         24

<210> SEQ ID NO 336
<211> LENGTH: 24
<212> TYPE: DNA
<213> ORGANISM: Homo sapiens

<400> SEQUENCE: 336
gaatgcattt attcagagat gagg                                         24

<210> SEQ ID NO 337
<211> LENGTH: 21
<212> TYPE: DNA
<213> ORGANISM: Homo sapiens

<400> SEQUENCE: 337
tgctagacac ttgctggtca c                                            21

<210> SEQ ID NO 338
<211> LENGTH: 25
<212> TYPE: DNA
<213> ORGANISM: Homo sapiens

<400> SEQUENCE: 338
ttgatattaa agttgcacaa actgc                                        25

<210> SEQ ID NO 339
<211> LENGTH: 25
<212> TYPE: DNA
<213> ORGANISM: Homo sapiens

<400> SEQUENCE: 339
tcaattgtgt gacatatcac ctacc                                        25

<210> SEQ ID NO 340
<211> LENGTH: 24
<212> TYPE: DNA
<213> ORGANISM: Homo sapiens

<400> SEQUENCE: 340
tcactgtaga aatccaagta ccac                                         24

<210> SEQ ID NO 341
<211> LENGTH: 21
```

```
<212> TYPE: DNA
<213> ORGANISM: Homo sapiens

<400> SEQUENCE: 341
tctgcatcag tttgattctg c                                             21

<210> SEQ ID NO 342
<211> LENGTH: 22
<212> TYPE: DNA
<213> ORGANISM: Homo sapiens

<400> SEQUENCE: 342
aatgcacttt ttattttatt ag                                            22

<210> SEQ ID NO 343
<211> LENGTH: 20
<212> TYPE: DNA
<213> ORGANISM: Homo sapiens

<400> SEQUENCE: 343
gaaaagtgcc ggttcttgag                                               20

<210> SEQ ID NO 344
<211> LENGTH: 20
<212> TYPE: DNA
<213> ORGANISM: Homo sapiens

<400> SEQUENCE: 344
gcctacacag tccgttttcc                                               20

<210> SEQ ID NO 345
<211> LENGTH: 19
<212> TYPE: DNA
<213> ORGANISM: Homo sapiens

<400> SEQUENCE: 345
agaggagcgt gtgttgcag                                                19

<210> SEQ ID NO 346
<211> LENGTH: 20
<212> TYPE: DNA
<213> ORGANISM: Homo sapiens

<400> SEQUENCE: 346
actctgacgg tggagctgag                                               20

<210> SEQ ID NO 347
<211> LENGTH: 24
<212> TYPE: DNA
<213> ORGANISM: Homo sapiens

<400> SEQUENCE: 347
gctcttggtg ctaagttaaa gagg                                          24

<210> SEQ ID NO 348
<211> LENGTH: 20
<212> TYPE: DNA
<213> ORGANISM: Homo sapiens

<400> SEQUENCE: 348
atccagctgg ctctgatagg                                               20

<210> SEQ ID NO 349
<211> LENGTH: 20
```

```
<212> TYPE: DNA
<213> ORGANISM: Homo sapiens

<400> SEQUENCE: 349
tgaacagcca gatcctctcc                                               20

<210> SEQ ID NO 350
<211> LENGTH: 20
<212> TYPE: DNA
<213> ORGANISM: Homo sapiens

<400> SEQUENCE: 350
gtcccacctt gttaggaagc                                               20

<210> SEQ ID NO 351
<211> LENGTH: 20
<212> TYPE: DNA
<213> ORGANISM: Homo sapiens

<400> SEQUENCE: 351
tggcattctg aaaacggttc                                               20

<210> SEQ ID NO 352
<211> LENGTH: 19
<212> TYPE: DNA
<213> ORGANISM: Homo sapiens

<400> SEQUENCE: 352
gcaaacagcc tggacaatc                                                19

<210> SEQ ID NO 353
<211> LENGTH: 22
<212> TYPE: DNA
<213> ORGANISM: Homo sapiens

<400> SEQUENCE: 353
cacatatttc tgtcccctgt tg                                            22

<210> SEQ ID NO 354
<211> LENGTH: 20
<212> TYPE: DNA
<213> ORGANISM: Homo sapiens

<400> SEQUENCE: 354
tgtggttctt tggagcacag                                               20

<210> SEQ ID NO 355
<211> LENGTH: 21
<212> TYPE: DNA
<213> ORGANISM: Homo sapiens

<400> SEQUENCE: 355
ccaaggtaca tttcggaaaa c                                             21

<210> SEQ ID NO 356
<211> LENGTH: 20
<212> TYPE: DNA
<213> ORGANISM: Homo sapiens

<400> SEQUENCE: 356
accagccctt tcctcttgtc                                               20

<210> SEQ ID NO 357
<211> LENGTH: 20
```

```
<212> TYPE: DNA
<213> ORGANISM: Homo sapiens

<400> SEQUENCE: 357
ttcttcctca tgccattgtg                                              20

<210> SEQ ID NO 358
<211> LENGTH: 19
<212> TYPE: DNA
<213> ORGANISM: Homo sapiens

<400> SEQUENCE: 358
gtggcatctg gctgtcatc                                               19

<210> SEQ ID NO 359
<211> LENGTH: 24
<212> TYPE: DNA
<213> ORGANISM: Homo sapiens

<400> SEQUENCE: 359
caattagttt tccttgagca ctcc                                         24

<210> SEQ ID NO 360
<211> LENGTH: 24
<212> TYPE: DNA
<213> ORGANISM: Homo sapiens

<400> SEQUENCE: 360
tcttctttat ccaggacatc tgtg                                         24

<210> SEQ ID NO 361
<211> LENGTH: 19
<212> TYPE: DNA
<213> ORGANISM: Homo sapiens

<400> SEQUENCE: 361
cctgggagag gtctggttc                                               19

<210> SEQ ID NO 362
<211> LENGTH: 20
<212> TYPE: DNA
<213> ORGANISM: Homo sapiens

<400> SEQUENCE: 362
ggcagcatct tggtctgaag                                              20

<210> SEQ ID NO 363
<211> LENGTH: 20
<212> TYPE: DNA
<213> ORGANISM: Homo sapiens

<400> SEQUENCE: 363
gagcacttgg gagacctgag                                              20

<210> SEQ ID NO 364
<211> LENGTH: 20
<212> TYPE: DNA
<213> ORGANISM: Homo sapiens

<400> SEQUENCE: 364
agggaagcat gagcacagtc                                              20

<210> SEQ ID NO 365
<211> LENGTH: 20
```

```
<212> TYPE: DNA
<213> ORGANISM: Homo sapiens

<400> SEQUENCE: 365
tgagttctgt ctggctgtgg                                        20

<210> SEQ ID NO 366
<211> LENGTH: 20
<212> TYPE: DNA
<213> ORGANISM: Homo sapiens

<400> SEQUENCE: 366
tgatgaggga tgagggaaac                                        20

<210> SEQ ID NO 367
<211> LENGTH: 20
<212> TYPE: DNA
<213> ORGANISM: Homo sapiens

<400> SEQUENCE: 367
agggttaggg agcctagctg                                        20

<210> SEQ ID NO 368
<211> LENGTH: 19
<212> TYPE: DNA
<213> ORGANISM: Homo sapiens

<400> SEQUENCE: 368
tccttggaac acccctgtc                                         19

<210> SEQ ID NO 369
<211> LENGTH: 25
<212> TYPE: DNA
<213> ORGANISM: Homo sapiens

<400> SEQUENCE: 369
cagtcatgat acctacactt ccatc                                  25

<210> SEQ ID NO 370
<211> LENGTH: 25
<212> TYPE: DNA
<213> ORGANISM: Homo sapiens

<400> SEQUENCE: 370
caactctgaa ataaaagcaa tctgg                                  25

<210> SEQ ID NO 371
<211> LENGTH: 25
<212> TYPE: DNA
<213> ORGANISM: Homo sapiens

<400> SEQUENCE: 371
ttctttggtt atgaaatgaa caatc                                  25

<210> SEQ ID NO 372
<211> LENGTH: 27
<212> TYPE: DNA
<213> ORGANISM: Homo sapiens

<400> SEQUENCE: 372
ttgaataaaa gtagatgttt cttgtcc                                27

<210> SEQ ID NO 373
<211> LENGTH: 27
```

```
<212> TYPE: DNA
<213> ORGANISM: Homo sapiens

<400> SEQUENCE: 373
taccaagaat ataatacgtt gttatgg                                    27

<210> SEQ ID NO 374
<211> LENGTH: 20
<212> TYPE: DNA
<213> ORGANISM: Homo sapiens

<400> SEQUENCE: 374
cggcttctgg cacataaaac                                            20

<210> SEQ ID NO 375
<211> LENGTH: 23
<212> TYPE: DNA
<213> ORGANISM: Homo sapiens

<400> SEQUENCE: 375
ccattgagca ctccattcat tac                                        23

<210> SEQ ID NO 376
<211> LENGTH: 21
<212> TYPE: DNA
<213> ORGANISM: Homo sapiens

<400> SEQUENCE: 376
ccctgggaat ctgaaagaat g                                          21

<210> SEQ ID NO 377
<211> LENGTH: 20
<212> TYPE: DNA
<213> ORGANISM: Homo sapiens

<400> SEQUENCE: 377
tgggccgttg tctcatatac                                            20

<210> SEQ ID NO 378
<211> LENGTH: 20
<212> TYPE: DNA
<213> ORGANISM: Homo sapiens

<400> SEQUENCE: 378
cactctggct tttccctctg                                            20

<210> SEQ ID NO 379
<211> LENGTH: 20
<212> TYPE: DNA
<213> ORGANISM: Homo sapiens

<400> SEQUENCE: 379
aggtcatgaa tgggatcctg                                            20

<210> SEQ ID NO 380
<211> LENGTH: 19
<212> TYPE: DNA
<213> ORGANISM: Homo sapiens

<400> SEQUENCE: 380
catattgctt ggcgtccac                                             19

<210> SEQ ID NO 381
<211> LENGTH: 21
```

```
<212> TYPE: DNA
<213> ORGANISM: Homo sapiens

<400> SEQUENCE: 381
tcttggtgat ctttgccttt g                                    21

<210> SEQ ID NO 382
<211> LENGTH: 27
<212> TYPE: DNA
<213> ORGANISM: Homo sapiens

<400> SEQUENCE: 382
tcatcaagat tattcgatat ttgagtc                              27

<210> SEQ ID NO 383
<211> LENGTH: 22
<212> TYPE: DNA
<213> ORGANISM: Homo sapiens

<400> SEQUENCE: 383
cgagaaagta aagtgcctgc tg                                   22

<210> SEQ ID NO 384
<211> LENGTH: 20
<212> TYPE: DNA
<213> ORGANISM: Homo sapiens

<400> SEQUENCE: 384
cgggattgga gacagacatc                                      20

<210> SEQ ID NO 385
<211> LENGTH: 19
<212> TYPE: DNA
<213> ORGANISM: Homo sapiens

<400> SEQUENCE: 385
gaggatgctg ccatttgtg                                       19

<210> SEQ ID NO 386
<211> LENGTH: 23
<212> TYPE: DNA
<213> ORGANISM: Homo sapiens

<400> SEQUENCE: 386
catgctaaca gagtgtcaag agc                                  23

<210> SEQ ID NO 387
<211> LENGTH: 20
<212> TYPE: DNA
<213> ORGANISM: Homo sapiens

<400> SEQUENCE: 387
cgaattcttt ttgccatttc                                      20

<210> SEQ ID NO 388
<211> LENGTH: 20
<212> TYPE: DNA
<213> ORGANISM: Homo sapiens

<400> SEQUENCE: 388
aaagtctgca aggggctatg                                      20

<210> SEQ ID NO 389
<211> LENGTH: 23
```

<212> TYPE: DNA
<213> ORGANISM: Homo sapiens

<400> SEQUENCE: 389
tcaggctaga aatgtatcca agg                                          23

<210> SEQ ID NO 390
<211> LENGTH: 20
<212> TYPE: DNA
<213> ORGANISM: Homo sapiens

<400> SEQUENCE: 390
aaaggaaagg ggtaatccag                                              20

<210> SEQ ID NO 391
<211> LENGTH: 27
<212> TYPE: DNA
<213> ORGANISM: Homo sapiens

<400> SEQUENCE: 391 tttactttt atgattacct ctgatgc                                       27

<210> SEQ ID NO 392
<211> LENGTH: 27
<212> TYPE: DNA
<213> ORGANISM: Homo sapiens

<400> SEQUENCE: 392
aaagaaaatt caaatgaaaa taagtcg                                      27

<210> SEQ ID NO 393
<211> LENGTH: 22
<212> TYPE: DNA
<213> ORGANISM: Homo sapiens

<400> SEQUENCE: 393
catgcaaact tgggtctaga tg                                           22

<210> SEQ ID NO 394
<211> LENGTH: 20
<212> TYPE: DNA
<213> ORGANISM: Homo sapiens

<400> SEQUENCE: 394
ttggcttttt cccctcatac                                              20

<210> SEQ ID NO 395
<211> LENGTH: 20
<212> TYPE: DNA
<213> ORGANISM: Homo sapiens

<400> SEQUENCE: 395
taaagccttt cccagctcag                                              20

<210> SEQ ID NO 396
<211> LENGTH: 19
<212> TYPE: DNA
<213> ORGANISM: Homo sapiens

<400> SEQUENCE: 396
cctgctgctt ccacaggac                                               19

<210> SEQ ID NO 397
<211> LENGTH: 19

-continued

<212> TYPE: DNA
<213> ORGANISM: Homo sapiens

<400> SEQUENCE: 397
catggacgtc ctgtggaag                                                   19

<210> SEQ ID NO 398
<211> LENGTH: 20
<212> TYPE: DNA
<213> ORGANISM: Homo sapiens

<400> SEQUENCE: 398
gtgtcccatt catcctcacc                                                  20

<210> SEQ ID NO 399
<211> LENGTH: 19
<212> TYPE: DNA
<213> ORGANISM: Homo sapiens

<400> SEQUENCE: 399
aacagaggag gcgctgaag                                                   19

<210> SEQ ID NO 400
<211> LENGTH: 18
<212> TYPE: DNA
<213> ORGANISM: Homo sapiens

<400> SEQUENCE: 400
gcctcaccct acccatcc                                                    18

<210> SEQ ID NO 401
<211> LENGTH: 20
<212> TYPE: DNA
<213> ORGANISM: Homo sapiens

<400> SEQUENCE: 401
agattgctgg ggttccttc                                                   20

<210> SEQ ID NO 402
<211> LENGTH: 20
<212> TYPE: DNA
<213> ORGANISM: Homo sapiens

<400> SEQUENCE: 402
ccacctcact ccatctctgg                                                  20

<210> SEQ ID NO 403
<211> LENGTH: 20
<212> TYPE: DNA
<213> ORGANISM: Homo sapiens

<400> SEQUENCE: 403
tggggtaagt tccctgagtg                                                  20

<210> SEQ ID NO 404
<211> LENGTH: 20
<212> TYPE: DNA
<213> ORGANISM: Homo sapiens

<400> SEQUENCE: 404
tacagagcca gggagagtgc                                                  20

<210> SEQ ID NO 405
<211> LENGTH: 20

```
<212> TYPE: DNA
<213> ORGANISM: Homo sapiens

<400> SEQUENCE: 405
tatcatccac atcggtcagc                                              20

<210> SEQ ID NO 406
<211> LENGTH: 25
<212> TYPE: DNA
<213> ORGANISM: Homo sapiens

<400> SEQUENCE: 406
tttgggacaa gtaattgtta ttagc                                        25

<210> SEQ ID NO 407
<211> LENGTH: 20
<212> TYPE: DNA
<213> ORGANISM: Homo sapiens

<400> SEQUENCE: 407
ttgaatgcag tggtgctctc                                              20

<210> SEQ ID NO 408
<211> LENGTH: 20
<212> TYPE: DNA
<213> ORGANISM: Homo sapiens

<400> SEQUENCE: 408
tctgcctgtg ttctgagctg                                              20

<210> SEQ ID NO 409
<211> LENGTH: 20
<212> TYPE: DNA
<213> ORGANISM: Homo sapiens

<400> SEQUENCE: 409
gaactcagct ctgcctggac                                              20

<210> SEQ ID NO 410
<211> LENGTH: 20
<212> TYPE: DNA
<213> ORGANISM: Homo sapiens

<400> SEQUENCE: 410
gcgagactcg gtctcaaaag                                              20

<210> SEQ ID NO 411
<211> LENGTH: 20
<212> TYPE: DNA
<213> ORGANISM: Homo sapiens

<400> SEQUENCE: 411
atcgtttgcc aactcctagc                                              20

<210> SEQ ID NO 412
<211> LENGTH: 20
<212> TYPE: DNA
<213> ORGANISM: Homo sapiens

<400> SEQUENCE: 412
aatcagtgca ggtgatgcag                                              20

<210> SEQ ID NO 413
<211> LENGTH: 20
```

```
<212> TYPE: DNA
<213> ORGANISM: Homo sapiens

<400> SEQUENCE: 413
acatggcctg tgtctgcttc                                               20

<210> SEQ ID NO 414
<211> LENGTH: 25
<212> TYPE: DNA
<213> ORGANISM: Homo sapiens

<400> SEQUENCE: 414
gactggaaga aaataaccaa gtttc                                         25

<210> SEQ ID NO 415
<211> LENGTH: 20
<212> TYPE: DNA
<213> ORGANISM: Homo sapiens

<400> SEQUENCE: 415
ggcaggcgtt aaaggaatag                                               20

<210> SEQ ID NO 416
<211> LENGTH: 19
<212> TYPE: DNA
<213> ORGANISM: Homo sapiens

<400> SEQUENCE: 416
aaaaacaggg cacccattg                                                19

<210> SEQ ID NO 417
<211> LENGTH: 20
<212> TYPE: DNA
<213> ORGANISM: Homo sapiens

<400> SEQUENCE: 417
ttaagcccac agggaacaag                                               20

<210> SEQ ID NO 418
<211> LENGTH: 20
<212> TYPE: DNA
<213> ORGANISM: Homo sapiens

<400> SEQUENCE: 418
tgtcagacct tggccttttc                                               20

<210> SEQ ID NO 419
<211> LENGTH: 23
<212> TYPE: DNA
<213> ORGANISM: Homo sapiens

<400> SEQUENCE: 419
tcttctgaaa aatggaggaa gtc                                           23

<210> SEQ ID NO 420
<211> LENGTH: 20
<212> TYPE: DNA
<213> ORGANISM: Homo sapiens

<400> SEQUENCE: 420
gctcttcctg gggaagtctc                                               20

<210> SEQ ID NO 421
<211> LENGTH: 20
```

```
<212> TYPE: DNA
<213> ORGANISM: Homo sapiens

<400> SEQUENCE: 421 cagttttga ctgccactgc                                               20

<210> SEQ ID NO 422
<211> LENGTH: 21
<212> TYPE: DNA
<213> ORGANISM: Homo sapiens

<400> SEQUENCE: 422
tccatgctcg acactattct g                                            21

<210> SEQ ID NO 423
<211> LENGTH: 26
<212> TYPE: DNA
<213> ORGANISM: Homo sapiens

<400> SEQUENCE: 423
ttctacttta catacaaaag gcactc                                       26

<210> SEQ ID NO 424
<211> LENGTH: 20
<212> TYPE: DNA
<213> ORGANISM: Homo sapiens

<400> SEQUENCE: 424
agttgggctt agcctggatg                                              20

<210> SEQ ID NO 425
<211> LENGTH: 21
<212> TYPE: DNA
<213> ORGANISM: Homo sapiens

<400> SEQUENCE: 425
agtatcacgt ccatgttgga g                                            21

<210> SEQ ID NO 426
<211> LENGTH: 21
<212> TYPE: DNA
<213> ORGANISM: Homo sapiens

<400> SEQUENCE: 426
caatgtttgc tttgaaaaag g                                            21

<210> SEQ ID NO 427
<211> LENGTH: 20
<212> TYPE: DNA
<213> ORGANISM: Homo sapiens

<400> SEQUENCE: 427
tgagcaaaac ctgtggaatg                                              20

<210> SEQ ID NO 428
<211> LENGTH: 20
<212> TYPE: DNA
<213> ORGANISM: Homo sapiens

<400> SEQUENCE: 428
tttgctggtg ctgtctatgg                                              20

<210> SEQ ID NO 429
<211> LENGTH: 22
```

```
<212> TYPE: DNA
<213> ORGANISM: Homo sapiens

<400> SEQUENCE: 429
ggatgtgcaa aatgttcttc tg                                            22

<210> SEQ ID NO 430
<211> LENGTH: 21
<212> TYPE: DNA
<213> ORGANISM: Homo sapiens

<400> SEQUENCE: 430
gggagcaggt gttattgatt g                                             21

<210> SEQ ID NO 431
<211> LENGTH: 20
<212> TYPE: DNA
<213> ORGANISM: Homo sapiens

<400> SEQUENCE: 431
ggtgaggagt tttcccaagc                                               20

<210> SEQ ID NO 432
<211> LENGTH: 26
<212> TYPE: DNA
<213> ORGANISM: Homo sapiens

<400> SEQUENCE: 432
agcacagagt tgttaatgt ttttag                                         26

<210> SEQ ID NO 433
<211> LENGTH: 23
<212> TYPE: DNA
<213> ORGANISM: Homo sapiens

<400> SEQUENCE: 433
gctgacttct attgggagca tac                                           23

<210> SEQ ID NO 434
<211> LENGTH: 21
<212> TYPE: DNA
<213> ORGANISM: Homo sapiens

<400> SEQUENCE: 434
cagaggtatg gtttgggtct c                                             21

<210> SEQ ID NO 435
<211> LENGTH: 21
<212> TYPE: DNA
<213> ORGANISM: Homo sapiens

<400> SEQUENCE: 435
tgggggtcta ggactatgga g                                             21

<210> SEQ ID NO 436
<211> LENGTH: 26
<212> TYPE: DNA
<213> ORGANISM: Homo sapiens

<400> SEQUENCE: 436
gctgtgtttt cttaatttcc tgtatg                                        26

<210> SEQ ID NO 437
<211> LENGTH: 19
```

```
<212> TYPE: DNA
<213> ORGANISM: Homo sapiens

<400> SEQUENCE: 437
cagcctcctg cagactttg                                            19

<210> SEQ ID NO 438
<211> LENGTH: 20
<212> TYPE: DNA
<213> ORGANISM: Homo sapiens

<400> SEQUENCE: 438
cattttggga aaggaggttc                                           20

<210> SEQ ID NO 439
<211> LENGTH: 20
<212> TYPE: DNA
<213> ORGANISM: Homo sapiens

<400> SEQUENCE: 439
cggtcagtat gacggtaggg                                           20

<210> SEQ ID NO 440
<211> LENGTH: 20
<212> TYPE: DNA
<213> ORGANISM: Homo sapiens

<400> SEQUENCE: 440
aggtcatgaa tgggatcctg                                           20

<210> SEQ ID NO 441
<211> LENGTH: 20
<212> TYPE: DNA
<213> ORGANISM: Homo sapiens

<400> SEQUENCE: 441
ggcgctaatc gtactgaaac                                           20

<210> SEQ ID NO 442
<211> LENGTH: 20
<212> TYPE: DNA
<213> ORGANISM: Homo sapiens

<400> SEQUENCE: 442
tatggtggcc atggagactg                                           20

<210> SEQ ID NO 443
<211> LENGTH: 19
<212> TYPE: DNA
<213> ORGANISM: Homo sapiens

<400> SEQUENCE: 443
aggagccctc ctttgattg                                            19

<210> SEQ ID NO 444
<211> LENGTH: 20
<212> TYPE: DNA
<213> ORGANISM: Homo sapiens

<400> SEQUENCE: 444
ggccagtggt atctgctgac                                           20

<210> SEQ ID NO 445
<211> LENGTH: 24
```

```
<212> TYPE: DNA
<213> ORGANISM: Homo sapiens

<400> SEQUENCE: 445
aagacaaaat cccaaataaa gcag                                           24

<210> SEQ ID NO 446
<211> LENGTH: 20
<212> TYPE: DNA
<213> ORGANISM: Homo sapiens

<400> SEQUENCE: 446
attggtttga gtgccctttg                                                20

<210> SEQ ID NO 447
<211> LENGTH: 22
<212> TYPE: DNA
<213> ORGANISM: Homo sapiens

<400> SEQUENCE: 447
aaaatgcttt gcactgactc tg                                             22

<210> SEQ ID NO 448
<211> LENGTH: 25
<212> TYPE: DNA
<213> ORGANISM: Homo sapiens

<400> SEQUENCE: 448
ttcatcttta ttgcccctat atctg                                          25

<210> SEQ ID NO 449
<211> LENGTH: 26
<212> TYPE: DNA
<213> ORGANISM: Homo sapiens

<400> SEQUENCE: 449
ttaaagatta taccaagtca gtggtc                                         26

<210> SEQ ID NO 450
<211> LENGTH: 20
<212> TYPE: DNA
<213> ORGANISM: Homo sapiens

<400> SEQUENCE: 450
catgtggttt cttgcctttg                                                20

<210> SEQ ID NO 451
<211> LENGTH: 24
<212> TYPE: DNA
<213> ORGANISM: Homo sapiens

<400> SEQUENCE: 451
aagcataggc tcagcatact acac                                           24

<210> SEQ ID NO 452
<211> LENGTH: 22
<212> TYPE: DNA
<213> ORGANISM: Homo sapiens

<400> SEQUENCE: 452
cccatcaact accatgtgac tg                                             22

<210> SEQ ID NO 453
<211> LENGTH: 22
```

```
<212> TYPE: DNA
<213> ORGANISM: Homo sapiens

<400> SEQUENCE: 453
ggtcctgttg tcagtttttc ag                                    22

<210> SEQ ID NO 454
<211> LENGTH: 20
<212> TYPE: DNA
<213> ORGANISM: Homo sapiens

<400> SEQUENCE: 454
ggtcctgggg tgctcctaga                                       20

<210> SEQ ID NO 455
<211> LENGTH: 22
<212> TYPE: DNA
<213> ORGANISM: Homo sapiens

<400> SEQUENCE: 455
tcctcaactg agccaagtag cc                                    22

<210> SEQ ID NO 456
<211> LENGTH: 22
<212> TYPE: DNA
<213> ORGANISM: Homo sapiens

<400> SEQUENCE: 456
tgtgtcctcc atgttctgtt gg                                    22

<210> SEQ ID NO 457
<211> LENGTH: 18
<212> TYPE: DNA
<213> ORGANISM: Homo sapiens

<400> SEQUENCE: 457
tggcccctct gcctagca                                         18

<210> SEQ ID NO 458
<211> LENGTH: 18
<212> TYPE: DNA
<213> ORGANISM: Homo sapiens

<400> SEQUENCE: 458
ccactgctgg gtcctggg                                         18

<210> SEQ ID NO 459
<211> LENGTH: 25
<212> TYPE: DNA
<213> ORGANISM: Homo sapiens

<400> SEQUENCE: 459
gaatagagag cttttcctga gatgc                                 25

<210> SEQ ID NO 460
<211> LENGTH: 24
<212> TYPE: DNA
<213> ORGANISM: Homo sapiens

<400> SEQUENCE: 460
gattcatctt gaagaagttg atgg                                  24

<210> SEQ ID NO 461
<211> LENGTH: 20
```

```
<212> TYPE: DNA
<213> ORGANISM: Homo sapiens

<400> SEQUENCE: 461
acttgatgcc cccaagaatc                                              20

<210> SEQ ID NO 462
<211> LENGTH: 21
<212> TYPE: DNA
<213> ORGANISM: Homo sapiens

<400> SEQUENCE: 462
ctcaagaagc agaaagggaa g                                            21

<210> SEQ ID NO 463
<211> LENGTH: 21
<212> TYPE: DNA
<213> ORGANISM: Homo sapiens

<400> SEQUENCE: 463
tctacagagt tccctgtttg c                                            21

<210> SEQ ID NO 464
<211> LENGTH: 21
<212> TYPE: DNA
<213> ORGANISM: Homo sapiens

<400> SEQUENCE: 464
gctgtggatc ttagggacct c                                            21

<210> SEQ ID NO 465
<211> LENGTH: 26
<212> TYPE: DNA
<213> ORGANISM: Homo sapiens

<400> SEQUENCE: 465
aaaaagcatt tctgatatgg ataaag                                       26

<210> SEQ ID NO 466
<211> LENGTH: 23
<212> TYPE: DNA
<213> ORGANISM: Homo sapiens

<400> SEQUENCE: 466
tcgaagtatg ttgctatcct ctg                                          23

<210> SEQ ID NO 467
<211> LENGTH: 25
<212> TYPE: DNA
<213> ORGANISM: Homo sapiens

<400> SEQUENCE: 467
aaaataataa gcatcagcat ttgac                                        25

<210> SEQ ID NO 468
<211> LENGTH: 21
<212> TYPE: DNA
<213> ORGANISM: Homo sapiens

<400> SEQUENCE: 468
ttattccaga cgcatttcca c                                            21

<210> SEQ ID NO 469
<211> LENGTH: 22
```

```
<212> TYPE: DNA
<213> ORGANISM: Homo sapiens

<400> SEQUENCE: 469
tttgagtcta tcgagtgtgt gc                                     22

<210> SEQ ID NO 470
<211> LENGTH: 21
<212> TYPE: DNA
<213> ORGANISM: Homo sapiens

<400> SEQUENCE: 470
ttcctgtttt tcgtttggtt g                                      21

<210> SEQ ID NO 471
<211> LENGTH: 21
<212> TYPE: DNA
<213> ORGANISM: Homo sapiens

<400> SEQUENCE: 471
tgaattttcc ttttggggaa g                                      21

<210> SEQ ID NO 472
<211> LENGTH: 25
<212> TYPE: DNA
<213> ORGANISM: Homo sapiens

<400> SEQUENCE: 472
tggatcaaat ccaaataaag taagg                                  25

<210> SEQ ID NO 473
<211> LENGTH: 25
<212> TYPE: DNA
<213> ORGANISM: Homo sapiens

<400> SEQUENCE: 473 ttgcttttte tgtaaatcat ctgtg                                  25

<210> SEQ ID NO 474
<211> LENGTH: 22
<212> TYPE: DNA
<213> ORGANISM: Homo sapiens

<400> SEQUENCE: 474
tatttcattt atttatgtgg ac                                     22

<210> SEQ ID NO 475
<211> LENGTH: 25
<212> TYPE: DNA
<213> ORGANISM: Homo sapiens

<400> SEQUENCE: 475
gaagttaagg cagtgtttta gatgg                                  25

<210> SEQ ID NO 476
<211> LENGTH: 25
<212> TYPE: DNA
<213> ORGANISM: Homo sapiens

<400> SEQUENCE: 476
accagtaata tccactttct ttctg                                  25

<210> SEQ ID NO 477
<211> LENGTH: 24
```

```
<212> TYPE: DNA
<213> ORGANISM: Homo sapiens

<400> SEQUENCE: 477
tttattggat ttcaaaaatg agtg                                  24

<210> SEQ ID NO 478
<211> LENGTH: 25
<212> TYPE: DNA
<213> ORGANISM: Homo sapiens

<400> SEQUENCE: 478
tctcatgtga gaaagagatt agcag                                 25

<210> SEQ ID NO 479
<211> LENGTH: 22
<212> TYPE: DNA
<213> ORGANISM: Homo sapiens

<400> SEQUENCE: 479
tggctttcag tagttttcat gg                                    22

<210> SEQ ID NO 480
<211> LENGTH: 18
<212> TYPE: DNA
<213> ORGANISM: Homo sapiens

<400> SEQUENCE: 480
catgtgatgg cgtgatcc                                         18

<210> SEQ ID NO 481
<211> LENGTH: 22
<212> TYPE: DNA
<213> ORGANISM: Homo sapiens

<400> SEQUENCE: 481
aggaatacac aaacaccgac ag                                    22

<210> SEQ ID NO 482
<211> LENGTH: 21
<212> TYPE: DNA
<213> ORGANISM: Homo sapiens

<400> SEQUENCE: 482
tgcaccctgt tttctttct c                                      21

<210> SEQ ID NO 483
<211> LENGTH: 23
<212> TYPE: DNA
<213> ORGANISM: Homo sapiens

<400> SEQUENCE: 483
tggacaagta atggttttct ctg                                   23

<210> SEQ ID NO 484
<211> LENGTH: 21
<212> TYPE: DNA
<213> ORGANISM: Homo sapiens

<400> SEQUENCE: 484
tgacatttga gcaaagacct g                                     21

<210> SEQ ID NO 485
<211> LENGTH: 20
```

```
<212> TYPE: DNA
<213> ORGANISM: Homo sapiens

<400> SEQUENCE: 485
tttgttttgt tttgttttttt                                                  20

<210> SEQ ID NO 486
<211> LENGTH: 27
<212> TYPE: DNA
<213> ORGANISM: Homo sapiens

<400> SEQUENCE: 486
ttacttatag gtttcaggag atgtgtt                                           27

<210> SEQ ID NO 487
<211> LENGTH: 23
<212> TYPE: DNA
<213> ORGANISM: Homo sapiens

<400> SEQUENCE: 487
gggtctttcg aatgtatgca atg                                               23
```

MUTATIONS OF THE PIK3CA GENE IN HUMAN CANCERS

This application was made using funds provided by the United States government under grant nos. NIH-CA 62924 and NIH-CA 43460. The United States government therefore retains certain rights in the invention.

FIELD OF THE INVENTION

The invention relates to the fields of diagnostic tests and therapeutic methods for cancer.

BACKGROUND OF THE INVENTION

PI3Ks are lipid kinases that function as signal transducers downstream of cell surface receptors and mediate pathways important for cell growth, proliferation, adhesion, survival and motility (1, 2). Although increased PI3K activity has been observed in many colorectal and other tumors (3, 4), no intragenic mutations of PI3K have been identified.

Members of the PIK3 pathway have been previously reported to be altered in cancers, for example, the PTEN tumor suppressor gene (15, 16), whose function is to reverse the phosphorylation mediated by PI3Ks (17, 18). Reduplication or amplification of the chromosomal regions containing PIK3CA and AKT2 has been reported in some human cancers (2, 19, 20), but the genes that are the targets of such large-scale genetic events have not been and cannot easily be defined.

BRIEF SUMMARY OF THE INVENTION

In a first embodiment a method is provided for assessing cancer in a human tissue suspected of being cancerous of a patient. A non-synonymous, intragenic mutation in a PIK3CA coding sequence is detected in a body sample of a human suspected of having a cancer. The human is identified as likely to have a cancer if a non-synonymous, intragenic mutation in PIK3CA coding sequence is determined in the body sample.

In a second embodiment of the invention a method is provided for inhibiting progression of a tumor in a human. An antisense oligonucleotide or antisense construct is administered to a tumor. The antisense oligonucleotide or RNA transcribed from the antisense construct is complementary to mRNA transcribed from PIK3CA. The amount of p110α protein expressed by the tumor is thereby reduced.

Another embodiment of the invention provides a method of inhibiting progression of a tumor in a human. siRNA comprising 19 to 21 bp duplexes of a human PIK3CA mRNA with 2 nt 3' overhangs are administered to the human. One strand of the duplex comprises a contiguous sequence selected from mRNA transcribed from PIK3CA (SEQ ID NO: 2). The amount of p110α protein expressed by the tumor is thereby reduced.

According to another aspect of the invention a method is provided for inhibiting progression of a tumor. A molecule comprising an antibody binding region is administered to a tumor. The antibody binding region specifically binds to PIK3CA (SEQ ID NO: 3).

Another embodiment of the invention provides a method of identifying candidate chemotherapeutic agents. A wild-type or activated mutant p110α (SEQ ID NO: 3) is contacted with a test compound. p110α activity is then measured. A test compound is identified as a candidate chemotherapeutic agent if it inhibits p110α activity.

Still another embodiment of the invention is a method for delivering an appropriate chemotherapeutic drug to a patient in need thereof. A non-synonymous, intragenic mutation in a PIK3CA coding sequence (SEQ ID NO: 1) is determined in a test tissue of a patient. A p110α inhibitor is administered to the patient.

An additional aspect of the invention provides a set of one or more primers for amplifying and/or sequencing PIK3CA. The primers are selected from the group consisting of forward primers, reverse primers and sequencing primers. The forward primers are selected from the group consisting of: SEQ ID NO: 6 to 158; the reverse primers are selected from the group consisting of: SEQ ID NO: 159 to 310; and the sequencing primers are selected from the group consisting of: SEQ ID NO: 311 to 461.

BRIEF DESCRIPTION OF THE DRAWINGS

(FIG. 3A) Half of the immunoprecipitates were subjected to a PI3-kinase assay using phosphatidylinositol as a substrate. "PI3P" indicates the position of PI-3-phosphate determined with standard phosphatidyl markers and "Ori" indicates the origin. (FIG. 3B) The other half of the immunoprecipitates was analyzed by western blotting with anti-p110α antibody. (FIG. 3C) Cell lysates from transfected cells contained similar amounts of total protein as determined by western blotting using an anti-α-tubulin antibody. Identical results to those shown in this figure were observed in three independent transfection experiments.

DETAILED DESCRIPTION OF THE INVENTION

Figure 1:
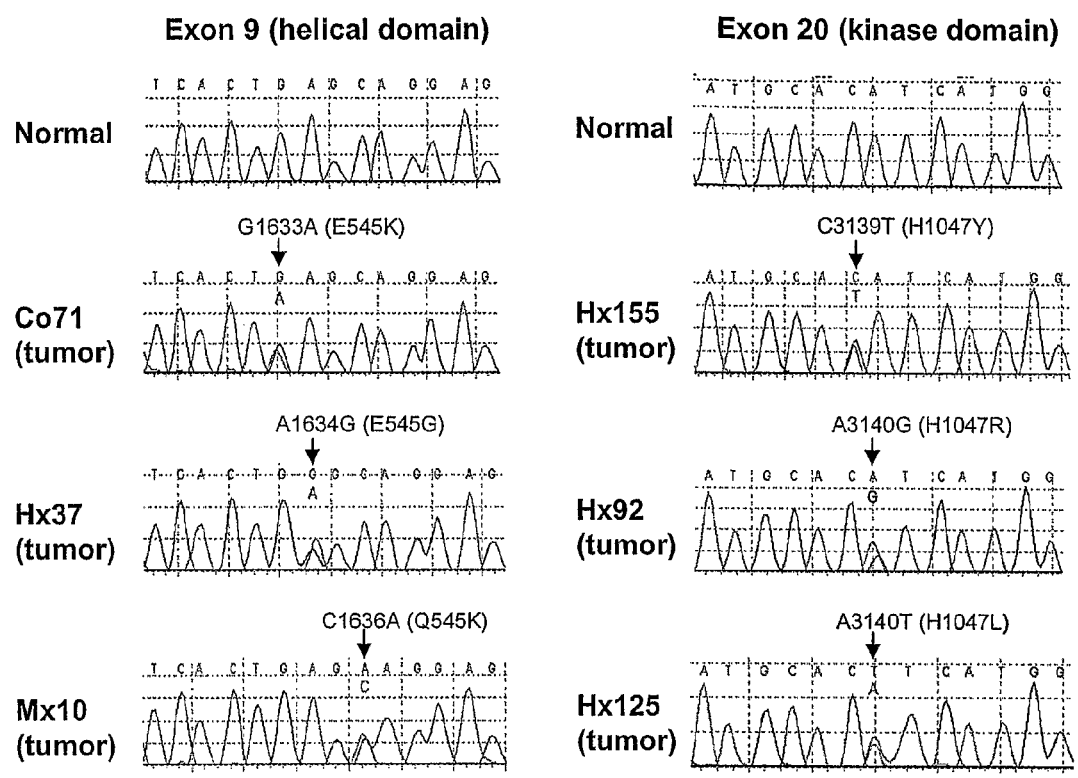
FIG. 1. Detection of mutations in of PIK3CA. Representative examples of mutations in exons 9 and 20. In each case, the top sequence chromatogram was obtained from normal tissue and the three lower sequence chromatograms from the indicated tumors. Arrows indicate the location of missense mutations. The nucleotide and amino acid alterations are indicated above the arrow.
Figure 2:
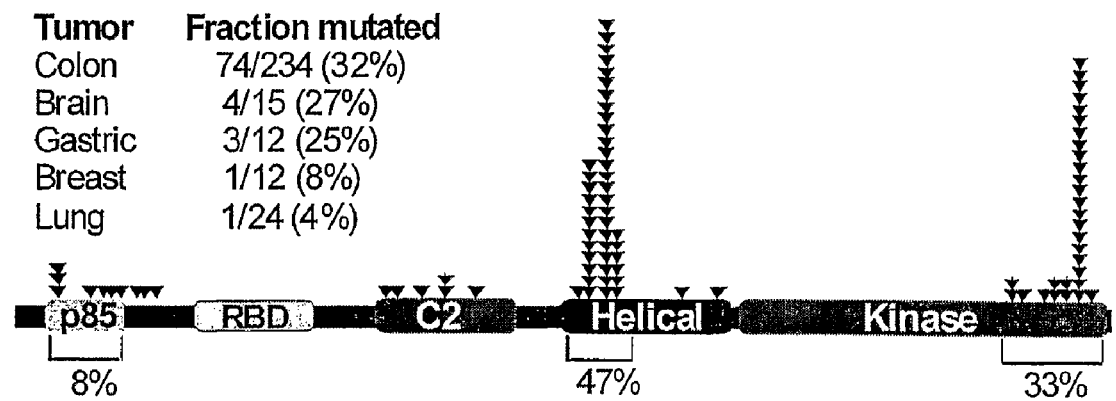
FIG. 2. Distribution of mutations in PIK3CA. Arrows indicate the location of missense mutations, and boxes represent functional domains (p85BD, p85 binding domain; RBD, Ras binding domain; C2 domain; Helical domain; Kinase domain). The percentage of mutations detected within each region in cancers is indicated below.
Figure 3:
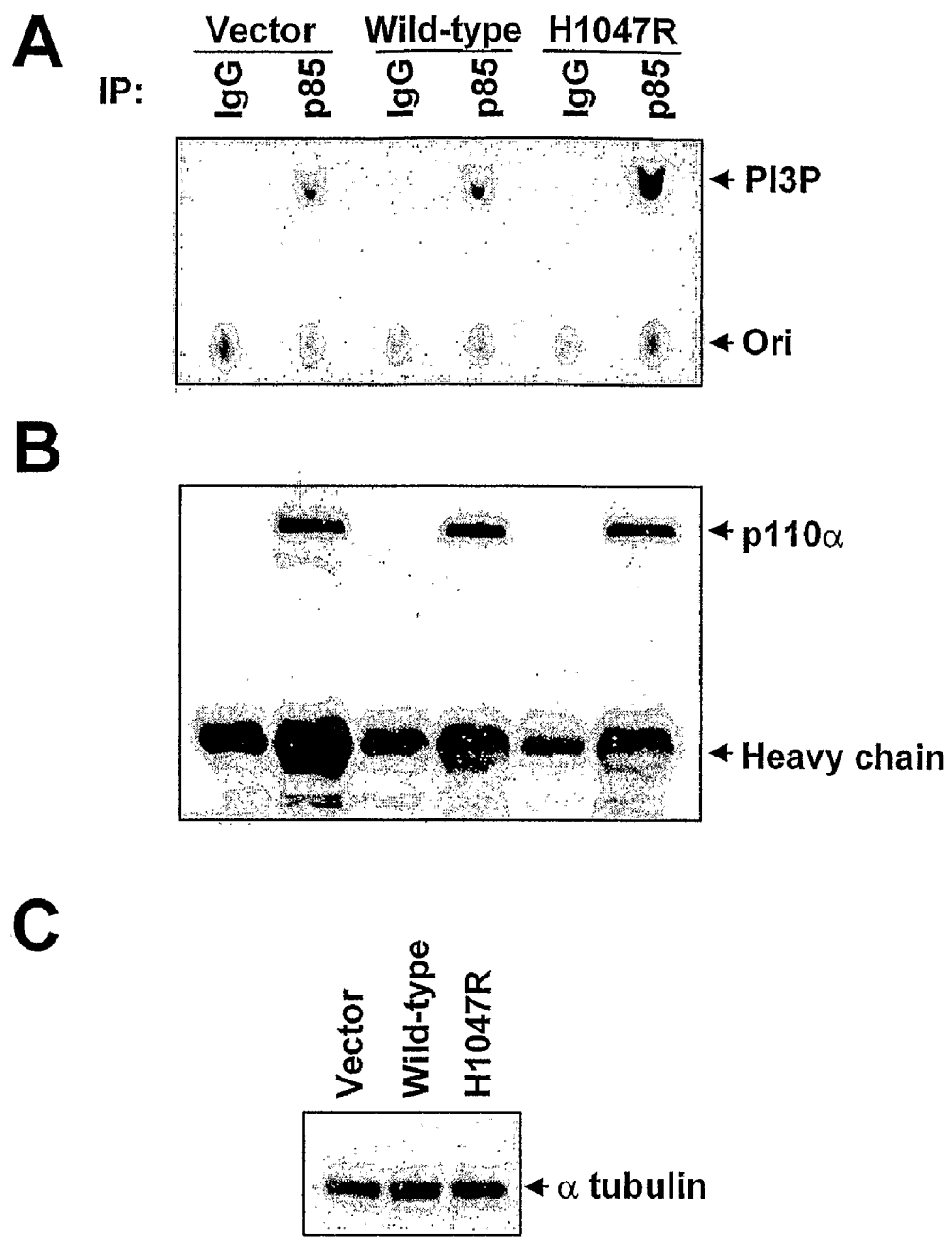
FIGS. 3A-3C. Increased lipid kinase activity of mutant p110α. NIH3T3 cells were transfected with empty vector or with vector constructs containing either wild-type p110α or mutant p110α (H1047R) as indicated above the lanes. Immunoprecipitations were performed either with control IgG or anti-p85 polyclonal antibodies.

The clustering of mutations within PIK3CA make it an excellent marker for early detection or for following disease progression. Testing focused in the clustered regions will yield most of the mutant alleles.

The human PIK3CA coding sequence is reported in the literature and is shown in SEQ ID NO: 1. This is the sequence of one particular individual in the population of humans. Humans vary from one another in their gene sequences. These variations are very minimal, sometimes occurring at a frequency of about 1 to 10 nucleotides per gene. Different forms of any particular gene exist within the human population. These different forms are called allelic variants. Allelic variants often do not change the amino acid sequence of the encoded protein; such variants are termed synonymous. Even if they do change the encoded amino acid (non-synonymous), the function of the protein is not typically affected. Such changes are evolutionarily or functionally neutral. When human PIK3CA is referred to in the present application all allelic variants are intended to be encompassed by the term. The sequence of SEQ ID NO: 1 is provided merely as a representative example of a wild-type human sequence. The invention is not limited to this single allelic form of PIK3CA. For purposes of determining a mutation, PIK3CA sequences determined in a test sample can be compared to a sequence determined in a different tissue of the human. A difference in the sequence in the two tissues indicates a somatic mutation. Alternatively, the sequence determined in a PIK3CA gene in a test sample can be compared to the sequence of SEQ ID NO: 1. A difference between the test sample sequence and SEQ ID NO: 1 can be identified as a mutation. Tissues suspected of being cancerous can be tested, as can body samples that may be expected to contain sloughed-off cells from tumors or cells of cancers. Suitable body samples for testing include blood, serum, plasma, sputum, urine, stool, nipple aspirate, saliva, and cerebrospinal fluid.

Mutations in PIK3CA cluster in exons 9 (SEQ ID NO: 4) and 20 (SEQ ID NO: 5). Other mutations occur, but these two exons appear to be the hotspots for mutations. Many mutations occur in PIK3CA's helical domain (nt 1567-2124 of SEQ ID NO: 2) and in its kinase domain (nt 2095-3096 of SEQ ID NO: 2). Fewer occur in PIK3CA's P85BD domain (nt 103-335 of SEQ ID NO: 2). Mutations have been found in exons 1, 2, 4, 5, 7, 9, 13, 18, and 20. Any combination of these exons can be tested, optionally in conjunction with testing other exons. Testing for mutations can be done along the whole coding sequence or can be focused in the areas where mutations have been found to cluster. Particular hotspots of mutations occur at nucleotide positions 1624, 1633, 1636, and 3140 of PIK3CA coding sequence.

PIK3CA mutations have been found in a variety of different types of tumors. Thus any of a variety of tumors can be tested for PIK3CA mutations. These tissues include, without limitation: colorectal tissue, brain tissue, gastric tissue, breast tissue, and lung tissue.

Any type of intragenic mutation can be detected. These include substitution mutations, deletion mutations, and insertion mutations. The size of the mutations is likely to be small, on the order of from 1 to 3 nucleotides. Mutations which can be detected include, but are not limited to G1624A, G1633A, C1636A, A3140G, G113A, T1258C, G3129T, C3139T, and G2702T. Any combination of these mutations can be tested.

The mutations that are found in PIK3CA appear to be activating mutations. Thus therapeutic regimens involving inhibition of p110α activity or expression can be used to inhibit progression of a tumor in a human. Inhibitory molecules which can be used include antisense oligonucleotides or antisense constructs, a molecule comprising an antibody binding region, and siRNA molecules. Molecules comprising an antibody binding region can be full antibodies, single chain variable regions, antibody fragments, antibody conjugates, etc. The antibody binding regions may but need not bind to epitopes contained within the kinase domain (nt 2095-3096 of SEQ ID NO: 2) of PIK3CA, the helical domain (nt 1567-2124 of SEQ ID NO: 2) of PIK3CA, or the P85BD domain (nt 103-335 of SEQ ID NO: 2) of PIK3CA.

Antisense constructs, antisense oligonucleotides, RNA interference constructs or siRNA duplex RNA molecules can be used to interfere with expression of PIK3CA. Typically at least 15, 17, 19, or 21 nucleotides of the complement of PIK3CA mRNA sequence are sufficient for an antisense molecule. Typically at least 19, 21, 22, or 23 nucleotides of PIK3CA are sufficient for an RNA interference molecule. Preferably an RNA interference molecule will have a 2 nucleotide 3' overhang. If the RNA interference molecule is expressed in a cell from a construct, for example from a hairpin molecule or from an inverted repeat of the desired PIK3CA sequence, then the endogenous cellular machinery will create the overhangs. siRNA molecules can be prepared by chemical synthesis, in vitro transcription, or digestion of long dsRNA by Rnase III or Dicer. These can be introduced into cells by transfection, electroporation, or other methods known in the art. See Hannon, G J, 2002, RNA Interference, *Nature* 418: 244-251; Bernstein E et al., 2002, The rest is silence. *RNA* 7: 1509-1521; Hutvagner G et al., RNAi: Nature abhors a double-strand. *Curr. Opin. Genetics & Development* 12: 225-232; Brummelkamp, 2002, A system for stable expression of short interfering RNAs in mammalian cells. *Science* 296: 550-553; Lee N S, Dohjima T, Bauer G, Li H, Li M-J, Ehsani A, Salvaterra P, and Rossi J. (2002). Expression of small interfering RNAs targeted against HIV-1 rev transcripts in human cells. *Nature Biotechnol.* 20:500-505; Miyagishi M, and Taira K. (2002). U6-promoter-driven siRNAs with four uridine 3' overhangs efficiently suppress targeted gene expression in mammalian cells. *Nature Biotechnol.* 20:497-500; Paddison P J, Caudy A A, Bernstein E, Hannon G J, and Conklin D S. (2002). Short hairpin RNAs (shRNAs) induce sequence-specific silencing in mammalian cells. *Genes & Dev.* 16:948-958; Paul C P, Good P D, Winer I, and Engelke D R. (2002). Effective expression of small interfering RNA in human cells. *Nature Biotechnol.* 20:505-508; Sui G, Soohoo C, Affar E-B, Gay F, Shi Y, Forrester W C, and Shi Y. (2002). A DNA vector-based RNAi technology to suppress gene expression in mammalian cells. *Proc. Natl. Acad. Sci. USA* 99(6):5515-5520; Yu J-Y, DeRuiter S L, and Turner D L. (2002). RNA interference by expression of short-interfering RNAs and hairpin RNAs in mammalian cells. *Proc. Natl. Acad. Sci. USA* 99(9):6047-6052.

Antisense or RNA interference molecules can be delivered in vitro to cells or in vivo, e.g., to tumors of a mammal. Typical delivery means known in the art can be used. For example, delivery to a tumor can be accomplished by intratumoral injections. Other modes of delivery can be used without limitation, including: intravenous, intramuscular, intraperitoneal, intraarterial, local delivery during surgery, endoscopic, subcutaneous, and per os. In a mouse model, the antisense or RNA interference can be adminstered to a tumor cell in vitro, and the tumor cell can be subsequently administered to a mouse. Vectors can be selected for desirable properties for any particular application. Vectors can be viral or plasmid. Adenoviral vectors are useful in this regard. Tissue-specific, cell-type specific, or otherwise regulatable promoters can be used to control the transcription of the inhibitory polynucleotide molecules. Non-viral carriers such as liposomes or nanospheres can also be used.

Using the p110α protein according to the invention, one of ordinary skill in the art can readily generate antibodies which specifically bind to the proteins. Such antibodies can be monoclonal or polyclonal. They can be chimeric, humanized, or totally human. Any functional fragment or derivative of an antibody can be used including Fab, Fab', Fab2, Fab'2, and single chain variable regions. So long as the fragment or derivative retains specificity of binding for the endothelial marker protein it can be used. Antibodies can be tested for specificity of binding by comparing binding to appropriate antigen to binding to irrelevant antigen or antigen mixture under a given set of conditions. If the antibody binds to the appropriate antigen at least 2, 5, 7, and preferably 10 times more than to irrelevant antigen or antigen mixture then it is considered to be specific.

Techniques for making such partially to fully human antibodies are known in the art and any such techniques can be used. According to one particularly preferred embodiment, fully human antibody sequences are made in a transgenic mouse which has been engineered to express human heavy and light chain antibody genes. Multiple strains of such transgenic mice have been made which can produce different classes of antibodies. B cells from transgenic mice which are producing a desirable antibody can be fused to make hybridoma cell lines for continuous production of the desired antibody. See for example, Nina D. Russel, Jose R. F. Corvalan, Michael L. Gallo, C. Geoffrey Davis, Liise-Anne Pirofski. Production of Protective Human Antipneumococcal Antibodies by Transgenic Mice with Human Immunoglobulin Loci *Infection and Immunity* April 2000, p. 1820-1826; Michael L. Gallo, Vladimir E. Ivanov, Aya Jakobovits, and C. Geoffrey Davis. The human immunoglobulin loci introduced into mice: V (D) and J gene segment usage similar to that of adult humans *European Journal of Immunology* 30: 534-540, 2000; Larry L. Green. Antibody engineering via genetic engineering of the mouse: XenoMouse strains are a vehicle for the facile generation of therapeutic human monoclonal antibodies *Journal of Immunological Methods* 231 11-23, 1999; Yang X-D, Corvalan J R F, Wang P, Roy C M-N and Davis C G. Fully Human Anti-interleukin-8 Monoclonal Antibodies: Potential Therapeutics for the Treatment of Inflammatory Disease States. *Journal of Leukocyte Biology* Vol. 66, pp 401-410 (1999); Yang X-D, Jia X-C, Corvalan J R F, Wang P, C G Davis and Jakobovits A. Eradication of Established Tumors by a Fully Human Monoclonal Antibody to the Epidermal Growth Factor Receptor without Concomitant Chemotherapy. *Cancer Research Vol.* 59, Number 6, pp1236-1243 (1999); Jakobovits A. Production and selection of antigen-specific fully human monoclonal antibodies from mice engineered with human Ig loci. *Advanced Drug Delivery Reviews* Vol. 31, pp: 33-42 (1998); Green L and Jakobovits A. Regulation of B cell development by variable gene complexity in mice reconstituted with human immunoglobulin yeast artificial chromosomes. *J. Exp. Med. Vol.* 188, Number 3, pp: 483-495 (1998); Jakobovits A. The long-awaited magic bullets: therapeutic human monoclonal antibodies from transgenic mice. *Exp. Opin. Invest. Drugs* Vol. 7(4), pp: 607-614 (1998); Tsuda H, Maynard-Currie K, Reid L, Yoshida T, Edamura K, Maeda N, Smithies O, Jakobovits A. Inactivation of Mouse HPRT locus by a 203-bp retrotransposon insertion and a 55-kb gene-targeted deletion: establishment of new HPRT-Deficient mouse embryonic stem cell lines. *Genomics* Vol. 42, pp: 413-421 (1997); Sherman-Gold, R. Monoclonal Antibodies: The Evolution from '80s Magic Bullets To Mature, Mainstream Applications as Clinical Therapeutics. *Genetic Engineering* News Vol. 17, Number 14 (August 1997); Mendez M, Green L, Corvalan J, Jia X-C, Maynard-Currie C, Yang X-d, Gallo M, Louie D, Lee D, Erickson K, Luna J, Roy C, Abderrahim H, Kirschenbaum F, Noguchi M, Smith D, Fukushima A, Hales J, Finer M, Davis C, Zsebo K, Jakobovits A. Functional transplant of megabase human immunoglobulin loci recapitulates human antibody response in mice. *Nature Genetics* Vol. 15, pp: 146-156 (1997); Jakobovits A. Mice engineered with human immunoglobulin YACs: A new technology for production of fully human antibodies for autoimmunity therapy. *Weir's Handbook of Experimental Immunology, The Integrated Immune System* Vol. IV, pp: 194.1-194.7 (1996); Jakobovits A. Production of fully human antibodies by transgenic mice. *Current Opinion in Biotechnology* Vol. 6, No. 5, pp: 561-566 (1995); Mendez M, Abderrahim H, Noguchi M, David N, Hardy M, Green L, Tsuda H, Yoast S, Maynard-Currie C, Garza D, Gemmill R, Jakobovits A, Klapholz S. Analysis of the structural integrity of YACs comprising human immunoglobulin genes in yeast and in embryonic stem cells. *Genomics* Vol. 26, pp: 294-307 (1995); Jakobovits A. YAC Vectors: Humanizing the mouse genome. *Current Biology* Vol. 4, No. 8, pp: 761-763 (1994); Arbones M, Ord D, Ley K, Ratech H, Maynard-Curry K, Otten G, Capon D, Tedder T. Lymphocyte homing and leukocyte rolling and migration are impaired in L-selectin-deficient mice. *Immunity* Vol. 1, No. 4, pp: 247-260 (1994); Green L, Hardy M, Maynard-Curry K, Tsuda H, Louie D, Mendez M, Abderrahim H, Noguchi M, Smith D, Zeng Y, et. al. Antigen-specific human monoclonal antibodies from mice engineered with human Ig heavy and light chain YACs. *Nature Genetics* Vol. 7, No. 1, pp: 13-21 (1994); Jakobovits A, Moore A, Green L, Vergara G, Maynard-Curry K, Austin H, Klapholz S. Germ-line transmission and expression of a human-derived yeast artificial chromosome. *Nature* Vol. 362, No. 6417, pp: 255-258 (1993); Jakobovits A, Vergara G, Kennedy J, Hales J, McGuinness R, Casentini-Borocz D, Brenner D, Otten G. Analysis of homozygous mutant chimeric mice: deletion of the immunoglobulin heavy-chain joining region blocks B-cell development and antibody production. *Proceedings of the National Academy of Sciences USA* Vol. 90, No. 6, pp: 2551-2555 (1993); Kucherlapati et al., U.S. Pat. No. 6,1075,181.

Antibodies can also be made using phage display techniques. Such techniques can be used to isolate an initial antibody or to generate variants with altered specificity or avidity characteristics. Single chain Fv can also be used as is convenient. They can be made from vaccinated transgenic mice, if desired. Antibodies can be produced in cell culture, in phage, or in various animals, including but not limited to cows, rabbits, goats, mice, rats, hamsters, guinea pigs, sheep, dogs, cats, monkeys, chimpanzees, apes.

Antibodies can be labeled with a detectable moiety such as a radioactive atom, a chromophore, a fluorophore, or the like. Such labeled antibodies can be used for diagnostic techniques, either in vivo, or in an isolated test sample. Antibodies can also be conjugated, for example, to a pharmaceutical agent, such as chemotherapeutic drug or a toxin. They can be linked to a cytokine, to a ligand, to another antibody. Suitable agents for coupling to antibodies to achieve an anti-tumor effect include cytokines, such as interleukin 2 (IL-2) and Tumor Necrosis Factor (TNF); photosensitizers, for use in photodynamic therapy, including aluminum (III) phthalocyanine tetrasulfonate, hematoporphyrin, and phthalocyanine; radionuclides, such as iodine-131 ($^{131}$I), yttrium-90 ($^{90}$Y), bismuth-212 ($^{212}$Bi), bismuth-213 ($^{213}$Bi), technetium-99m ($^{99m}$Tc), rhenium-186 ($^{186}$Re), and rhenium-188 ($^{188}$Re); antibiotics, such as doxorubicin, adriamycin, daunorubicin, methotrexate, daunomycin, neocarzinostatin, and carboplatin; bacterial, plant, and other toxins, such as diphtheria toxin, pseudomonas exotoxin A, staphylococcal enterotoxin A, abrin-A toxin, ricin A (deglycosylated ricin A and native ricin A), TGF-alpha toxin, cytotoxin from chinese cobra (naja naja atra), and gelonin (a plant toxin); ribosome inactivating proteins from plants, bacteria and fungi, such as restrictocin (a ribosome inactivating protein produced by *Aspergillus restrictus*), saporin (a ribosome inactivating protein from *Saponaria officinalis*), and RNase; tyrosine kinase inhibitors; ly207702 (a difluorinated purine nucleoside); liposomes containing antitumor agents (e.g. antisense oligonucleotides, plasmids which encode for toxins, methotrexate, etc.); and other antibodies or antibody fragments, such as F(ab).

Those of skill in the art will readily understand and be able to make such antibody derivatives, as they are well known in the art. The antibodies may be cytotoxic on their own, or they may be used to deliver cytotoxic agents to particular locations in the body. The antibodies can be administered to individuals in need thereof as a form of passive immunization.

Given the success of small molecule protein kinase inhibitors, one can develop specific or non-specific inhibitors of p110α for treatment of the large number of patients with these mutations or cancers generally. It is clearly possible to develop broad-spectrum PI3K inhibitors, as documented by studies of LY294002 and wortmannin (2, 21, 22). Our data suggest that the development of more specific inhibitors that target p110α but not other PI3Ks would be worthwhile.

Candidate chemotherapeutic agents can be identified as agents which inhibit p110α activity or expression. Test compounds can be synthetic or naturally occurring. They can be previously identified to have physiological activity or not. Tests on candidate chemotherapeutic agents can be run in cell-free systems or in whole cells. p110α activity can be tested by any means known in the art. These include methods taught in references 2, 22 and in Truitt et al., J. Exp. Med., 179, 1071-1076 (1994). Expression can be monitored by determining PI3KCA protein or mRNA. Antibody methods such as western blotting can be used to determine protein. Northern blotting can be used to measure mRNA. Other methods can be used without limitation. When testing for chemotherapeutic agents, the p110α used in the assay can be a wild-type or an activated form. The activated form may contain a substitution mutation selected from the group consisting of E542K, E545K, Q546K, and H1047R. Moreover, inhibitors can be tested to determine their specificity for either p110α or an activated form of p110α. Comparative tests can be run against similar enzymes including PIK3CB, PIK3CG, PIK3C2A, PIK3C2B, PIK3C2G, PIK3C3, A-TM, ATR, FRAP1, LAT1-3TM, SMG1, PRKDC, and TRRAP to determine the relative specificity for the p110α enzyme.

Once a non-synonymous, intragenic mutation in a PIK3 CA coding sequence is identified in a test tissue of a patient, that information can be used to make therapeutic decisions. Patients with such mutations are good candidates for therapy with a p110α inhibitor. Such inhibitors can be specific or general for the family of inhibitors. Such inhibitors include LY294002 and wortmannin. Such inhibitors further include molecules comprising an antibody binding region specific for p110α. Such molecules are discussed above.

Sets of primers for amplifying and/or sequencing PIK3CA can be provided in kits or assembled from components. Useful sets include pairs of forward and reverse primers optionally teamed with sequencing primers. The forward primers are shown in SEQ ID NO: 6 to 158. The reverse primers are shown in SEQ ID NO: 159 to 310. The sequencing primers are shown in: SEQ ID NO: 311 to 461. Pairs or triplets or combinations of these pairs or triplets can be packaged and used together to amplify and/or sequence parts of the PIK3CA gene. Pairs can be packaged in single or divided containers. Instructions for using the primers according to the methods of the present invention can be provided in any medium which is convenient, including paper, electronic, or a world-wide web address.

While the invention has been described with respect to specific examples including presently preferred modes of carrying out the invention, those skilled in the art will appreciate that there are numerous variations and permutations of the above described systems and techniques that fall within the spirit and scope of the invention as set forth in the appended claims.

EXAMPLES

Example 1

This Example Demonstrates that the PIK3CA Gene is the Predominant Target of Mutations in this Gene Family To evaluate whether PI3Ks is genetically implicated in tumorigenesis, we directly examined the DNA sequences of members of this gene family in colorectal cancers.

PI3K catalytic subunits are divided into three major classes depending on their substrate specificity (5). Additionally, a set of more distantly related proteins, including members of the mTOR family, constitute a fourth class (6). We used Hidden Markov models to identify 15 human genes containing kinase domains related to those of known PI3Ks in the human genome (7). These comprised seven PI3Ks, six members of the mTOR subfamily and two uncharacterized PI3K-like genes (Table 1).

TABLE 1

PI3K genes analyzed

| Gene name | Celera Accession | Genbank Accession | Alternate names | Group* |
|---|---|---|---|---|
| PIK3CA | hCT1640694 | NM_006218 | p110-alpha | Class IA |
| PIK3CB | hCT7084 | NM_006219 | PIK3C1, p110-beta | Class IA |
| PIK3CD | hCT2292011 | NM_005026 | p110-delta | Class IA |
| PIK3CG | hCT7976 | NM_002649 | PI3CG, PI3K-gamma | Class IB |
| PIK3C2A | hCT2270768 | NM_002645 | CPK, PI3-K-C2A, PI3K-C2alpha | Class II |
| PIK3C2B | hCT7448 | NM_002646 | C2-PI3K, PI3K-C2beta | Class II |
| PIK3C2G | hCT1951422 | NM_004570 | PI3K-C2-gamma | Class II |
| PIK3C3 | hCT13660 | NM_002647 | Vps34 | Class III |
| ATM | hCT29277 | NM_000051 | AT1, ATA, ATC, ATD, ATE, ATDC | Class IV |
| ATR | hCT1951523 | NM_001184 | FRP1, SCKL, SCKL1 | Class IV |
| FRAP1 | hCT2292935 | NM_004958 | FRAP, MTOR, FRAP2, RAFT1, RAPT1 | Class IV |
| SMG1 | hCT2273636 | NM_014006 | ATX, LIP, KIAA0421 | Class IV |
| PRKDC | hCT2257127 | NM_006904 | p350, DNAPK, DNPK1, HYRC1, XRCC7 | Class IV |
| TRRAP | hCT32594 | NM_003496 | TR-AP, PAF400 | Class IV |
| none | hCT2257641 | none | | Class IV |
| none | hCT13051 | none | | Class IV |

*PI3K genes are grouped into previously described classes (S3, S4). Class I, II and III comprise PI3K catalytic subunits, while class IV comprises PI3K-like genes including members of the mTOR (target of rapamycin), ATM (ataxia telangiectasia mutated), and DNAPK (DNA-dependent protein kinase) subfamilies, as well as two previously uncharacterized genes.

We initially examined 111 exons encoding the predicted kinase domains of these genes (Table 2). The exons were polymerase chain reaction (PCR) amplified and directly sequenced from genomic DNA of 35 colorectal cancers (8). Only one of the genes (PIK3CA) contained any somatic (i.e., tumor-specific) mutations.

TABLE 2

Primers used for PCR amplification and sequencing

| Gene and Exon Name | Forward Primer[1] | Reverse primer[2] | Sequencing Primer[3] |
|---|---|---|---|
| hCT2270768-Ex21 | TTCCAGCCTGGGTAACAAAG | CGTCAGAACAAGACCCTGTG | AAAGGGGAAATGCGTAGGAC |
| hCT2270768-Ex22 | CCTGACCTCAGGTGTTCTGC | CCCGGCCACTAAGTTATTTTC | TCCCAAAGTGCTGGGATTAC |
| hCT2270768-Ex23 | TGCACATTCTGCACGTGTATC | CTGCCATTAAATGCGTCTTG | CCAGAACTTAAAGTGAAATTTAAAAAG |
| hCT2270768-Ex24 | TCCCAGTTTGTATGCTATTGAGAG | CTTTGGGCCTTTTTCATTCC | GCGAGGCAAAACACAAAGC |
| hCT2270768-Ex25 | TGGAAATTCAAAAGTGTGTGG | TGTCTGGCTTATTTCACACG | TTGGAAATGGCTGTACCTCAG |
| hCT2270768-Ex26 | CACTAATGAACCCCTCAAGACTG | AACTTTTGACAGCCTACTATGTGC | TACTTGAGCAGCCCACAGG |
| hCT2270768-Ex27-1 | TCCTTGGCAAAGTGACAATC | GACCATTCATGAAAGAAACAAGC | AAAGGAATGAAAGTGGTTTTTGTC |
| hCT13660-Ex16 | CTCTCACATACAACACCATCTCC | CCATGTACCGGTAACAAAAGAAG | TGCAATGTAATAGTTTTCCAAGG |
| hCT13660-Ex17 | ATGTATCTCATTGAAAACCCAAC | TGAGCTTTCTAGGATCGTACCTG | CAGCAAATGAACTAAGCCACAG |
| hCT13660-Ex18 | TCCCAAAGTGCTGGGATTAC | GCAGGAAGGTCCAACTTGTC | TGCTATACTATTTGCCCACAAAAC |
| hCT13660-Ex19 | CCTATGACATAAATGCCAGTACAAAC | ATCTTCAACTGCGAACATGC | GAATGCATTTATTCAGAGATGAGG |
| hCT13660-Ex20 | TCTTTTGTTCAGTCAGCATCTCTC | AAGCATCAATGACTACTTTAATCAAC | TGCTAGACACTTGCTGGTCAC |
| hCT13660-Ex21 | TTGAGAATTCAGATGAGAAACCAG | TCCCAAAGTGCTGGGATTAC | TTGATATTAAAGTTGCACAAACTGC |
| hCT13660-Ex22 | GAAGGCCACTCTCAAACCTG | TTGTTGCCTTTGTCATTTTG | TCAATTGTGTGACATATCACCTACC |
| hCT13660-Ex23 | TCAAGGCTTGCATTTCATTG | ATGTGACTGTGGGCAGGAAC | TCACTGTAGAAATCCAAGTACCAC |
| hCT13660-Ex24 | TTCCACACTCCAAAGAATGC | GCTGGTGAGATGTCAAAACG | TCTGCATCAGTTTGATTCTGC |
| hCT13660-Ex25-1 | AATTGCAATCCTCTTGGTAGC | TCAACATATTACTTCCTCCAGAAGTC | AATGCACTTTTTATTTTATTAG |
| hCT32594-Ex66-2 | GCCAAGACCAAGCAACTCC | TTCTCCCATGTCAGGGAATC | GAAAAGTGCCGGTTCTTGAG |
| hCT32594-Ex67-1 | ATAAACGACCGCTGGCCTAC | GACCCTCAAAGGCTAACGTG | GCCTACACAGTCCGTTTTCC |
| hCT32594-Ex67-2 | GTACATCCGGGGACACAATG | TCCCTGGTCAGCACAGACTAC | AGAGGAGCGTGTGTTGCAG |
| hCT32594-Ex68 | ACCGGGTTCTTCCAGCTAAG | AGCTGTCTCATTTCCACCATC | ACTCTGACGGTGGAGCTGAG |
| hCT32594-Ex69-1 | CAATGCGTGCGTTAAATCTG | CGCGTCGTTTATGTCAAATC | GCTCTTGGTGCTAAGTTAAAGAGG |
| hCT32594-Ex69-2 | CCCAATGCCACGGACTAC | CGCGTCGTTTATGTCAAATC | ATCCAGCTGGCTCTGATAGG |
| hCT32594-Ex70 | ATCCAGCTGGCTCTGATAGG | CATAACACACAGGGGTGCTG | TGAACAGCCAGATCCTCTCC |
| hCT32594-Ex71 | CTGGTGCTGAAACTCGACTG | GAACTGGGCGAGGTTGTG | GTCCCACCTTGTTAGGAAGC |
| hCT32594-Ex72-1 | GTCTCGTTCTCTCCCTCACG | TCCCTTTCTTACACGCAAAC | TGGCATTCTGAAAACGGTTC |
| hCT32594-Ex72-2 | CACAACCTCGCCCAGTTC | CAGTTCCGCCTGTACATTCAC | GCAACAGCCTGGACAATC |
| hCT7976-Ex5 | AGCATCACCCTCAGAGCATAC | AGCGCTCCTGCTTTCAGTC | CACATATTTCTGTCCCCTGTTG |
| hCT7976-Ex6 | TGCCATACCTCTTAGGCACTTC | GTCTTGGCGCAGATCATCAC | TGTGGTTCTTTGGAGCACAG |
| hCT7976-Ex7 | CGACAGAGCAAGATTCCATC | TTTTGTCACCAGTTGAAATGC | CCAAGGTACATTTCGGAAAAC |
| hCT7976-Ex8 | AGATTGCCATCTGAGGAAGG | GACTGGGAAAAGCATGAGC | ACCAGCCCTTTCCTCTTGTC |
| hC17976-Ex9 | GCATGGAGAGGAAGTGAACC | CGGTGATCATAATATTGTCATTGTG | TTCTTCCTCATGCCATTGTG |
| hCT7976-Ex10 | TGGCCAGAGAGTTTGATTTATG | GGAAGTGTGGGCTTGTCTTC | GTGGCATCTGGCTGTCATC |
| hCT7976-Ex11-1 | CCCTCAATCTCTTGGGAAAG | TGCACAGTCCATCCTTTGTC | CAATTAGTTTTCCTTGAGCACTCC |
| hCT7976-Ex11-2 | TGGTTTCTTCTCATGGACAGG | AATGCCAGCTTTCACAATGTC | TCTTCTTTATCCAGGACATCTGTG |
| hCT7448-Ex21 | GGGTGTCCACACTTCTCAGG | GGCCAAGACCACATGGTAAG | CCTGGGAGAGGTCTGGTTC |

TABLE 2-continued

Primers used for PCR amplification and sequencing

| Gene and Exon Name | Forward Primer[1] | Reverse primer[2] | Sequencing Primer[3] |
|---|---|---|---|
| hCT7448-Ex22 | CCGGAAGAAACAATGAGCAG | TCCTACATTAAGACAGCATGGAAC | GGCAGCATCTTGGTCTGAAG |
| hCT7448-Ex23 | GGTGTGAGCTGAGTGAGCAG | TGCCTCCCTTTTAAGGCTATC | GAGCACTTGGGAGACCTGAG |
| hCT7448-Ex24 | GTGGGAATGACCTTCCTTTC | AGGTCCTTCTGCCAACAAAG | AGGGAAGCATGAGCACAGTC |
| hCT7448-Ex25 | GGATGAACAGGCAGATGTGAG | CGTCTTCTCTCCTCCAATGC | TGAGTTCTGTCTGGCTGTGG |
| hCT7448-Ex26 | AGCCCCTTCTATCCAGTGTG | GGTATTCAGTTGGGGCTCAG | TGATGAGGGATGAGGGAAAC |
| hCT7448-Ex27 | TGCCCACAGCATCTGTCTAC | TGTATCCACGTGGTCAGCTC | AGGGTTAGGGAGCCTAGCTG |
| hCT7448-Ex28-1 | ATTGTGTGCCAGTCATTTGC | ACAGGACGCTCGGTCAAC | TCCTTGGAACACCCCTGTC |
| hCT1951523-Ex39-2 | TTCCACATTAAGCATGAGCAC | TTGCCATCAGTACAAATGAGTTTAG | CAGTCATGATACCTACACTTCCATC |
| hCT1951523-Ex40 | GACAGTCATTCTTTTCATAGGTCATAG | TTCCTGCTTTTTAAGAGTGATCTG | CAACTCTGAAATAAAAGCAATCTGG |
| hCT1951523-Ex41 | CCACATAGTAAGCCTTCAATGAC | AGGAAGGAAGGGATGGAAAC | TTCTTTGGTTATGAAATGAACAATC |
| hCT1951523-Ex42 | TGAAAATGTTCCTTTATTCTTG | AGAAACCACTCATGAAAA | TTGAATAAAAGTAGATGTTTCTTGTCC |
| hCT1951523-Ex43 | TCTGAGAACATTCCCTGATCC | CGCATTACTACATGATCCACTG | TACCAAGAATATAATACGTTGTTATGG |
| hCT2257127-Ex76 | TCAGCTCTCTAATCCTGAACTGC | TGTCACAGAAAGCATGAGACC | CGGCTTCTGGCACATAAAAC |
| hCT2257127-Ex77-1 | AGCAGAGAAGAAACATATACCAT | AGAAATAACTGTCAATATCCCAGTATCAC | CCATTGAGCACTCCATTCATTAC |
| hCT2257127-Ex77-2 | CATTTTGGGAAAGGAGGTTC | TCATTAAACATTTAGTAATGTGTGCTC | CCCTGGGAATCTGAAAGAATG |
| hCT2257127-Ex78 | ATTACAGGCGTGAGCCACTG | AGGCAACAGGGCAAGACTC | TGGGCCGTTGTCTCATATAC |
| hCT2257127-Ex79-1 | TTTGGCACTGTCTTCAGAGG | CCTGAAAGGGAGAATAAAAGG | CACTCTGGCTTTCCCTCTG |
| hCT2257127-Ex79-2 | AGAGGGAACACCCTTTCCTG | CCTGAAAGGGAGAATAAAAGG | AGGTCATGAATGGGATCCTG |
| hCT2257127-Ex80 | TATAGCGTTGTGCCCATGAC | TATTGACCCAGCCAGCAGAC | CATATTGCTTGGCGTCCAC |
| hCT2257127-Ex81 | TCCTGCCTCTTTGCTATTTTCAATG | TATATTGAGACTCAAATATCGA | TCTTGGTGATCTTTGCCTTTG |
| hCT2257127-Ex82 | TTGCCTCAGAGAGATCATCAAG | TGATGCATATCAGAGCGTGAG | TCATCAAGATTATTCGATATTTGAGTC |
| hCT2257127-Ex83-1 | TAGGGGCGCTAATCGTACTG | TTCAATGACCATGACAAAACG | CGAGAAAGTAAAGTGCCTGCTG |
| hCT2257127-Ex83-2 | TCTGATATGCATCAGCCACTG | TTCAATGACCATGACAAAACG | CGGGATTGGAGACAGACATC |
| hCT2257127-Ex84 | TGATTTCAAGGGAAGCAGAG | TGGTTTTCAAGCAGACAATCC | GAGGATGCTGCCATTTGTG |
| hCT2257127-Ex85 | TGTAGAAAGCAAGGCTGCTC | TCCTCCTCAATGAAAGCAGAG | CATGCTAACAGAGTGTCAAGAGC |
| hCT1951422-Ex19 | ACCCCAAAGTCATCCAAGTG | CAATGTGATCCCAACTGGTC | CGAATTCTTTTTGCCATTTC |
| hCT1951422-Ex20 | AAAGGCTCCAGTTGATGGAC | TTATTGCCAATTGGAGTTTGG | AAAGTCTGCAAGGGGCTATG |
| hCT1951422-Ex21 | CCATTAAAACCACTCTAAGTCAGG | TTCTGTTGGCTTATCATTTTTG | TCAGGCTAGAAATGTATCCAAGG |
| hCT1951422-Ex22 | AAGCCTCCTCCAGAAAAGAAG | CCCAGAAACTAAATAAAATGCAG | AAAGGAAGGGGTAATCCAG |
| hCT1951422-Ex23 | CCCTCCTGTCCACTGAGATG | AATCAAATTTGTTGCATTAAAAATC | TTTACTTTTTATGATTACCTCTGATGC |
| hCT1951422-Ex24 | TCTCAAGCTGCCTCACAATG | GTTTTCTCATTCCTTTCTCTTCC | AAAGAAAATTCAAATGAAAATAAGTCG |
| hCT1951422-Ex25 | AAAGACATTGCCATGCAAAC | TTTGGGAAAGGGAACACAAG | CATGCAAACTTGGGTCTAGATG |
| hCT1951422-Ex26 | TTGTTGGGCTCCAAATAAAC | GATTTTCCTTGGAACATCCTC | TTGGCTTTTCCCCTCATAC |
| hCT13051-Ex5 | CCCTGGAGTGCTTACATGAG | CGGGGATCAGATTTGCTATG | TAAAGCCTTTCCCAGCTCAG |
| hCT13051-Ex6 | GACTTTATAAACACTCGACATTAGAGC | TAGGGGGTCATCCTCAGGTG | CCTGCTGCTTCCACAGGAC |
| hCT13051-Ex7 | ATGATGACCTCTGGCAGGAC | GTCTTCCCCTGCTCAATCAC | CATGGACGTCCTGTGGAAG |
| hCT13051-Ex8 | GAATCAACCGTCAGCGTGTC | GACACGTTGTGGGCCAGCCAGT | GTGTCCCATTCATCCTCACC |
| hCT13051-Ex9 | CTGGCACCGGGGAAAACAGAG | CTGCCGGTTATCTTCGGACACGTT | AACAGAGGAGGCGCTGAAG |

TABLE 2-continued

Primers used for PCR amplification and sequencing

| Gene and Exon Name | Forward Primer[1] | Reverse primer[2] | Sequencing Primer[3] |
|---|---|---|---|
| hCT2282983-Ex40 | TGGACATCGACTACAAGTCTGG | TGAGTGAGGGCAGACAGATG | GCCTCACCCTACCCATCC |
| hCT2282983-Ex41 | TCCTTGGGGTTTTGAAGAAG | TGGCACCTGAACCATGTAAG | AGATTGCTGGGGTTCCTTTC |
| hCT2282983-Ex42 | AAGGCCTTCCAGACTCTTGC | CGTACATGCCGAAGTCTGTC | CCACCTCACTCCATCTCTGG |
| hCT2282983-Ex43 | CCTCTTTGTTTTTCCCTACCG | GCCCTGGTTTTAACCCTTAAC | TGGGGTAAGTTCCCTGAGTG |
| hCT2282983-Ex44-1 | CTTCCACAGTGGGGGTACAG | CCAGCTCCAGCTTCTGACTC | TACAGAGCCAGGGAGAGTGC |
| hCT2282983-Ex44-2 | GACACAACGGCAACATTATGCTG | TTGTGTTTTCTTGGAGACAG | TATCATCCACATCGGTCAGC |
| hCT2292935-Ex46 | CATTCCAAAGCATCTGGTTTTAC | CAATGAGCATGGGAGAGATG | TTTGGGACAAGTAATTGTTATTAGC |
| hCT2292935-Ex47 | TTGTGAGGAACGTGTGATTAGG | TGGAGTTTCTGGGACTACAGG | TTGAATGCAGTGGTGCTCTC |
| hCT2292935-Ex48 | CTGGGCAACAGAGCAAGAC | CCTTCTTCAAAGCTGATTCTCTC | TCTGCCTGTGTTCTGAGCTG |
| hCT2292935-Ex49 | TCCCTTCTCCTTTGGCTATG | CGCTCTACAGCCAATCACAG | GAACTCAGCTCTGCCTGGAC |
| hCT2292935-Ex50 | ATAGCACCACTGCCTTCCAG | TGGCATCACAATCAATAGGG | GCGAGACTCGGTCTCAAAAG |
| hCT2292935-Ex51 | TGCAGAAGTGGAGGTGGAG | CTCCAAGGGGGTTAGAGTCC | ATCGTTTGCCAACTCCTAGC |
| hCT2292935-Ex52 | AACCCAAGCTGCTTCCTTTC | CAGGAAACCAGGTCAGAAGTG | AATCAGTGCAGGTGATGCAG |
| hCT2292935-Ex53 | AGTCCTGCCCTGATTCCTTC | TTTTTGCAGAAAGGGGTCTTAC | ACATGGCCTGTGTCTGCTTC |
| hCT2292935-Ex54 | CCCACCCACTTATTCCTGAG | GCCCACCCCACTCTAGAAAC | GACTGGAAGAAAATAACCAAGTTTC |
| hCT2292935-Ex55 | TTTCCCCTTTAGGGTAGGTAGG | TGGAACCTTTCTGCTCAAAG | GGCAGGCGTTAAAGGAATAG |
| hCT2292935-Ex56 | CGGACATAGAGGAAGGATTGC | AGCTGCATGGTGCCAAAG | AAAAACAGGGCACCCATTG |
| hCT2292935-Ex57 | TGGCCAAACTTTTCAAATCC | ATAACAATGGGCACATGCAG | TTAAGCCCACAGGGAACAAG |
| hCT2292935-Ex58-1 | TGGGAGAGCTCAGGGAATAC | GGTCATTCTTCCATCAGCAAG | TGTGAGACCTTGGCCTTTTC |
| hCT2273636-Ex35-1 | TCCCAAAGTGCTGGGATTAC | CACACCCACACTCAGACAAAG | TCTTCTGAAAAATGGAGGAAGTC |
| hCT2273636-Ex35-2 | TTGGCTGCCATGACTAACAC | GGCACTGCAGGCTAATAATG | GCTCTTCCTGGGGAAGTCTC |
| hCT2273636-Ex36-1 | GCTCTCAGTGTGCCTCATGG | GGGACGTCAAGTCTTTTCCTTC | CAGTTTTTGACTGCCACTGC |
| hCT2273636-Ex36-2 | AAGAAACACCCCGGTTCC | GGGACCTCAAGTCTTTTCCTTG | TCCATGCTCGACACTATTCTG |
| hCT2273636-Ex37-1 | AAATTTAGTTGAGTAATGAGAGAATGC | GGAAGGGAAGGAGGACAAAC | TTCTACTTTACATACAAAAGGCACTC |
| hCT2273636-Ex37-2 | GTAAAATTGGCCCTGCTTTG | CGTCTCAAACTACCAAGTCTGG | AGTTGGGCTTAGCCTGGATG |
| hCT2273636-Ex38 | CATAACCACATGCAGCAACC | CACCCAGTGCTGTTTCAATG | AGTATCACGTCCATGTTGGAG |
| hCT2273636-Ex39 | AATTGGCCTTGGAGACAGAC | CGCCGCATAATGTGTAAAAC | CAATGTTTGCTTTGAAAAGG |
| hCT2273636-Ex40-1 | TTCATGTGAGCAGGTATGCTG | TGCCATATTTAACTGCCATTTC | TGAGCAAAACCTGTGGAATG |
| hCT2273636-Ex40-2 | TTGTGTACGACCCTCTGGTG | TGCCATATTTAACTGCCATTTC | TTTGCTGGTGCTGTCTATGG |
| hCT2273636-Ex41 | TTTGTACAGTGGAGGCAACG | GCAGTCACTGAGACAGCTTTTATC | GGATGTGCAAAATGTTCTTCTG |
| hCT7084-Ex17 | CAGCTGGTTATGTGTGTTATGG | TAAGCATAGCCTCGGAGAAC | GGGAGCAGGTGTTATTGATTG |
| hCT7084-Ex18 | TGTCCTCATGGTTGCTTTTC | GGACCATTAATAGCTACCTTCCTG | GGTGAGGAGTTTTCCCAAGC |
| hCT7084-Ex19 | CAGGGACATGCTATCCAAAG | AGGCAAGACAACATATTTGAAAG | AGCAGAGAGTTTGTTAATGTTTTTAG |
| hCT7084-Ex20 | TGGTGGAACTTGTGTTTTCC | AAGGGCTATGTGTCATTTTGTTC | GCTGACTTCTATTGGGAGCATAC |
| hCT7084-Ex21 | TCATACGGTTTTGGCAGCTC | CATCAAGCAAGCAAACAAATG | CAGAGGTATGGTTTGGGTCTC |
| hCT7084-Ex22 | ACAGAGGGAGAAGGGCTCAG | AATTCCCCCAAAAGCTTCC | TGGGGTCTAGGACTATGGAG |
| hCT7084-Ex23 | TGGGACAATTTCGCAGAAG | TTCCTCCTGGCTAAGAACC | GCTGTGTTTTCTTAATTTCCTGTATG |
| hCT7084-Ex24-1 | ATGAAAGCATGCTGCCTGATG | AAAAGCAGAGGGAATCATCG | CAGCCTCCTGCAGACTTTG |

TABLE 2-continued

Primers used for PCR amplification and sequencing

| Gene and Exon Name | Forward Primer[1] | Reverse primer[2] | Sequencing Primer[3] |
|---|---|---|---|
| hCT2257641-Ex1-56 | GGGGGCCTTTAGAAGGAAG | TCCCATTCATGACCTGGAAG | CATTTTGGGAAAGGAGGTTC |
| hCT2257641-Ex1-57 | TGGAGTTCCTGAGAAATGAGC | GGCCCGCTTTAAGAGATCAG | CGGTCAGTATGACGGTAGGG |
| hCT2257641-Ex1-58 | AGAGGGAACACCCTTTCCTG | CATGCCCAAAGTCGATCC | AGGTCATGAATGGGATCCTG |
| hCT2257641-Ex1-59 | CATGATGTTGGAGCTTACATGC | ACACATCCATGGTGTTGGTG | GGCGCTAATCGTACTGAAAC |
| hCT2257641-Ex1-60 | CGGGATTGGAGACAGACATC | TGCCACAGCCACATAGTCTC | TATGGTGGCCATGGAGACTG |
| hCT2257641-Ex1-61 | CATCATGGTACACGCACTCC | TTCTATCTGCAGACTCCACAG | AGGAGCCCTCCTTTGATTG |
| hCT29277-Ex55 | CTCAATCAGAGCCTGAACCAC | GGAAAGAAAGCAGGAGAAGC | GGCCAGTGGTATCTGCTGAC |
| hCT29277-Ex56 | CCCGGCCTAAAGTTGTAGTTC | AAATGGAGAAAAGCCTGGTTC | AAGACAAAATCCCAAATAAAGCAG |
| hCT29277-Ex57 | TGGGAGACTGTCAAGAGGTG | AAGCAATCCTCCCACCTTG | ATTGGTTTGAGTGCCCTTTG |
| hCT29277-Ex58 | TTCCTCCAAGGAGCTTTGTC | CCTTCCTTTTCACTCACACAC | AAAATGCTTTGCACTGACTCTG |
| hCT29277-Ex59 | TTCCCTGTCCAGACTGTTAGC | TGATTAATAATGAAGATGGGTTGG | TTCATCTTTATTGCCCCTATATCTG |
| hCT29277-Ex60 | CCGGTTATGCACATCATTTAAG | ACTCAGTACCCCAGGCAGAG | TTAAAGATTATACCAAGTCAGTGGTC |
| hCT29277-Ex61 | GCAGCCAGAGCAGAAGTAAAC | TCAAACTCCTGGGCTCAAAC | CATGTGGTTTCTTGCCTTTG |
| hCT29277-Ex62 | TCTAATGAAAGCCCACTCTGC | CAGCCACATCCCCCTATG | AAGCATAGGCTCAGCATACTACAC |
| hCT29277-Ex63 | AAGTGTGCATGATGTTTGTTCC | TGCCTTCTTCCACTCCTTTC | CCCATCAACTACCATGTGACTG |
| hCT29277-Ex64-1 | GATGACCAAGAATGCAAACG | AAGAGTGAAAGCAGAGATGTTCC | GGTCCTGTTGTCAGTTTTTCAG |
| NM_005026 Ex17 | ATCATCTTTAAGAACGGGGATGG | ACTAAGCCTCAGGAGCAGCCT | GGTCCTGGGGTGCTCCTAGA |
| NM_005026 Ex18 | CCTCAGATGCTGGTGCCG | GATACTTGGGGAAGAGAGACCTACC | TCCTCAACTGAGCCAAGTAGCC |
| NM_005026 Ex19 | TCTTCATGCCTTGGCTCTGG | GAGGGGAGAGGAGGGGGAG | TGTGTCCTCCATGTTCTGTTGG |
| NM_005026 Ex20 | TCCGAGAGAGTGGGCAGGTA | CACAAACCTGCCCACATTGC | TGGCCCCTCTGCCTAGCA |
| NM_005026 Ex21 | GGGCAGGTTTGTGGGTCAT | CCTGGGCGGCTCAACTCT | CCACTGCTGGGTCCTGGG |
| NM_005026 Ex22 | GGAACTGGGGGCTCTGGG | AGGCGTTTCCGTTTATGGC | GAATAGAGAGCTTTTCCTGAGATGC |
| hCT1640694-Ex1-1 | GTTTCTGCTTTGGGACAACCAT | CTGCTTCTTGAGTAACACTTACG | GATTCATCTTGAAGAAGTTGATGG |
| hCT1640694-Ex1-2 | CTCCACGACCATCATCAGG | GATTACGAAGGTATTGGTTTAGACAG | ACTTGATGCCCCAAGAATC |
| hCT1640694-Ex1-3 | CCCCCTCCATCAACTTCTTC | GGTGTTAAAAATAGTTCCATAGTTCG | CTCAAGAAGCAGAAAGGGAAG |
| hCT1640694-Ex2-1 | TCATCAAAAATTTGTTTTAACCTAGC | TATAAGCAGTCCCTGCCTTC | TCTACAGAGTTCCCTGTTTGC |
| hCT1640694-Ex2-2 | TTCTGAACGTTTGTAAAGAAGCTG | TATAAGCAGTCCCTGCCTTC | GCTGTGGATCTTAGGGACCTC |
| hCT1640694-Ex3-1 | GCAGCCCGCTCAGATATAAAC | CTGGGCGAGAGTGAGATTCC | AAAAGCATTTCTGATATGGATAAAG |
| hCT1640694-Ex3-2 | TCTGAAAATCAACCATGACTGTG | ATGAACCCAGGAGGCAGAG | TCGAAGTATGTTGCTATCCTCTG |
| hCT1640694-Ex4-1 | TCTTGTGCTTCAACGTAAATCC | CGGAGATTTGGATGTTCTCC | AAAATAATAAGCATCAGCATTTGAC |
| hCT1640694-Ex4-2 | TCTCAACTGCCAATGGACTG | CGGAGATTTGGATGTTCTCC | TTATTCCAGACGCATTTCCAC |
| hCT1640694-Ex5 | TAGTGGATGAAGGCAGCAAC | TTTGTAGAAATGGGGTGTTGC | TTTGAGTCTATCGAGTGTGTGC |
| hCT1640694-Ex6 | TGCCTTTTCCAATCAATCTC | AATTCCTGAAGCTCTCCCAAG | TTCCTGTTTTTCGTTTGGTTG |
| hCT1640694-Ex7 | GGGGAAAAAAGGAAAGAATGG | TGCTGAACCAGTCAAACTCC | TGAATTTCCTTTTGGGGAAG |
| hCT1640694-Ex8 | TTTGCTGAACCCTATTGGTG | TTGCAATATTGGTCCTAGAGTTC | TGGATCAATCCAAATAAAGTAAGG |
| hCT1640694-Ex9 | GATTGGTTCTTTCCTGTCTCTG | CCACAAATATCAATTTACAACCATTG | TTGCTTTTTCTGTAAATCATCTGTG |
| hCT1640694-Ex10 | ACCTTTTGAACAGCATGCAA | TGGAAATAATGTTAAGGGTGTTTTT | TATTTCATTTATTTATGTGGAC |
| hCT1640694-Ex11 | AAAACACCCTTAACATTATTTCCATAG | TCTGCATGGCCGATCTAAAG | GAAGTTAAGGCAGTGTTTTAGATGG |

TABLE 2-continued

Primers used for PCR amplification and sequencing

| Gene and Exon Name | Forward Primer[1] | Reverse primer[2] | Sequencing Primer[3] |
|---|---|---|---|
| hCT1640694-Ex12 | TTATTCTAGATCCATACAACTTCCTTT | AAAGTTGAGAAGCTCATCACTGGTAC | ACCAGTAATATCCACTTTCTTTCTG |
| hCT1640694-Ex13 | CTGAAACTCATGGTGGTTTTG | TGGTTCCAAATCCTAATCTGC | TTTATTGGATTTCAAAAATGAGTG |
| hCT1640694-Ex14 | GAGTGTTGCTGCTCTGTGTTG | TTGAGGGTAGGAGAATGAGAGAG | TCTCATGTGAGAAAGAGATTAGCAG |
| hCT1640694-Ex15 | GGATTCCTAAATAAAAATTGAGGTG | CATGCATATTTCAAAGGTCAAG | TGGCTTTCAGTAGTTTCATGG |
| hCT1640694-Ex16 | TTGCTTTCCTGAAGTTTCTTTTG | TCAAGTAAGAGGAGGATATGTCAAAG | CATGTGATGGCGTGATCC |
| hCT1640694-Ex17 | GGGGAAAGGCAGTAAAGGTC | CATCAAATATTTCAAAGGTTGAGC | AGGAATACACAAACACCGACAG |
| hCT1640694-Ex18 | TCCTTATTCGTTGTCAGTGATTG | GTCAAAACAAATGGCACACG | TGCACCCTGTTTTCTTTTCTC |
| hCT1640694-Ex19 | CATGGTGAAAGACGATGGAC | TTACAGGCATGAACCACCAC | TGGACAAGTAATGGTTTTCTCTG |
| hCT1640694-Ex20-1 | TGGGGTAAAGGGAATCAAAAG | CCTATGCAATCGGTCTTTGC | TGACATTTGAGCAAAGACCTG |
| hCT1640694-Ex20-2 | TTGCATACATTCGAAAGACC | GGGGATTTTGTTTTGTTTTG | TTGTTTTGTTTTGTTTTT |

[1]SEQ ID NO: 6 to 165 (forward primers)
[2]SEQ ID NO: 166 to 325 (reverse primers)
[3]SEQ lED NO: 326 to 485 (sequencing primers)

Example 2

This Example Demonstrates the Striking Clustering of Mutations within the PIK3CA Gene All coding exons of PIK3CA were then analyzed in an additional 199 colorectal cancers, revealing mutations in a total of 74 tumors (32%) (Table 3 and examples in FIG. 1).

TABLE 3

PIK3CA mutations in human cancers

| | PIK3CA mutations* | | Functional | Tumor type# | | | | | | | | |
|---|---|---|---|---|---|---|---|---|---|---|---|---|
| Exon | Nucleotide | Amino acid | domain | Colon | GBM | Gastric | Breast | Lung | Pancreas | Medullo-blastomas | Adenomas | Total |
| Exon 1 | C112T | R38C | p85 | 1 | | | | | | | | 1 |
| Exon 1 | G113A | R38H | p85 | 2 | | | | | | | | 2 |
| Exon 1 | G263A | R88Q | p85 | 1 | | | | | | | | 1 |
| Exon 1 | C311G | P104R | p85 | 1 | | | | | | | | 1 |
| Exon 1 | G317T | G106V | p85 | 1 | | | | | | | | 1 |
| Exon 1 | G323C | R108P | p85 | 1 | | | | | | | | 1 |
| Exon 1 | del332-334 | delK111 | | 1 | | | | | | | | 1 |
| Exon 2 | G353A | G118D | | 1 | | | | | | | | 1 |
| Exon 2 | G365A | G122D | | 1 | | | | | | | | 1 |
| Exon 2 | C370A | P124T | | 1 | | | | | | | | 1 |
| Exon 4 | T1035A | N345K | C2 | 1 | | | | | | | | 1 |
| Exon 4 | G1048C | D350H | C2 | | 1 | | | | | | | 1 |
| Exon 5 | T1132C | C378R | C2 | | 1 | | | | | | | 1 |
| Exon 7 | T1258C | C420R | C2 | 2 | | | | | | | | 2 |
| Exon 7 | G1357C | E453Q | C2 | 1 | | | | | | | | 1 |
| Exon 9 | C1616G | P539R | Helical | 1 | | | | | | | | 1 |
| Exon 9 | G1624A | E542K | Helical | 9 | | | | | | | 1 | 10 |
| Exon 9 | A1625G | E542G | Helical | 1 | | | | | | | | 1 |
| Exon 9 | A1625T | E542V | Helical | | | | | | | | 1 | 1 |
| Exon 9 | G1633A | E545K | Helical | 21 | | | | 1 | | | | 22 |
| Exon 9 | A1634G | E545G | Helical | 1 | | | | | | | | 1 |
| Exon 9 | G1635T | E545D | Helical | 1 | | | | | | | | 1 |
| Exon 9 | C1636A | Q546K | Helical | 5 | | | | | | | | 5 |
| Exon 9 | A1637C | Q546P | Helical | 1 | | | | | | | | 1 |
| Exon 12 | C1981A | Q661K | Helical | 1 | | | | | | | | 1 |
| Exon 13 | A2102C | H701P | Helical | | 1 | | | | | | | 1 |
| Exon 18 | G2702T | C901F | Kinase | 1 | 1 | | | | | | | 2 |
| Exon 18 | T2725C | F909L | Kinase | 1 | | | | | | | | 1 |
| Exon 20 | T3022C | S1008P | Kinase | 1 | | | | | | | | 1 |
| Exon 20 | A3073G | T1025A | Kinase | 1 | | | | | | | | 1 |

TABLE 3-continued

PIK3CA mutations in human cancers

| | PIK3CA mutations* | | Functional | Tumor type# | | | | | | | | |
|---|---|---|---|---|---|---|---|---|---|---|---|---|
| Exon | Nucleotide | Amino acid | domain | Colon | GBM | Gastric | Breast | Lung | Pancreas | Medullo-blastomas | Adenomas | Total |
| Exon 20 | C3074A | T1025N | Kinase | 1 | | | | | | | | 1 |
| Exon 20 | G3129T | M1043I | Kinase | 2 | | | | | | | | 2 |
| Exon 20 | C3139T | H1047Y | Kinase | 2 | | | | | | | | 2 |
| Exon 20 | A3140G | H1047R | Kinase | 15 | | 2 | 1 | | | | | 18 |
| Exon 20 | A3140T | H1047L | Kinase | 1 | | | | | | | | 1 |
| Bran 20 | G3145A | G1049S | Kinase | | 1 | | | | | | | 1 |
| Tumors with mutations | | | | 74 | 4 | 3 | 1 | 1 | 0 | 0 | 2 | |
| No. samples screened | | | | 234 | 15 | 12 | 12 | 24 | 11 | 12 | 76 | |
| Percent of tumors with mutations | | | | 32% | 27% | 25% | 8% | 4% | 0% | 0% | 3% | |

*Exon number with nucleotide and amino acid change resulting from mutation. Nucleotide position refers to position within coding sequence, where position 1 corresponds to the first position of the start codon. Functional domains are described in FIG. 1 legend.
Number of non-synonymous mutations observed in indicated tumors. Colon, colorectal cancers; GBM, glioblastomas; gastric, gastric cancers; breast, breast cancers; lung, lung cancers; pancreas, pancreatic cancers; medulloblastomas; adenomas, benign colorectal tumors. All mutations listed were shown to be somatic except for five colorectal cancers and one glioblastoma where no corresponding normal tissue was available. Mutations were identified in 58 of 201 mismatch repair (MMR) proficient colorectal cancers, and 16 of 33 MMR-deficient colorectal cancers. Some tumors with PIK3CA mutations contained mutations in KRAS or BRAF while others did not, suggesting that these genes operate through independent pathways. Seven tumors contained two somatic alterations. In addition to the 92 nonsynonymous mutations recorded in the table, we detected 3 synonymous alterations.

Example 3

This Example Demonstrates that the Mutations in PIK3CA Occur Late in Tumorigenesis To determine the timing of PIK3CA mutations during neoplastic progression, we evaluated 76 pre-malignant colorectal tumors of various size and degree of dysplasia.

Only two PIK3CA mutations were found (E542K and E542V), both in very advanced adenomas greater than 5 cm in diameter and of tubuluvillous type. These data suggest that PIK3CA abnormalities occur at relatively late stages of neoplasia, near the time that tumors begin to invade and metastasize.

Example 4

This Example Demonstrates that PIK3CA Mutations in a Variety of Different Cancer Types We then evaluated PIK3CA for genetic alterations in other tumor types (Table 1). Mutations were identified in four of fifteen (27%) glioblastomas, three of twelve (25%) gastric cancers, one of thirteen (8%) breast, and one of twenty four (4%) lung cancers. No mutations were observed in eleven pancreatic cancers or twelve medulloblastomas. In total, 89 mutations were observed, all but 3 of which were heterozygous.

Example 5

This Example Demonstrates the Non-Random Nature of the Genetic Alterations Observed The sheer number of mutations observed in PIK3CA in five different cancer types strongly suggests that these mutations are functionally important. This conclusion is buttressed by two additional independent lines of evidence. First, analysis of the ratio of non-synonymous to synonymous mutations is a good measure of selection during tumor progression, as silent alterations are unlikely to exert a growth advantage. The ratio of non-synonymous to synonymous mutations in PIK3CA was 89 to 2, far higher than the 2:1 ratio expected by chance ($P<1\times10^{-4}$). Second, the prevalence of non-synonymous changes located in the PI3K catalytic and accessory domains was ~120 per Mb tumor DNA, over 100 times higher than the background mutation frequency of nonfunctional alterations observed in the genome of cancer cells ($P<1\times 10^{-4}$) (9).

Although the effect of these mutations on kinase function has not yet been experimentally tested, their positions and nature within PIK3CA imply that they are likely to be activating. No truncating mutations were observed and >75% of alterations occurred in two small clusters in exons 9 and 20 (Table 2 and FIG. 1). The affected residues within these clusters are highly conserved evolutionarily, retaining identity in mouse, rat, and chicken. The clustering of somatic missense mutations in specific domains is similar to that observed for activating mutations in other oncogenes, such as RAS (10), BRAF (11, 12), β-catenin (13), and members of the tyrosine kinome (14).

These genetic data suggest that mutant PIK3CA is likely to function as an oncogene in human cancers.

Example 6

This Example Demonstrates that Gene Amplification of PIK3CA is not Common

Quantitative PCR analysis of PIK3CA in 96 colorectal cancers showed no evidence of gene amplification, suggesting that gene copy alterations are not a significant mechanism of activation in this tumor type. The primers used were:
Real time PI3K hCT1640694 20-1F (intron)

TTACTTATAGGTTTCAGGAGATGTGTT; (SEQ ID NO: 486)

and
Real time PI3K hCT1640694 20-1R

GGGTCTTTCGAATGTATGCAATG (SEQ ID NO: 487)

The Sequence Listing appended to the end of this application contains the following sequences:
SEQ ID NO: 1=coding sequence only (nt 13 to 3201 of SEQ ID NO: 2)
SEQ ID NO: 2=RNA sequence (NM_006218)

SEQ ID NO: 3=protein sequence (NP_006209)
SEQ ID NO: 4=exon 9
SEQ ID NO: 5=exon 20
SEQ ID NO: 6 to 165=forward primers
SEQ ID NO: 166 to 325=reverse primers
SEQ ID NO: 326 to 485=sequencing primers
SEQ ID NO: 486 and 487 amplification primers

REFERENCES AND NOTES

1. R. Katso et al., *Annu Rev Cell Dev Biol* 17, 615-75 (2001).
2. I. Vivanco, C. L. Sawyers, *Nat Rev Cancer* 2, 489-501 (July, 2002).
3. W. A. Phillips, F. St Clair, A. D. Munday, R. J. Thomas, C. A. Mitchell, *Cancer* 83, 41-7 (Jul. 1, 1998).
4. E. S. Gershtein, V. A. Shatskaya, V. D. Ermilova, N. E. Kushlinsky, M. A. Krasil'nikov, *Clin Chim Acta* 287, 59-67 (September, 1999).
5. B. Vanhaesebroeck, M. D. Waterfield, *Exp Cell Res* 253, 239-54 (Nov. 25, 1999).
6. S. Djordjevic, P. C. Driscoll, *Trends Biochem Sci* 27, 426-32 (August, 2002).
7. Catalytic subunits of PI3Ks were identified by analysis of InterPro (IPR) PI3K domains (IPR000403) present within the Celera draft human genome sequence. This resulted in identification of 15 PI3Ks and related PI3K genes. The kinase domain of PIK3CD gene was not represented in the current draft of human genome sequence and was therefore not included in this study.
8. Sequences for all annotated exons and adjacent intronic sequences containing the kinase domain of identified PI3Ks were extracted from the Celera draft human genome sequence (URL address: www host server, domain name celera.com). Celera and Genbank accession numbers of all analyzed genes are available in Table 1. Primers for PCR amplification and sequencing were designed using the Primer 3 program (URL address: http file type, www-genome.wi.mit.edu host server, cgi-bin domain name, primer directory, primer3_www.cgi subdirectory), and were synthesized by MWG (High Point, N.C.) or IDT (Coralville, Iowa). PCR amplification and sequencing were performed on tumor DNA from early passage cell lines or primary tumors as previously described (12) using a 384 capillary automated sequencing apparatus (Spectrumedix, State College, Pa.). Sequence traces were assembled and analyzed to identify potential genomic alterations using the Mutation Explorer software package (SoftGenetics, State College, Pa.). Of the exons extracted, 96% were successfully analyzed. Sequences of all primers used for PCR amplification and sequencing are provided in Table S1.
9. T. L. Wang et al., *Proc Natl Acad Sci USA* 99, 3076-80. (2002).
10. J. L. Bos et al., *Nature* 327, 293-7 (1987).
11. H. Davies et al., *Nature* (Jun. 9, 2002).
12. H. Rajagopalan et al., *Nature* 418, 934. (2002).
13. P. J. Morin et al., *Science* 275, 1787-90 (1997).
14. A. Bardelli et al., *Science* 300, 949 (May 9, 2003).
15. J. Li et al., *Science* 275, 1943-7 (1997).
16. P. A. Steck et al., *Nat Genet.* 15, 356-62 (1997).
17. T. Maehama, J. E. Dixon, *J Biol Chem* 273, 13375-8 (May 29, 1998).
18. M. P. Myers et al., *Proc Natl Acad Sci USA* 95, 13513-8 (Nov. 10, 1998).
19. L. Shayesteh et al., *Nat Genet.* 21, 99-102 (January, 1999).
20. J. Q. Cheng et al., *Proc Natl Acad Sci USA* 89, 9267-71 (Oct. 1, 1992).
21. L. Hu, J. Hofmann, Y. Lu, G. B. Mills, R. B. Jaffe, *Cancer Res* 62, 1087-92 (Feb. 15, 2002).
22. J. Luo, B. D. Manning, L. C. Cantley, Cancer Cell 4, 257-62 (2003).

We claim:

1. A method of assessing cancer in a body sample of a human suspected of having a cancer, comprising the steps of:
   determining presence of a non-synonymous, intragenic mutation in a PIK3CA coding sequence in the body sample, wherein a wild-type PIK3CA coding sequence comprises the sequence shown in SEQ ID NO:2;
   identifying the human as likely to have cancer if the presence of a non-synonymous, intragenic mutation in PIK3CA coding sequence is determined in the body sample.

2. The method of claim 1 wherein the body sample is a first tissue that is suspected of being neoplastic, and the method further comprises the steps of:
   testing a second tissue that is not suspected of being neoplastic for the presence of the non-synonymous mutation, wherein the first and second tissue are isolated from the human;
   identifying the non-synonymous, intragenic mutation as somatic if said mutation is absent in the second tissue.

3. The method of claim 1 wherein the non-synonymous, intragenic mutation is in exon 9 (SEQ ID NO: 4).

4. The method of claim 1 wherein the non-synonymous, intragenic mutation is in exon 20 (SEQ ID NO: 5).

5. The method of claim 1 wherein the non-synonymous, intragenic mutation is in PIK3CA's helical domain (nucleotides 1567-2124 of SEQ ID NO: 2).

6. The method of claim 1 wherein the non-synonymous, intragenic mutation is in PIK3CA's kinase domain (nucleotides 2095-3096 of SEQ ID NO: 2).

7. The method of claim 1 wherein the non-synonymous, intragenic mutation is in PIK3CA's P85BD domain (nucleotides 103-335 of SEQ ID NO: 2).

8. The method of claim 1 wherein the body sample is colorectal tissue.

9. The method of claim 1 wherein the body sample is brain tissue.

10. The method of claim 1 wherein the body sample is gastric tissue.

11. The method of claim 1 wherein the body sample is breast tissue.

12. The method of claim 1 wherein the body sample is lung tissue.

13. The method of claim 1 wherein the body sample is blood, serum, or plasma.

14. The method of claim 1 wherein the body sample is sputum.

15. The method of claim 1 wherein the body sample is saliva.

16. The method of claim 1 wherein the body sample is urine.

17. The method of claim 1 wherein the body sample is stool.

18. The method of claim 1 wherein the body sample is nipple aspirate.

19. The method of claim 1 wherein PIK3CA exons consisting of 9 and 20 are tested to determine a non-synonymous mutation.

20. The method of claim 1 wherein PIK3CA exons comprising 9 and 20 are tested to determine a non-synonymous mutation.

21. The method of claim 1 wherein the non-synonymous, intragenic mutation is a substitution mutation.

22. The method of claim 21 wherein the body sample is further tested for mutations G113A, T1258C, G3129T, and C3139T.

23. The method of claim 1 wherein the non-synonymous, intragenic mutation is G1624A.

24. The method of claim 1 wherein the non-synonymous, intragenic mutation is G1633A.

25. The method of claim 1 wherein the non-synonymous, intragenic mutation is C1636A.

26. The method of claim 1 wherein the non-synonymous, intragenic mutation is A3140G.

27. The method of claim 1 wherein the body sample is tested for mutations at nucleotide positions 1624, 1633, 1636, and 3140 of PIK3CA coding sequence.

28. The method of claim 1 wherein the body sample is tested for mutations G1624A, G1633A, C1636A, and A3140G.

29. The method of claim 28 wherein the body sample is further tested for mutation G2702T.

30. The method of claim 1 wherein the non-synonymous, intragenic mutation is a deletion mutation.

31. A method of characterizing a cancer in a body sample of a human,
comprising the steps of:
testing the body sample to determine the presence of a non-synonymous, intragenic mutation in a PIK3CA coding sequence in the body sample, wherein a wild-type PIK3CA coding sequence comprises the sequence shown in SEQ ID NO:2.

32. The method of claim 31 wherein the body sample is a first tissue that is
suspected of being neoplastic, and the method further comprises the steps of:
testing a second tissue that is not suspected of being neoplastic for the presence of the non-synonymous mutation, wherein the first and second tissue are isolated from the human;
identifying the non-synonymous, intragenic mutation as somatic if said mutation is absent in the second tissue.

33. The method of claim 31 further comprising:
identifying the human as likely to have cancer if a non-synonymous intragenic mutation in PIK3CA coding sequence is determined present in the body sample.

34. The method of claim 31 further comprising:
prescribing a therapeutic regimen based on the presence of the non-synonymous, intragenic mutation.

35. The method of claim 31 wherein progression of disease is followed by the testing of the body sample.

36. The method of claim 31 wherein the non-synonymous, intragenic mutation is in exon 9 (SEQ ID NO: 4).

37. The method of claim 31 wherein the non-synonymous, intragenic mutation is in exon 20 (SEQ ID NO: 5).

38. The method of claim 31 wherein the non-synonymous, intragenic mutation is in PIK3CA's helical domain (nucleotides 1567-2124 of SEQ ID NO: 2).

39. The method of claim 31 wherein the non-synonymous, intragenic mutation is in PIK3CA's kinase domain (nucleotides 2095-3096 of SEQ ID NO: 2).

40. The method of claim 31 wherein the non-synonymous, intragenic mutation is in PIK3CA's P85BD domain (nucleotides 103-335 of SEQ ID NO: 2).

41. The method of claim 31 wherein the body sample is colorectal tissue.

42. The method of claim 31 wherein the body sample is brain tissue.

43. The method of claim 31 wherein the body sample is gastric tissue.

44. The method of claim 31 wherein the body sample is breast tissue.

45. The method of claim 31 wherein the body sample is lung tissue.

46. The method of claim 31 wherein the body sample is blood, serum, or plasma.

47. The method of claim 31 wherein the body sample is sputum.

48. The method of claim 31 wherein the body sample is saliva.

49. The method of claim 31 wherein the body sample is urine.

50. The method of claim 31 wherein the body sample is stool.

51. The method of claim 31 wherein the body sample is nipple aspirate.

52. The method of claim 31 wherein PIK3CA exons consisting of 9 and 20 are tested to determine a non-synonymous mutation.

53. The method of claim 31 wherein PIK3CA exons comprising 9 and 20 are tested to determine a non-synonymous mutation.

54. The method of claim 31 wherein the non-synonymous, intragenic mutation is a substitution mutation.

55. The method of claim 31 wherein the non-synonymous, intragenic mutation is G1624A.

56. The method of claim 31 wherein the non-synonymous, intragenic mutation is G1633A.

57. The method of claim 31 wherein the non-synonymous, intragenic mutation is C1636A.

58. The method of claim 31 wherein the non-synonymous, intragenic mutation is A3140G.

59. The method of claim 31 wherein the body sample is tested for mutations at nucleotide positions 1624, 1633, 1636, and 3140 of PIK3CA coding sequence.

60. The method of claim 31 wherein the body sample is tested for mutations G1624A, G1633A, and A3140G.

61. The method of claim 60 wherein the body sample is further tested for mutations C1636A, G113A, T1258C, G3129T, and C3139T.

62. The method of claim 61 wherein the body sample is further tested for mutation G2702T.

63. The method of claim 31 wherein the non-synonymous, intragenic mutation is a deletion mutation.

* * * * *